(12) United States Patent
Le Gette et al.

(10) Patent No.: US 7,962,970 B2
(45) Date of Patent: Jun. 21, 2011

(54) EAR WARMER HAVING A CURVED EAR PORTION

(75) Inventors: Brian E. Le Gette, Baltimore, MD (US); David L. Reeb, Columbia, MD (US); Alan S. Tipp, Ellicott City, MD (US)

(73) Assignee: 180s, Inc., Baltimore, MD (US)

( * ) Notice: Subject to any disclaimer, the term of this patent is extended or adjusted under 35 U.S.C. 154(b) by 1051 days.

(21) Appl. No.: 10/693,607

(22) Filed: Oct. 27, 2003

(65) Prior Publication Data

US 2005/0034218 A1 Feb. 17, 2005

Related U.S. Application Data

(63) Continuation-in-part of application No. 10/638,476, filed on Aug. 12, 2003, now Pat. No. 7,650,649.

(51) Int. Cl.
*A42B 1/06* (2006.01)

(52) U.S. Cl. .............................. 2/209; 2/208

(58) Field of Classification Search ...... 2/423, 208–209, 2/174; 381/370, 327, 182, 374, 378
See application file for complete search history.

(56) References Cited

U.S. PATENT DOCUMENTS

| | | |
|---|---|---|
| 138,894 A | 5/1873 | Isidor |
| 139,831 A | 6/1873 | Stone |
| 183,359 A | 10/1876 | Abbott |
| 185,506 A | 12/1876 | Edgar |
| 188,292 A | 3/1877 | Greenwood |
| 190,720 A | 5/1877 | Kleinert |
| 359,612 A | 3/1887 | Kleinert |
| 360,985 A | 4/1887 | Basch |
| 365,061 A | 6/1887 | Friedman |
| 375,594 A | 12/1887 | Basch |
| 381,559 A | 4/1888 | Kleinert et al. |
| 503,703 A | 8/1893 | Kleinert |
| 529,176 A | 11/1894 | Kleinert |
| 548,738 A | 10/1895 | Ballard |
| 758,680 A | 5/1904 | Otte |
| 804,731 A | 11/1905 | Keller |

(Continued)

FOREIGN PATENT DOCUMENTS

CA 2180036 1/1997

(Continued)

OTHER PUBLICATIONS

Chicago Tribune article entitled "Winter From Head to Toe Lend an Ear to the Tale of This Intrepid Inventor," by Sid Moody, Feb. 16, 1988, 4 pgs.

(Continued)

*Primary Examiner* — Shaun R Hurley
*Assistant Examiner* — Andrew W Sutton
(74) *Attorney, Agent, or Firm* — Edell, Shapiro & Finnan LLC

(57) ABSTRACT

An ear warmer comprises a frame disposed within a cavity of a shell. The frame includes a band portion and an ear portion. The ear portion includes an inner side disposed adjacent a head of a user when the ear warmer is worn by a user. In one embodiment, the ear portion is curved toward the inner side of the ear portion. In one embodiment, the ear portion is configured to flex when the ear warmer is disposed on a head of a user.

24 Claims, 61 Drawing Sheets

U.S. PATENT DOCUMENTS

| | | | |
|---|---|---|---|
| 836,087 A | 11/1906 | Callahan | |
| 869,741 A | 10/1907 | Seitzman | |
| 932,487 A | 8/1909 | Melio | |
| 953,623 A | 3/1910 | Keller | |
| 1,167,368 A | 4/1916 | Adams-Randall | |
| 1,179,473 A | 4/1916 | Taylor | |
| 1,274,842 A | 8/1918 | Basch | |
| 1,326,875 A | 12/1919 | Miller | |
| 1,398,958 A | 12/1921 | Basch | |
| 1,567,105 A | 12/1925 | Bohlman | |
| 1,577,183 A | 3/1926 | Dowiarz | |
| 1,628,483 A | 5/1927 | Wiegand et al. | |
| 1,873,864 A | 8/1932 | Ely | |
| 1,988,880 A | 1/1935 | Strouse | |
| 2,070,216 A | 2/1937 | Rosenberg | |
| 2,120,189 A * | 6/1938 | Reinemer | 2/209 |
| 2,149,383 A * | 3/1939 | Bean | 2/209 |
| 2,216,954 A | 10/1940 | McDonough | |
| 2,246,031 A | 6/1941 | Baritz et al. | |
| 2,314,782 A | 3/1943 | Goretsky | |
| 2,333,392 A | 11/1943 | Rosenzweig | |
| 2,378,398 A | 6/1945 | Fiedler | |
| 2,405,326 A | 8/1946 | Plotsky | |
| 2,420,245 A | 5/1947 | Hurst | |
| 2,437,049 A | 3/1948 | Salisbury et al. | |
| 2,439,289 A | 4/1948 | Fanslow | |
| 2,447,078 A | 8/1948 | Maxant | |
| 2,532,852 A | 12/1950 | Oaks | |
| 2,572,746 A | 10/1951 | Mougel | |
| 2,582,907 A | 1/1952 | Kaufmann | |
| 2,586,644 A | 2/1952 | Gilbert | |
| 2,615,169 A | 10/1952 | Maxant | |
| 2,651,046 A | 9/1953 | Berg | |
| 2,671,221 A | 3/1954 | Triplett | |
| 2,678,999 A | 5/1954 | Norris | |
| 2,717,930 A | 9/1955 | Hintz | |
| 2,776,436 A | 1/1957 | Berg | |
| 2,782,423 A | 2/1957 | Simon et al. | |
| 2,858,544 A | 11/1958 | Roth | |
| 2,899,683 A | 8/1959 | Wadsworth et al. | |
| 2,946,860 A | 7/1960 | Jansen et al. | |
| 3,087,028 A | 4/1963 | Bonnin | |
| 3,104,398 A | 9/1963 | Palmaer | |
| 3,112,493 A | 12/1963 | Greenberg | |
| 3,119,119 A | 1/1964 | Millinger et al. | |
| 3,119,904 A | 1/1964 | Anson | |
| 3,156,923 A | 11/1964 | Timm | |
| 3,235,882 A | 2/1966 | Coleman | |
| 3,249,949 A | 5/1966 | Rosenberg et al. | |
| 3,308,480 A | 3/1967 | Elder | |
| 3,311,713 A | 3/1967 | Knuebel | |
| 3,440,663 A | 4/1969 | Beguin | |
| 3,447,160 A | 6/1969 | Teder | |
| 3,509,580 A | 5/1970 | Rubenstein et al. | |
| 3,721,993 A | 3/1973 | Lonnstedt | |
| 3,728,741 A | 4/1973 | Lepor | |
| 3,787,899 A | 1/1974 | Krawagna | |
| 3,815,155 A | 6/1974 | Davison et al. | |
| 3,841,325 A | 10/1974 | Pickard | |
| 3,944,018 A | 3/1976 | Satory | |
| 4,048,453 A | 9/1977 | Seidel | |
| 4,065,176 A | 12/1977 | Fontana | |
| 4,133,053 A * | 1/1979 | Lundin | 2/209 |
| 4,277,847 A | 7/1981 | Florio | |
| 4,349,081 A | 9/1982 | Pepple | |
| D266,417 S | 10/1982 | Perez | |
| 4,391,000 A | 7/1983 | Lonnstedt | |
| 4,404,434 A | 9/1983 | Pelt et al. | |
| 4,409,442 A | 10/1983 | Kamimura | |
| 4,445,005 A | 4/1984 | Furuhashi | |
| 4,455,457 A | 6/1984 | Akira | |
| 4,463,223 A | 7/1984 | Yamanoi et al. | |
| 4,471,496 A | 9/1984 | Gardner, Jr. et al. | |
| 4,486,903 A | 12/1984 | Krystal | |
| 4,499,593 A | 2/1985 | Antle | |
| 4,516,274 A | 5/1985 | Buckland | |
| 4,542,803 A | 9/1985 | Houng | |
| 4,546,215 A | 10/1985 | Ferraro | |
| 4,571,746 A | 2/1986 | Görike | |
| 4,609,786 A | 9/1986 | Omoto et al. | |
| 4,615,185 A | 10/1986 | Bollinger | |
| 4,633,530 A | 1/1987 | Satterfield | |
| 4,654,898 A | 4/1987 | Ishikawa | |
| 4,660,229 A | 4/1987 | Harris | |
| 4,662,590 A | 5/1987 | Hungerford, Jr. | |
| 4,669,129 A | 6/1987 | Chance | |
| 4,670,911 A | 6/1987 | Dunford | |
| 4,682,374 A | 7/1987 | Geiser | |
| 4,713,843 A | 12/1987 | Duncan | |
| 4,727,599 A | 2/1988 | Rappaport et al. | |
| 4,747,145 A | 5/1988 | Wiegel | |
| 4,776,042 A | 10/1988 | Hanson et al. | |
| 4,776,044 A | 10/1988 | Makins | |
| 4,783,822 A | 11/1988 | Toole et al. | |
| 4,791,684 A | 12/1988 | Schwartz | |
| 4,796,307 A | 1/1989 | Vantine | |
| 4,802,245 A | 2/1989 | Miano | |
| D301,477 S | 6/1989 | Storyk | |
| 4,845,751 A | 7/1989 | Schwab | |
| 4,858,248 A | 8/1989 | Goldsmith et al. | |
| 4,864,619 A | 9/1989 | Spates | |
| 4,872,219 A | 10/1989 | Duncan | |
| 4,907,266 A | 3/1990 | Chen | |
| 4,918,757 A | 4/1990 | Janssen et al. | |
| 4,969,069 A | 11/1990 | Eichost | |
| 4,982,451 A | 1/1991 | Graham | |
| 5,003,589 A | 3/1991 | Chen | |
| 5,033,094 A | 7/1991 | Hung | |
| 5,035,005 A | 7/1991 | Hung | |
| 5,038,412 A | 8/1991 | Cionni | |
| 5,046,192 A | 9/1991 | Ryder | |
| 5,052,194 A | 10/1991 | Jarus | |
| 5,056,161 A | 10/1991 | Breen | |
| 5,086,789 A | 2/1992 | Tichy | |
| 5,095,382 A | 3/1992 | Abe | |
| 5,113,428 A | 5/1992 | Fitzgerald | |
| 5,117,464 A | 5/1992 | Jones et al. | |
| 5,117,465 A | 5/1992 | MacDonald | |
| 5,164,987 A | 11/1992 | Raven | |
| 5,201,856 A | 4/1993 | Edwards | |
| 5,257,420 A | 11/1993 | Byrne, Jr. | |
| 5,285,530 A | 2/1994 | Nardone, Jr | |
| D346,380 S | 4/1994 | Fitzgerald | |
| 5,303,426 A | 4/1994 | Jones | |
| 5,327,178 A | 7/1994 | McManigal | |
| 5,339,467 A | 8/1994 | Brinkley | |
| 5,357,585 A | 10/1994 | Kumar | |
| 5,410,735 A | 4/1995 | Borchardt et al. | |
| 5,509,146 A | 4/1996 | Bryerton, Sr. | |
| 5,528,774 A | 6/1996 | Sanders | |
| 5,545,859 A | 8/1996 | Ullrich | |
| 5,551,089 A | 9/1996 | Whidden | |
| 5,551,090 A | 9/1996 | Thompson | |
| D375,825 S | 11/1996 | Whidden | |
| 5,617,589 A | 4/1997 | Lacore et al. | |
| 5,625,903 A | 5/1997 | Schultz et al. | |
| 5,673,438 A | 10/1997 | Lambert | |
| 5,691,515 A | 11/1997 | Landis | |
| 5,708,725 A | 1/1998 | Ito | |
| D390,564 S | 2/1998 | Savona | |
| 5,718,001 A | 2/1998 | Wright | |
| 5,721,775 A | 2/1998 | Leifer | |
| 5,724,119 A | 3/1998 | Leight | |
| 5,749,099 A | 5/1998 | Voorhees | |
| 5,793,878 A | 8/1998 | Chang | |
| 5,821,468 A | 10/1998 | Urella et al. | |
| 5,835,609 A | 11/1998 | LeGette et al. | |
| 5,860,166 A | 1/1999 | Ritts | |
| 5,881,390 A | 3/1999 | Young | |
| 5,887,286 A | 3/1999 | Waldron | |
| 5,898,945 A | 5/1999 | Weiser | |
| 5,943,703 A | 8/1999 | Avila, Jr. | |
| 5,951,141 A | 9/1999 | Bradley | |
| 5,953,434 A | 9/1999 | Boyden | |
| 6,016,574 A | 1/2000 | Chen | |
| 6,029,282 A | 2/2000 | Buschman | |
| 6,055,672 A | 5/2000 | Natvig | |

| | | | | | | |
|---|---|---|---|---|---|---|
| 6,065,157 | A | 5/2000 | Felman | DE | 4422767 A1 | 1/1996 |
| 6,094,749 | A | 8/2000 | Proctor | DE | 29800973 U1 | 4/1998 |
| 6,095,146 | A | 8/2000 | Knauer et al. | DE | 29812652 U1 | 3/1999 |
| 6,104,824 | A | 8/2000 | Ito | DE | 20003363 U1 | 8/2000 |
| 6,131,204 | A | 10/2000 | Otey | EP | 126690 A1 | 11/1984 |
| 6,148,446 | A | 11/2000 | Leight | EP | 0745364 A2 | 4/1996 |
| 6,212,282 | B1 | 4/2001 | Mershon | FR | 1353524 | 1/1964 |
| 6,332,223 | B1 | 12/2001 | Le Gette et al. | FR | 2538204 A1 | 12/1982 |
| 6,369,958 | B1 | 4/2002 | Himmele | FR | 2 532 838 A1 | 3/1984 |
| 6,377,697 | B1 | 4/2002 | Cheng | FR | 2 536 253 A | 5/1984 |
| 6,392,196 | B1 | 5/2002 | Lin | GB | 1327614 | 8/1973 |
| 6,406,811 | B1 | 6/2002 | Hall et al. | GB | 2059206 A | 4/1981 |
| 6,499,146 | B2 * | 12/2002 | Bavetta et al. ............ 2/209 | GB | 2062478 A | 5/1981 |
| 6,502,247 | B2 | 1/2003 | Le Gette et al. | GB | 2290696 A | 10/1996 |
| 6,502,248 | B2 | 1/2003 | Le Gette et al. | GB | 2320885 A | 7/1998 |
| D473,539 | S | 4/2003 | O'Leary | GB | 2339642 A | 2/2000 |
| 6,580,800 | B1 | 6/2003 | Yamasaki et al. | JP | 4719024 | 11/1972 |
| 6,735,784 | B2 | 5/2004 | Isom et al. | JP | 4875626 | 9/1973 |
| 6,744,901 | B2 | 6/2004 | Ito et al. | JP | 53143627 | 11/1978 |
| 6,873,862 | B2 | 3/2005 | Reshefsky | JP | 54-168912 U | 11/1979 |
| 6,888,950 | B2 | 5/2005 | Siskin et al. | JP | 56-146719 U | 11/1981 |
| 6,918,678 | B2 | 7/2005 | McClanahan | JP | 56-152479 | 11/1981 |
| 6,920,645 | B2 | 7/2005 | LeGette et al. | JP | 56-164218 U | 12/1981 |
| 6,978,483 | B2 * | 12/2005 | Isom et al. ............ 2/209 | JP | 5711884 | 1/1982 |
| 6,980,165 | B2 | 12/2005 | Yuasa et al. | JP | 57-205216 | 12/1982 |
| 7,020,902 | B1 | 4/2006 | Tyler | JP | 5815618 | 1/1983 |
| 7,024,013 | B1 | 4/2006 | Van Dam et al. | JP | 58-37289 U | 3/1983 |
| 7,072,483 | B2 | 7/2006 | Lenhard-Backhaus | JP | 58-54191 U | 4/1983 |
| 7,114,823 | B2 | 10/2006 | McCullough et al. | JP | 58-104076 | 7/1983 |
| 7,165,272 | B2 | 1/2007 | Hudson et al. | JP | 58138484 | 9/1983 |
| D541,482 | S | 4/2007 | LeGette et al. | JP | 58-182594 U | 12/1983 |
| D545,001 | S | 6/2007 | LeGette et al. | JP | 59129815 | 8/1984 |
| 7,318,654 | B2 | 1/2008 | McClanahan | JP | 6029141 | 2/1985 |
| 7,377,666 | B1 | 5/2008 | Tyler | JP | 60244188 | 12/1985 |
| 7,424,125 | B2 | 9/2008 | Amae et al. | JP | 61-42186 | 3/1986 |
| 7,548,617 | B2 | 6/2009 | Yuen | JP | 62-3526 | 1/1987 |
| 7,617,543 | B2 | 11/2009 | LeGette et al. | JP | 6221016 | 2/1987 |
| 2001/0017925 | A1 | 8/2001 | Ceravolo | JP | 6320232 | 6/1988 |
| 2002/0172390 | A1 | 11/2002 | Roberts | JP | 1068506 A | 3/1989 |
| 2003/0037366 | A1 | 2/2003 | Lindgren | JP | 1068508 A | 3/1989 |
| 2003/0088905 | A1 | 5/2003 | Bavetta et al. | JP | 1-125320 U | 8/1989 |
| 2004/0252487 | A1 | 12/2004 | McCullough et al. | JP | 63-21972 | 8/1989 |
| 2005/0028250 | A1 | 2/2005 | Zaic | JP | 5-207581 | 8/1993 |
| 2005/0034216 | A1 | 2/2005 | Le Gette et al. | JP | 6-41720 | 6/1994 |
| 2005/0034217 | A1 | 2/2005 | Healy et al. | JP | 641720 | 6/1994 |
| 2005/0036643 | A1 | 2/2005 | Le Gette et al. | JP | 6-351090 A | 12/1994 |
| 2005/0100184 | A1 | 5/2005 | Siskin et al. | JP | 3053142 U | 8/1998 |
| 2005/0241047 | A1 | 11/2005 | Bavetta et al. | JP | 10-85251 | 8/1999 |
| 2005/0246815 | A1 | 11/2005 | LeGette et al. | JP | 11-229223 | 8/1999 |
| 2006/0000006 | A1 | 1/2006 | Gellis et al. | JP | 10257581 | 8/2000 |
| 2006/0206983 | A1 | 9/2006 | Isom et al. | JP | 3082758 | 10/2001 |
| 2007/0107110 | A1 | 5/2007 | LeGette et al. | JP | 2002-11036 A | 1/2002 |
| 2007/0154029 | A1 | 7/2007 | Werner | KR | 20-0226271 | 6/2001 |
| 2007/0160249 | A1 | 7/2007 | LeGette et al. | KR | 20-0314976 | 6/2003 |
| 2007/0199133 | A1 | 8/2007 | Bavetta et al. | KR | 30-0336877 | 11/2003 |
| 2007/0226876 | A1 | 10/2007 | Foust et al. | KR | 10-0703878 | 4/2007 |
| 2008/0044052 | A1 | 2/2008 | Whipple | WO | WO 92/17079 | 10/1992 |
| 2008/0141439 | A1 | 6/2008 | Healy et al. | WO | 9402043 A1 | 2/1994 |
| 2008/0181429 | A1 | 7/2008 | Fried | WO | WO 94/09734 | 5/1994 |
| 2008/0216214 | A1 | 9/2008 | Dolby | WO | WO 97/48296 | 12/1997 |
| 2008/0279403 | A1 | 11/2008 | Pedersen et al. | WO | WO 98/07062 | 2/1998 |
| 2008/0307562 | A1 | 12/2008 | Tipp | WO | WO 98/31314 | 7/1998 |
| 2008/0307563 | A1 | 12/2008 | Le Gette et al. | WO | WO 01/76402 A1 | 10/2001 |
| 2008/0307564 | A1 | 12/2008 | Le Gette et al. | WO | WO 02/083044 | 10/2002 |
| 2008/0307565 | A1 | 12/2008 | Le Gette et al. | WO | WO 03/086124 | 10/2003 |
| 2009/0013447 | A1 | 1/2009 | Drosihn | | | |
| 2009/0013448 | A1 | 1/2009 | Drosihn | | | |
| 2009/0154740 | A1 | 6/2009 | Regen et al. | | | |
| 2009/0196543 | A1 | 8/2009 | Lagakos et al. | | | |
| 2009/0205110 | A1 | 8/2009 | Chiang | | | |
| 2010/0175165 | A1 | 7/2010 | Le Gette | | | |

FOREIGN PATENT DOCUMENTS

| | | |
|---|---|---|
| CH | 294003 | 1/1954 |
| CH | 662052 | 9/1987 |
| CN | 2291138 | 9/1998 |
| CN | 2353337 Y | 12/1999 |
| DE | 2516709 A1 | 10/1976 |
| DE | 3231218 A1 | 2/1984 |

OTHER PUBLICATIONS 1999-2000 Catalog, "Accessory Goods", Nitty Company, Ltd., 4 pages.
Advertisement: The "PODZ" ear warming eye glass retainer, Shred Alert Products of Hood River, Oregon, 5 pages.
2003 Catalog, "Join the Polar Fusion Revolution; Revolutionary Ear Warmers", Polar Fusion, LLC, 2 pages.
Nitty Company Ltd. Winter '89–'90 catalog, 6 pages.
Nitty Company Ltd., Winter '90–'91 catalog, 4 pages.
"Hearmuff: Fleece headwear with internal stereo headphones" from http://www.hearmuff.com/index.htm, 2003, 1 pg.

"Hearmuffs" from http://www.hearmuff.com/goods.htm, 2003, 2 pgs.

"Hearmuffs" from http://www.hearmuff.com/about.htm, 2003, 3 pgs.

PTO Reference, "History of the United States Patent Office", The Patent Office Pony, A History of the Early Patent Office, Kenneth W. Bobyns, 1994, 47 pages (see at least pp. 2-3 of Chapter 29 section).

International Search Report for PCT/US2004/025787, 3 pages.

Defendant Gordini's First Supplemental and Amended Answers and Objections to Plaintiffs Second Set of Interrogatories (Non-Confidential Version) from *180s, Inc. and 180s, LLC* v. *Gordini U.S.A., Inc.* (Case 1:08-cv-00177-JFM), 29 pages, dated Feb. 4, 2009.

Opinion from the District Court of Maryland in *180s, Inc. and 180s, LLC* v. *Gordini U.S.A., Inc.* (Case 1:08-cv-00177-JFM), 23 pages, Mar. 30, 2010.

* cited by examiner

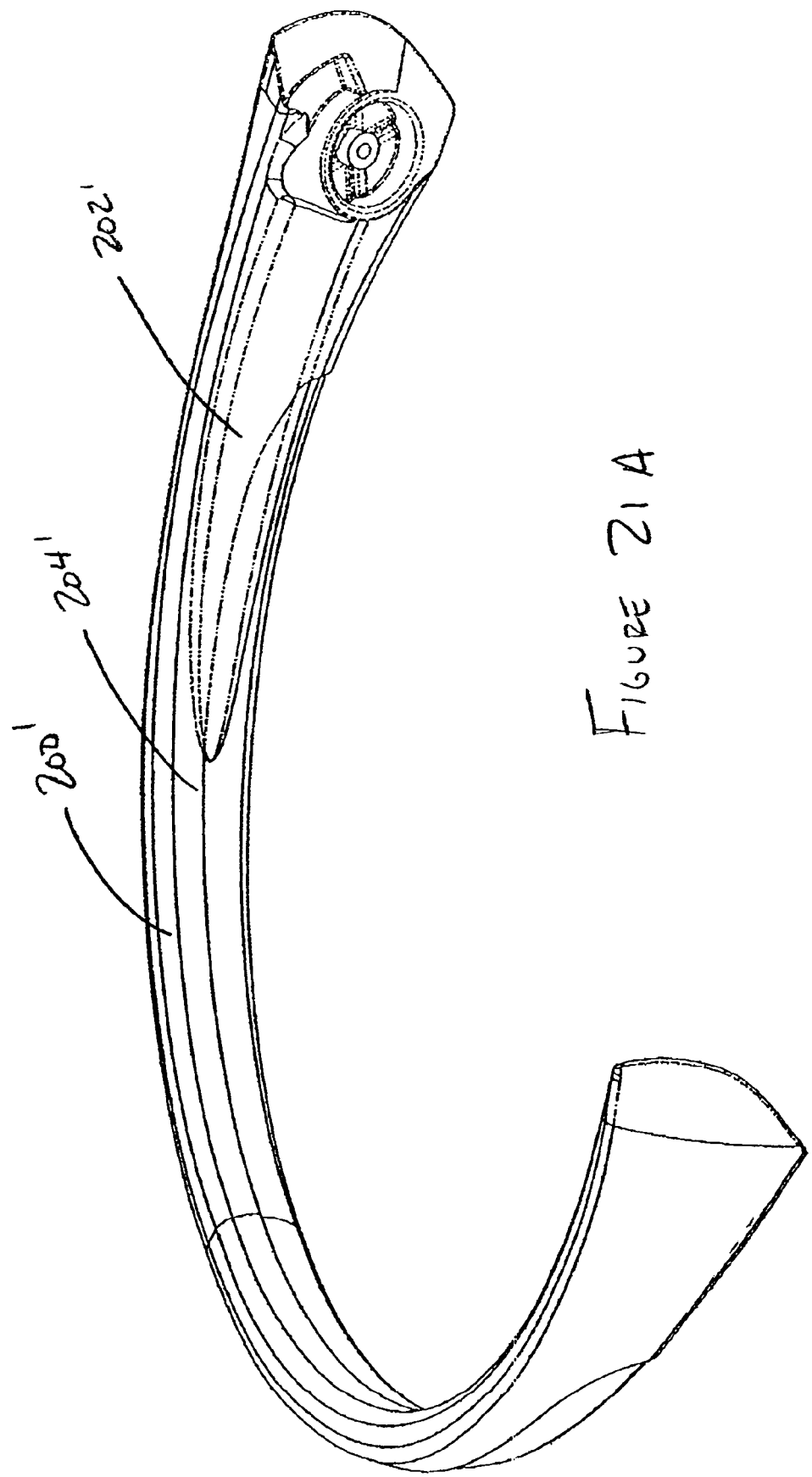

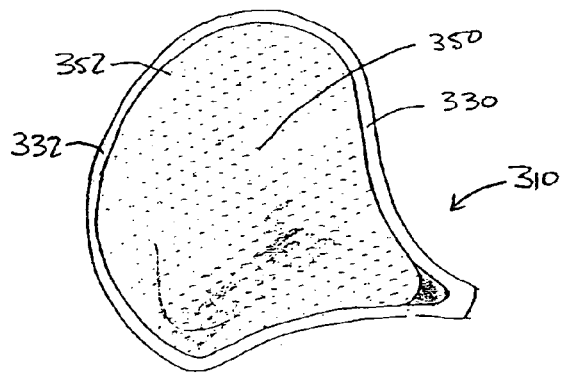
Figure 26
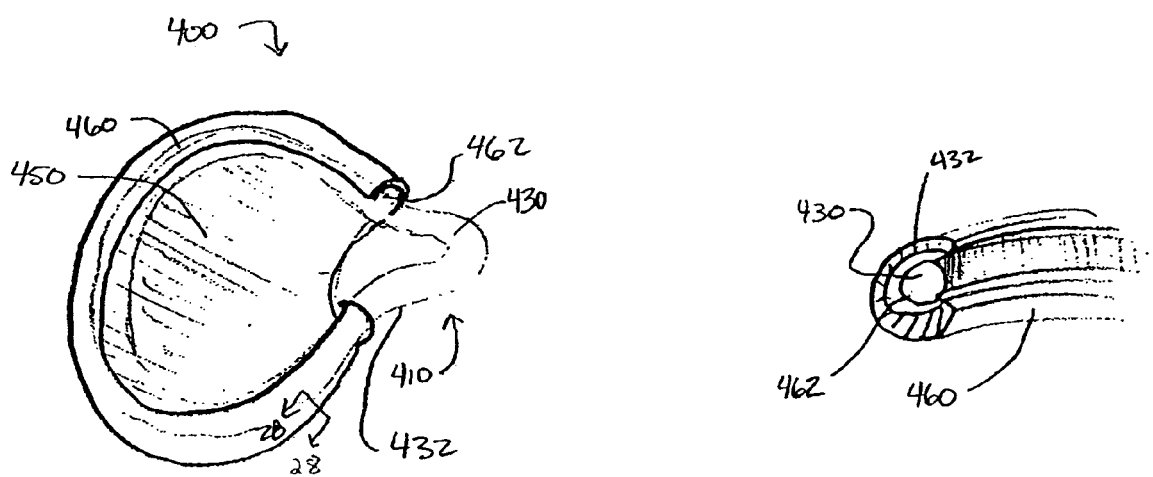
Figure 27
Figure 28

FIGURE 60
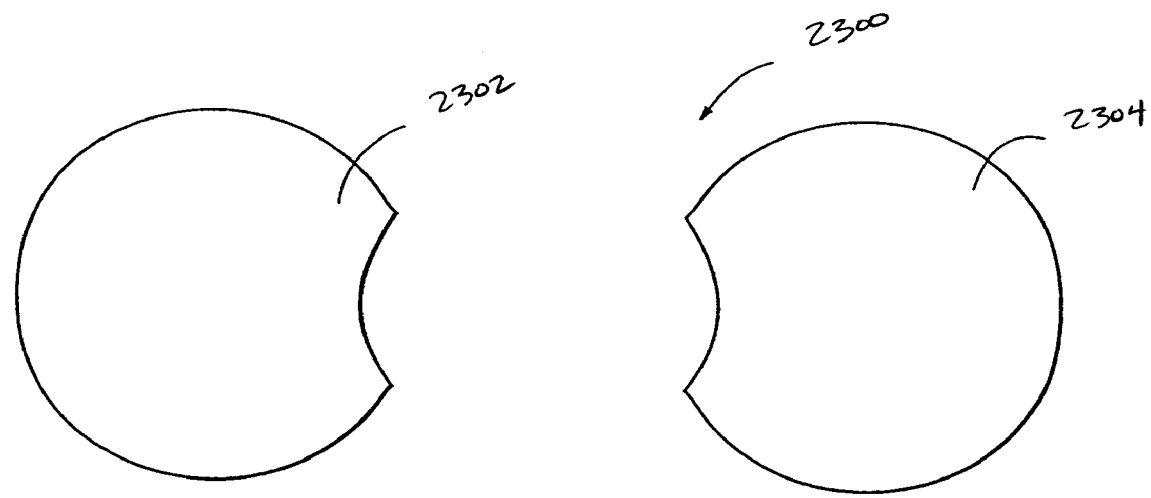
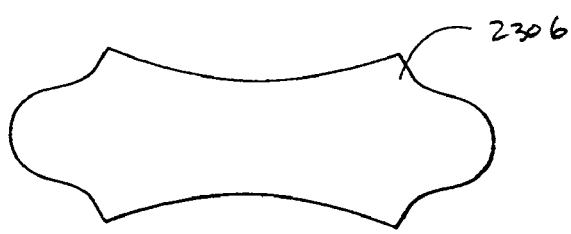
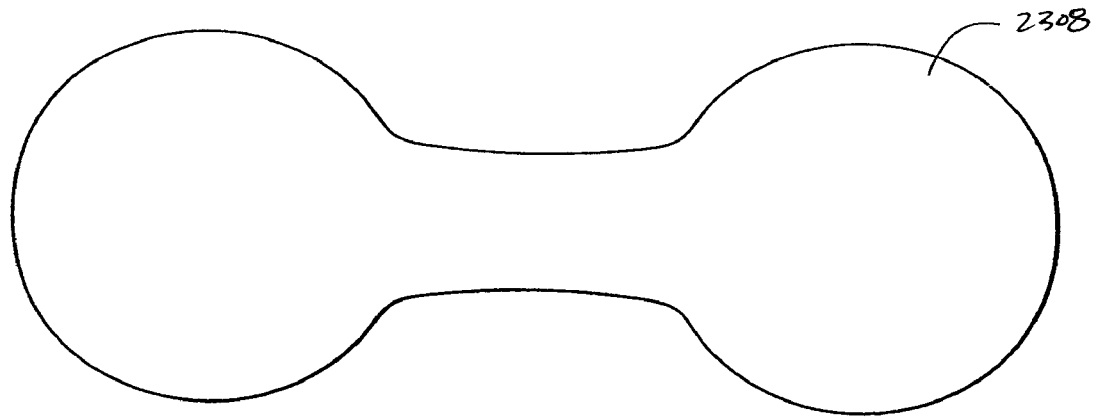

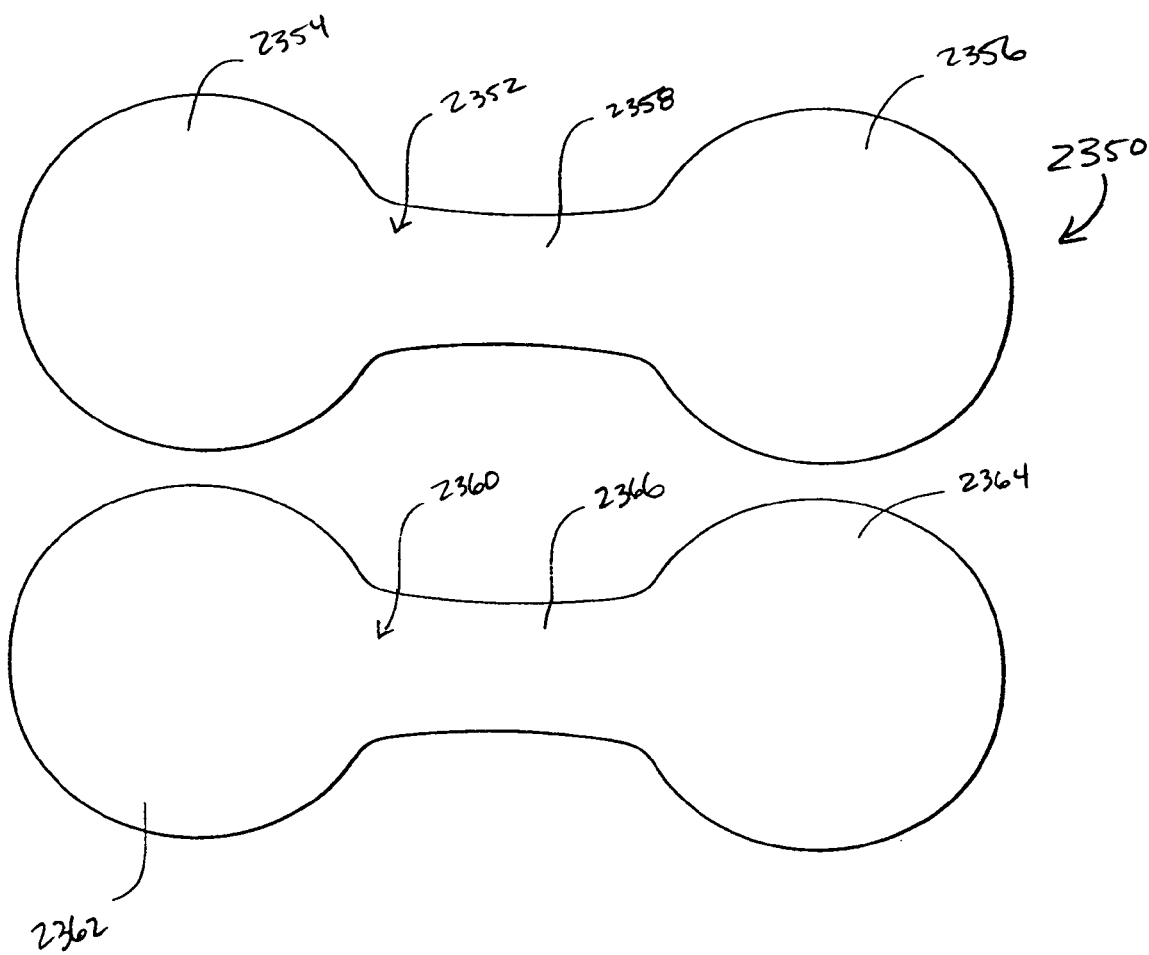

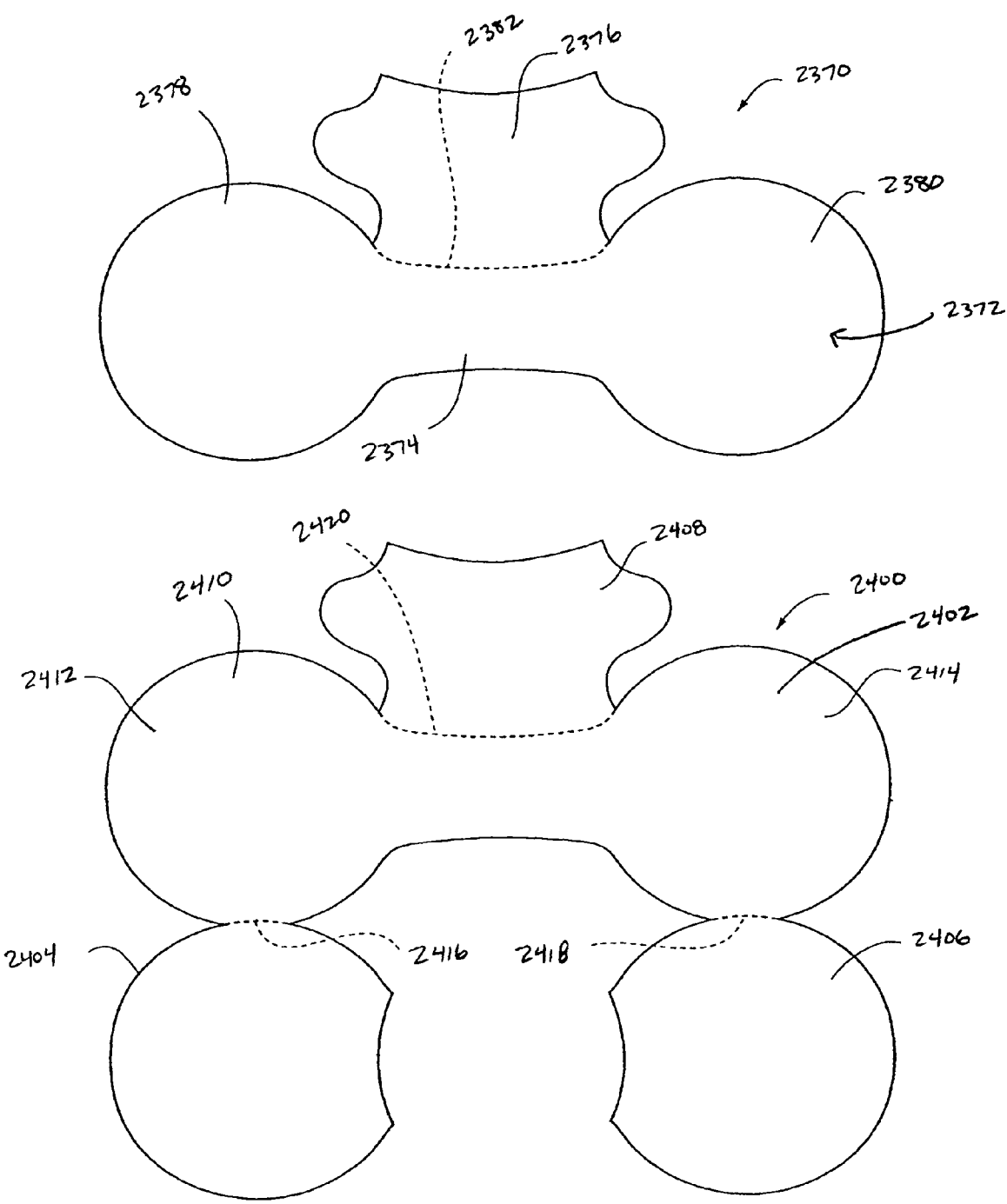

EAR WARMER HAVING A CURVED EAR PORTION

CROSS-REFERENCES TO OTHER APPLICATIONS

This application is a continuation-in-part of U.S. patent application Ser. No. 10/638,476, entitled "Ear Warmer Having An External Frame," filed Aug. 12, 2003 now U.S. Pat. No. 7,650,649, the disclosure of which is incorporated herein by reference in its entirety. Additionally, this application is related to U.S. patent application Ser. No. 10/638,554, entitled "Ear Warmer Having a Membrane Forming a Receptacle," filed Aug. 12, 2003; and U.S. patent application Ser. No. 10/638,553, entitled "Ear Warmer With a Speaker System," filed Aug. 12, 2003; the disclosure of each of which is incorporated herein by reference.

BACKGROUND OF THE INVENTION

This invention relates generally to ear warmers, and in particular to ear warmers that have a frame and are configured to extend around a back of a user's head.

Conventional ear warmers extend over a top of a user's head. Such a conventional ear warmer typically has a frame and a layer of fabric on each side of an ear portion of the frame. These layers of fabric and the frame itself typically have a weight appropriate for sedentary outdoor-activities, but not for non-sedentary outdoor-activities such as running or jogging. In other words, when participating in certain outdoor activities, the participant desires apparel that keeps him or her warm while minimizing the weight of such apparel. While capable of keeping the user warm, conventional ear warmers do not have such desired minimal weight.

Thus, a need exists for an ear warmer that is lightweight while still providing warmth to the user.

SUMMARY OF THE INVENTION

An ear warmer comprises a frame disposed within a cavity of a shell. The frame includes a band portion and an ear portion. The ear portion includes an inner side disposed adjacent a head of a user when the ear warmer is worn by a user. In one embodiment, the ear portion is curved toward the inner side of the ear portion. In one embodiment, the ear portion is configured to flex when the ear warmer is disposed on a head of a user.

BRIEF DESCRIPTION OF THE DRAWINGS

FIG. 21A is a perspective view of an alternative embodiment of a band portion of a frame according to an embodiment of the invention.

FIG. 26 is a side view of a portion of an ear warmer according to an embodiment of the invention.

FIGS. 27 and 28 are a side view and cross-section view along line 28-28, respectively, of a portion of an ear warmer having a press-fit connection, according to an embodiment of the invention.

FIG. 60 illustrates a set of membranes for use in constructing a shell of an ear warmer according to an embodiment of the invention.

FIG. 65 illustrates a set of membranes for use in constructing another shell for an ear warmer according to an embodiment of the invention.

FIG. 66 illustrates a membrane for use in constructing another shell for an ear warmer according to an embodiment of the invention.

FIG. 67 illustrates a membrane for use in constructing another shell for an ear warmer according to an embodiment of the invention.

DETAILED DESCRIPTION

An ear warmer comprises a frame and a fabric member. The frame has an ear portion and a band portion. The ear portion of the frame includes a first side and a second side opposite the first side. The first side of the ear portion defines an interior portion of an opening. The second side of the ear portion defines an exterior portion of the opening. The fabric member includes at least its own ear portion coupled to a portion of the frame. In one embodiment, the ear portion of the fabric member covers the interior portion of the opening in substantially its entirety. In one embodiment, the ear portion of the fabric member covers less than an entirety of the exterior portion of the opening. The term "less than an entirety" should be understood to mean that the fabric member covers some of the exterior portion of the opening or none of the exterior portion of the opening.

In one embodiment, an ear warmer comprises a frame disposed within a cavity of a shell. The frame includes a band portion and an ear portion. The ear portion includes an inner side disposed adjacent a head of a user when the ear warmer is worn by a user. In one embodiment, the ear portion is curved toward the inner side of the ear portion. In one embodiment, the ear portion is configured to flex when the ear warmer is disposed on a head of a user.

Figure 1:
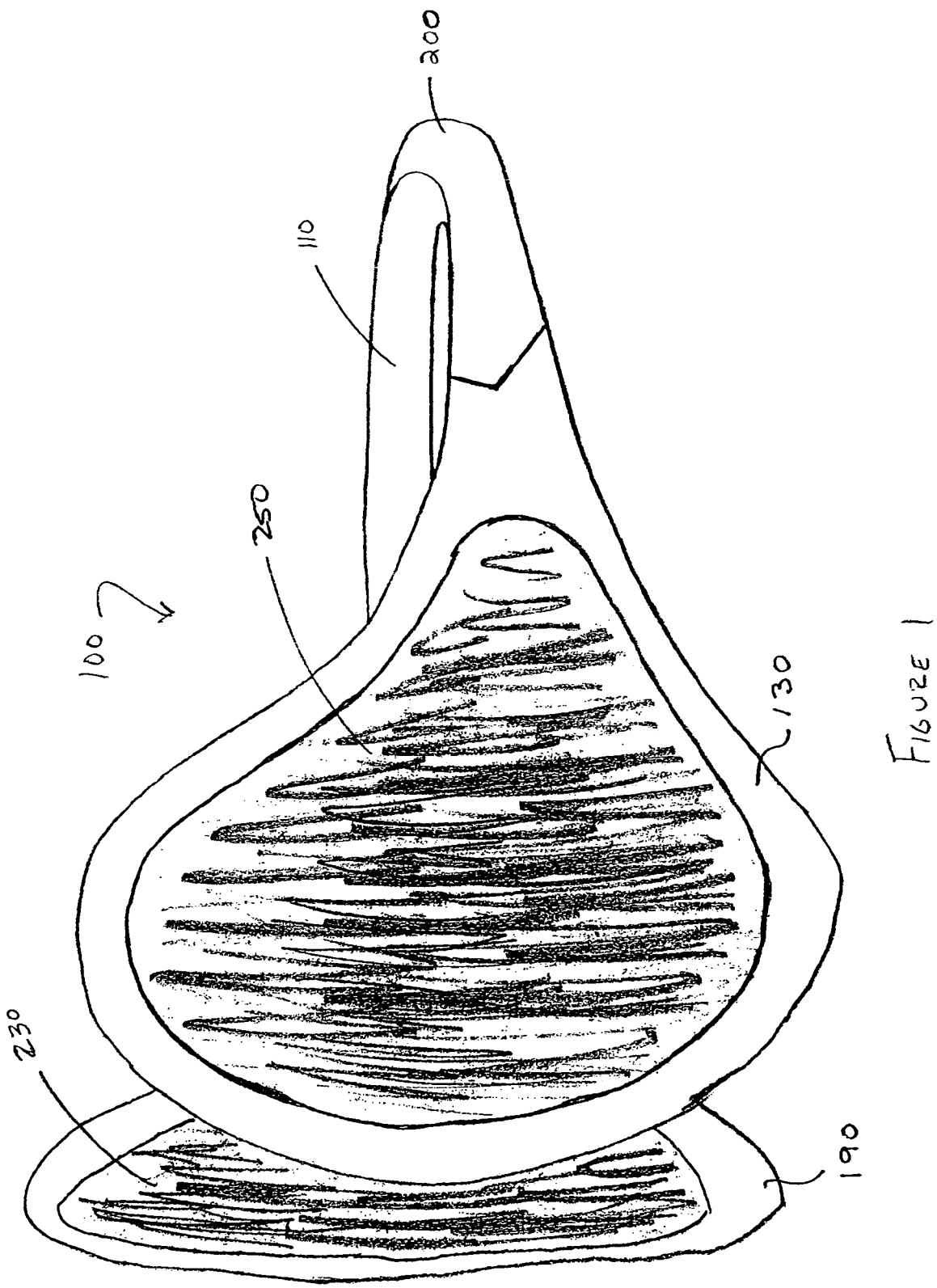
FIG. 1 is a perspective view of an ear warmer in an expanded configuration according to an embodiment of the invention.
Figure 2:
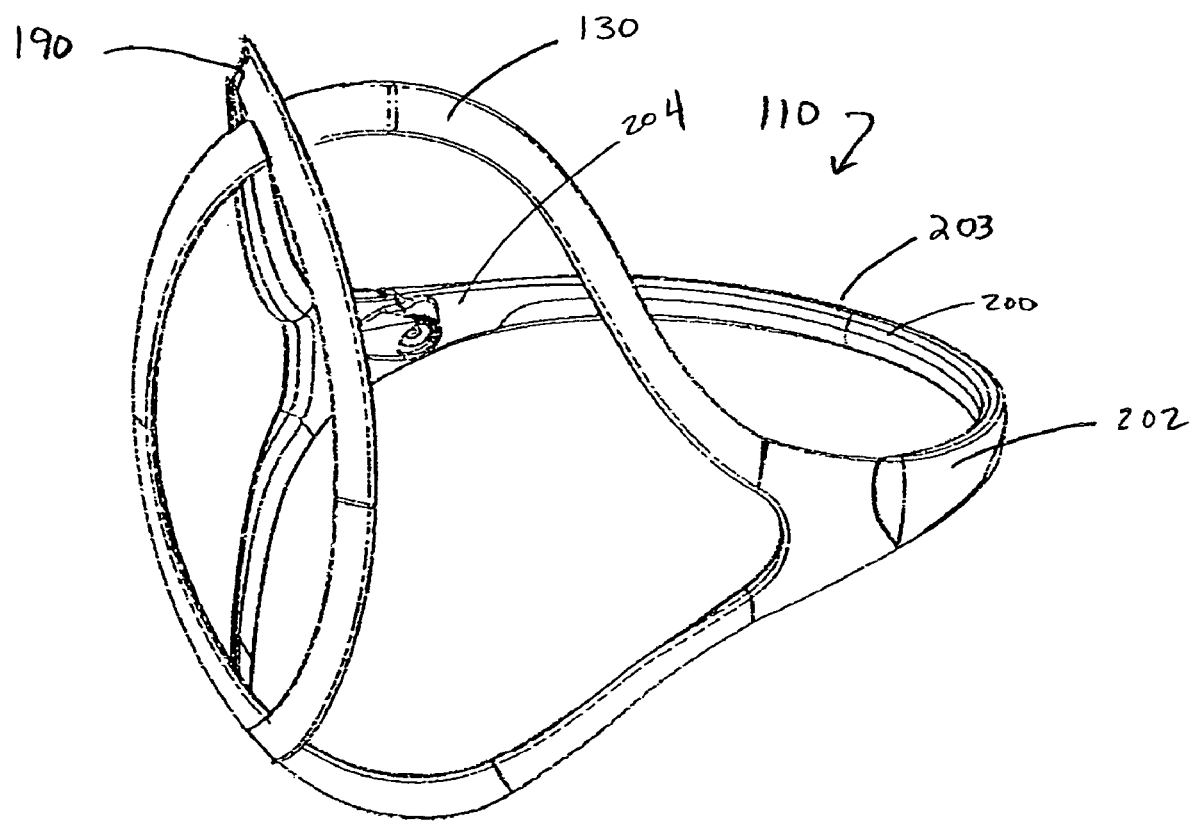
FIG. 2 is a front perspective view of the frame of the ear warmer illustrated in FIG. 1.
Figure 3:
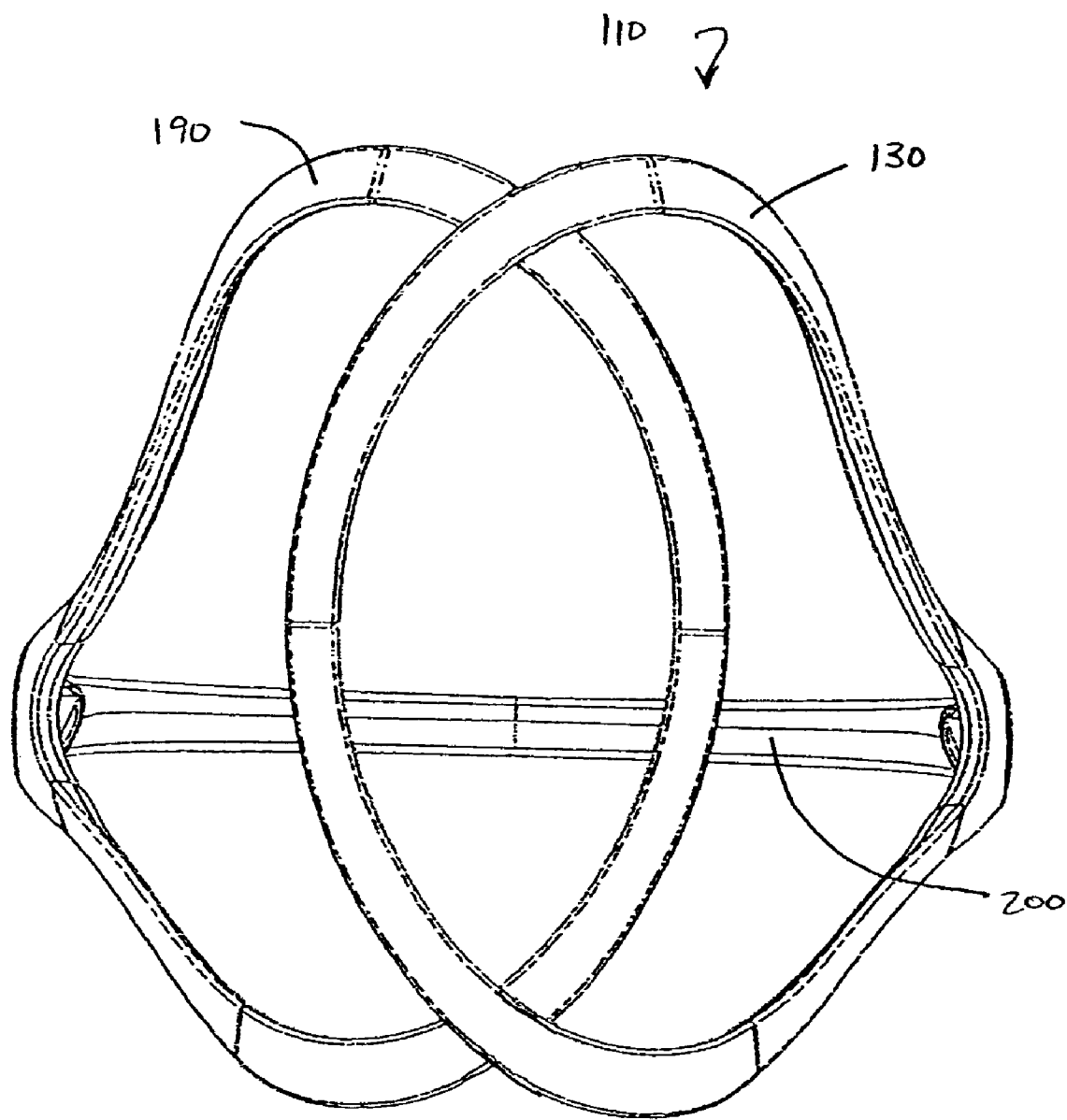
FIG. 3 is a front view of the frame of the ear warmer illustrated in FIG. 2.

An ear warmer 100 according to an embodiment of the invention is illustrated in FIG. 1. In this embodiment, the ear warmer 100 includes a frame 110 and two fabric members 230 and 250. The ear warmer 100 is disposable in an expanded configuration and in a collapsed configuration. The frame 110 of the ear warmer 100 includes a first ear portion 130, a second ear portion 190 and a band portion 200. In this embodiment, fabric member 250 is coupled to the first ear portion 130. Similarly, fabric member 230 is coupled to the second ear portion 190. The fabric members 230 and 250 can be fixedly or removably coupled to the respective ear portions. Various techniques for coupling of the fabric members 230 and 250 are discussed below in detail.

In an alternative embodiment, the frame 110 can be a single piece of material in which the first ear portion 130, the second ear portion 190 and the band portion 200 are formed monolithically (i.e., unitary construction). In another embodiment, the band portion 200 can be adjustable in length. In another embodiment, the first ear portion 130 and the second ear portion 190 can be fixedly coupled to the band portion 200.

Figure 22:
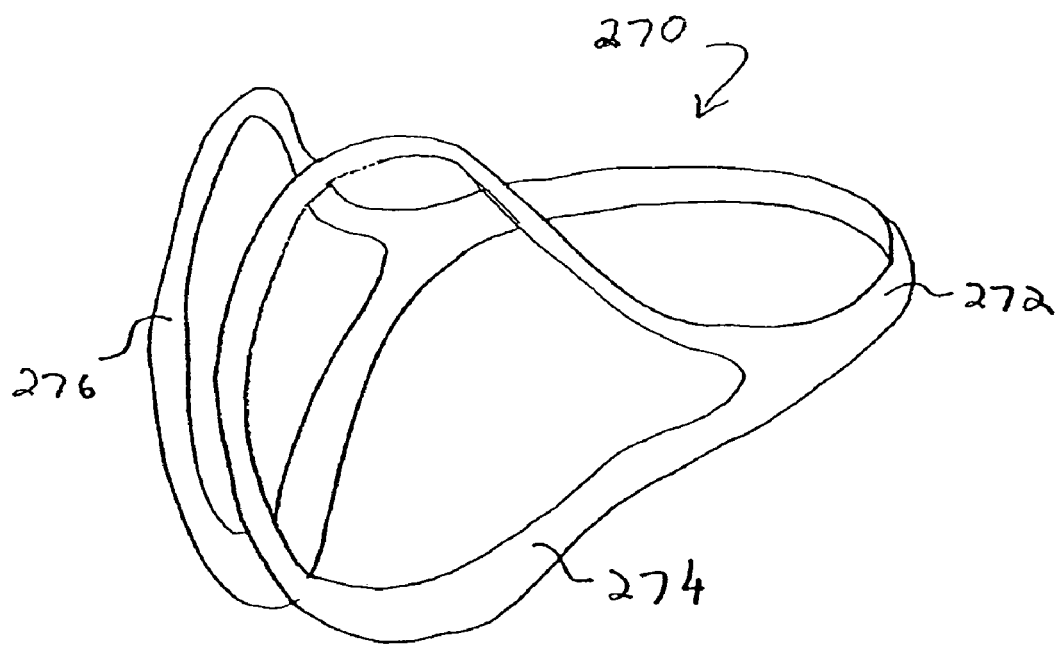
FIGS. 22-23 are perspective views of frames according other embodiments of the invention.

An embodiment of a single-piece frame is illustrated in FIG. 22. In this embodiment, the frame 270 includes a band portion 272, a first ear portion 274 and a second ear portion 276. The first ear portion 274 and the second ear portion 276 are not collapsible with respect to the band portion 272. The frame 270 can have an expanded configuration corresponding to a position on the user's head and an unexpanded configuration corresponding to a position off the user's head. The frame 270 can have an inward bias that defines the unexpanded configuration. Although the user's head is not shown, FIG. 22 shows the frame 270 in the expanded configuration. In alternative embodiments, the position of ear portions 274 and 276 in the expanded and unexpanded configurations can differ from that shown in FIG. 22.

Figure 23:
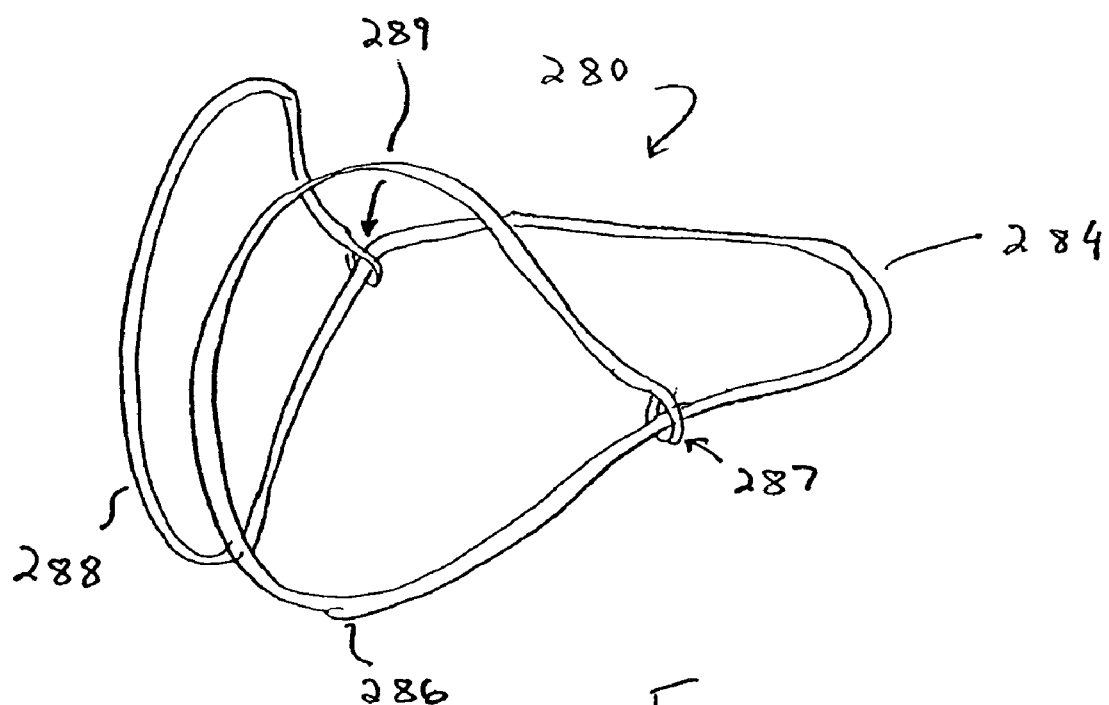

An embodiment of an alternative frame is illustrated in FIG. 23. In this embodiment, the frame 280 has unitary construction including a band portion 284, a first ear portion 286 and a second ear portion 288. The first ear portion 286 has an end portion 287 that couples to the band portion 284. The second ear portion 288 has an end portion 289 that couples to the band portion 284. In this embodiment, the ends 287 and 289 are wrapped around the band portion 284.

Figure 10:
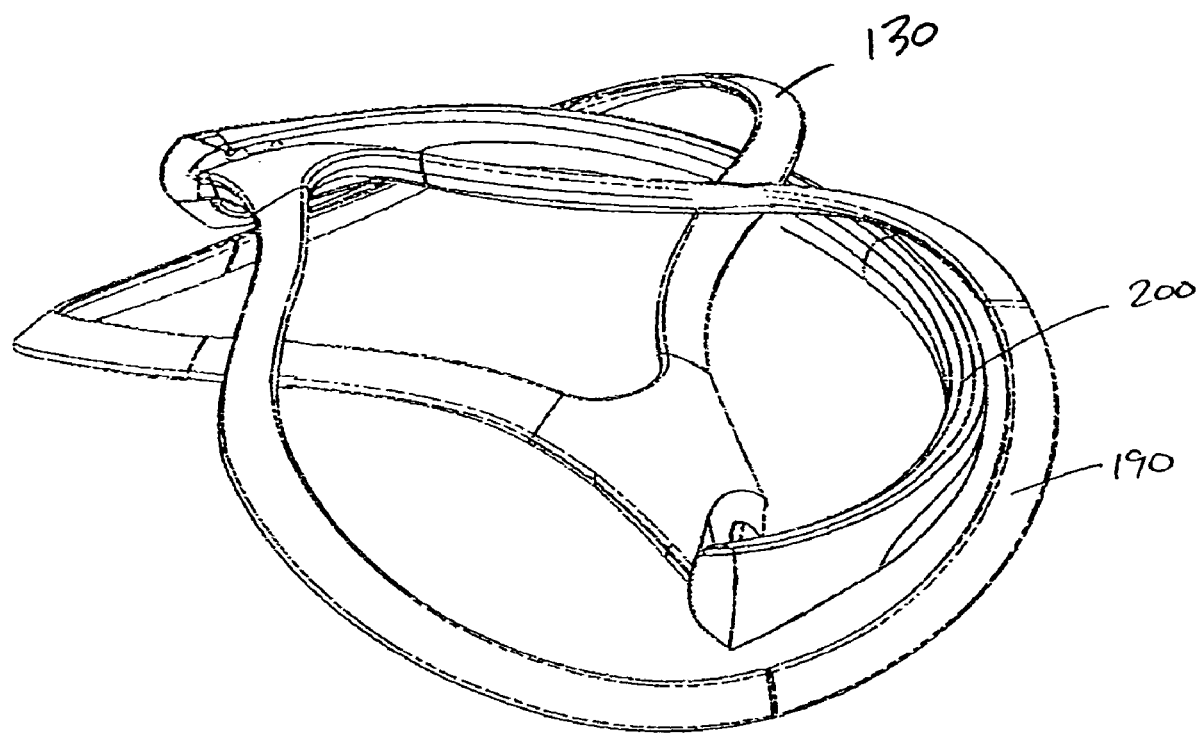
FIG. 10 is a perspective view of the frame of the ear warmer illustrated in FIG. 2 in a collapsed configuration.
Figure 11:
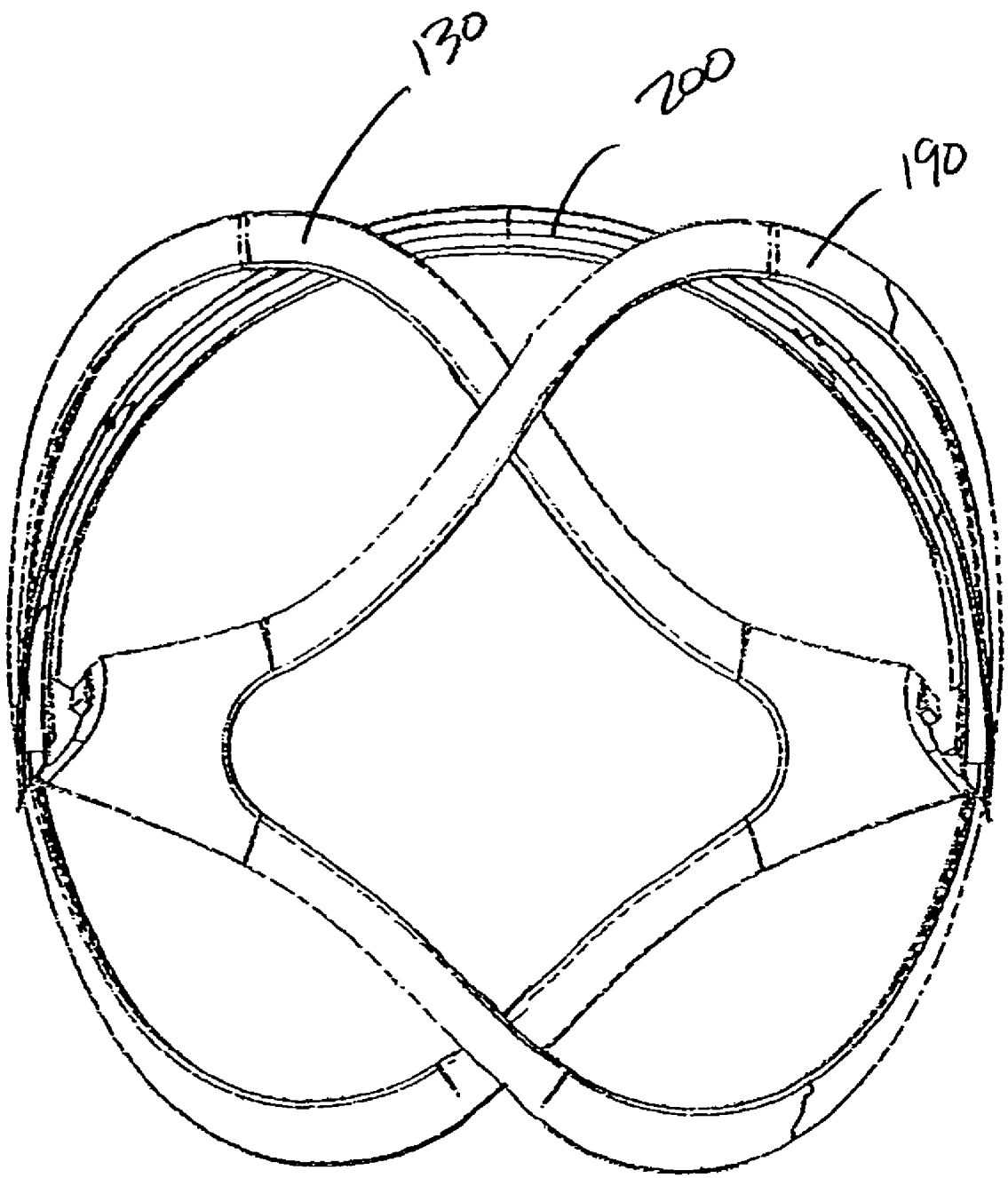
FIG. 11 is a top view of the frame of the ear warmer illustrated in FIG. 2 in a collapsed configuration.
Figure 12:
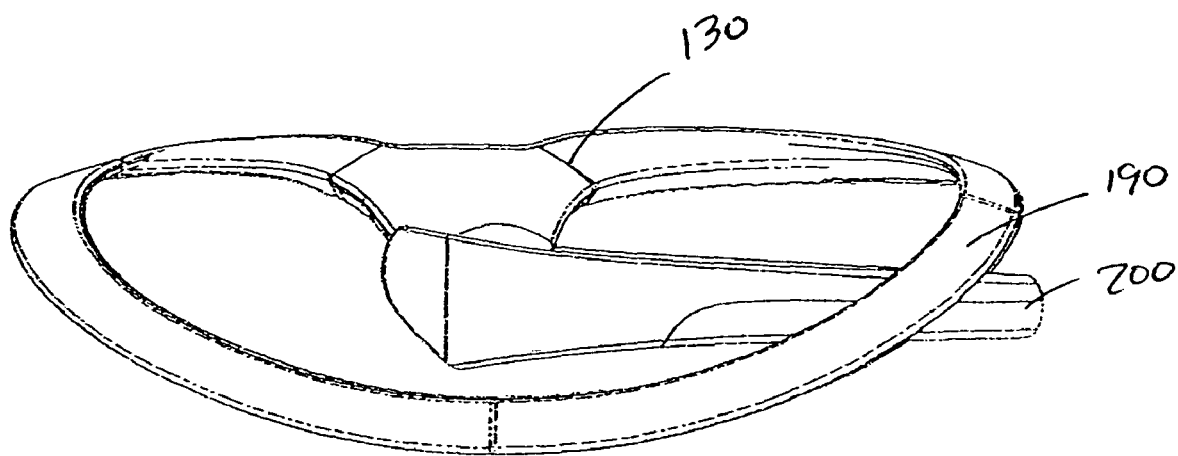
FIG. 12 is a side view of the frame of the ear warmer illustrated in FIG. 2 in a collapsed configuration.

FIGS. 2 through 9 illustrate the frame 110 of the ear warmer 100 in an expanded configuration. FIGS. 10 through 12 illustrate the frame 110 of the ear warmer 100 in a collapsed configuration. The frame 110 includes a band portion 200, a first ear portion 130 coupled to the band portion 200, and a second ear portion 190 coupled to the band portion 200.

As illustrated in FIGS. 2 through 9 and 17 through 21, the band portion 200 is configured to extend around the back of a user's head. The band portion 200 includes a middle portion 203, a first end portion 202, and a second end portion 204. The band portion 200 has an inner side 206 (the side that is disposed adjacent a user when the ear warmer is worn by the user), an outer side 208 (the side opposite the inner side and distal from a user when the ear warmer is worn by the user), an upper side 210 (the side that faces up when the ear warmer is worn by a user), and a lower side 212 (the side that faces down when the ear warmer is worn by a user).

Figure 4:
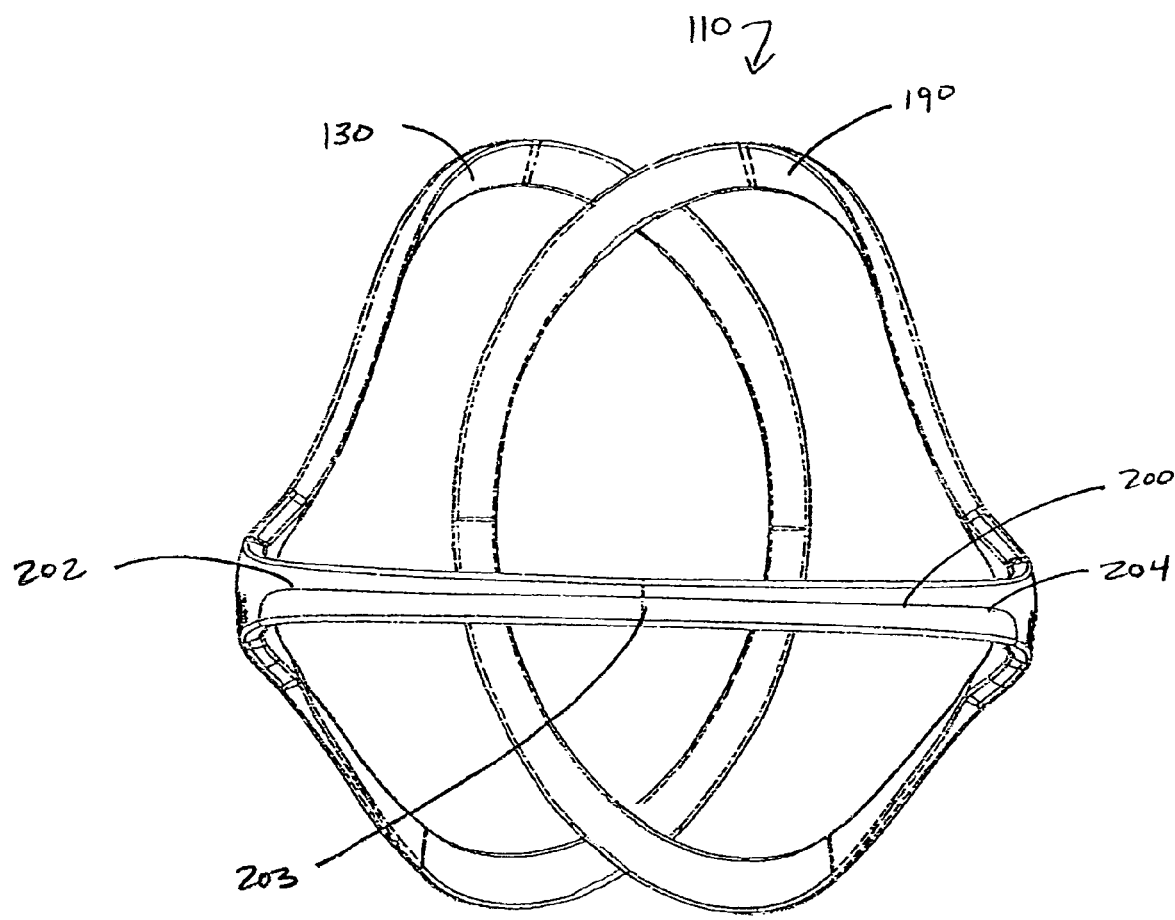
FIG. 4 is a rear view of the frame of the ear warmer illustrated in FIG. 2.
Figure 5:
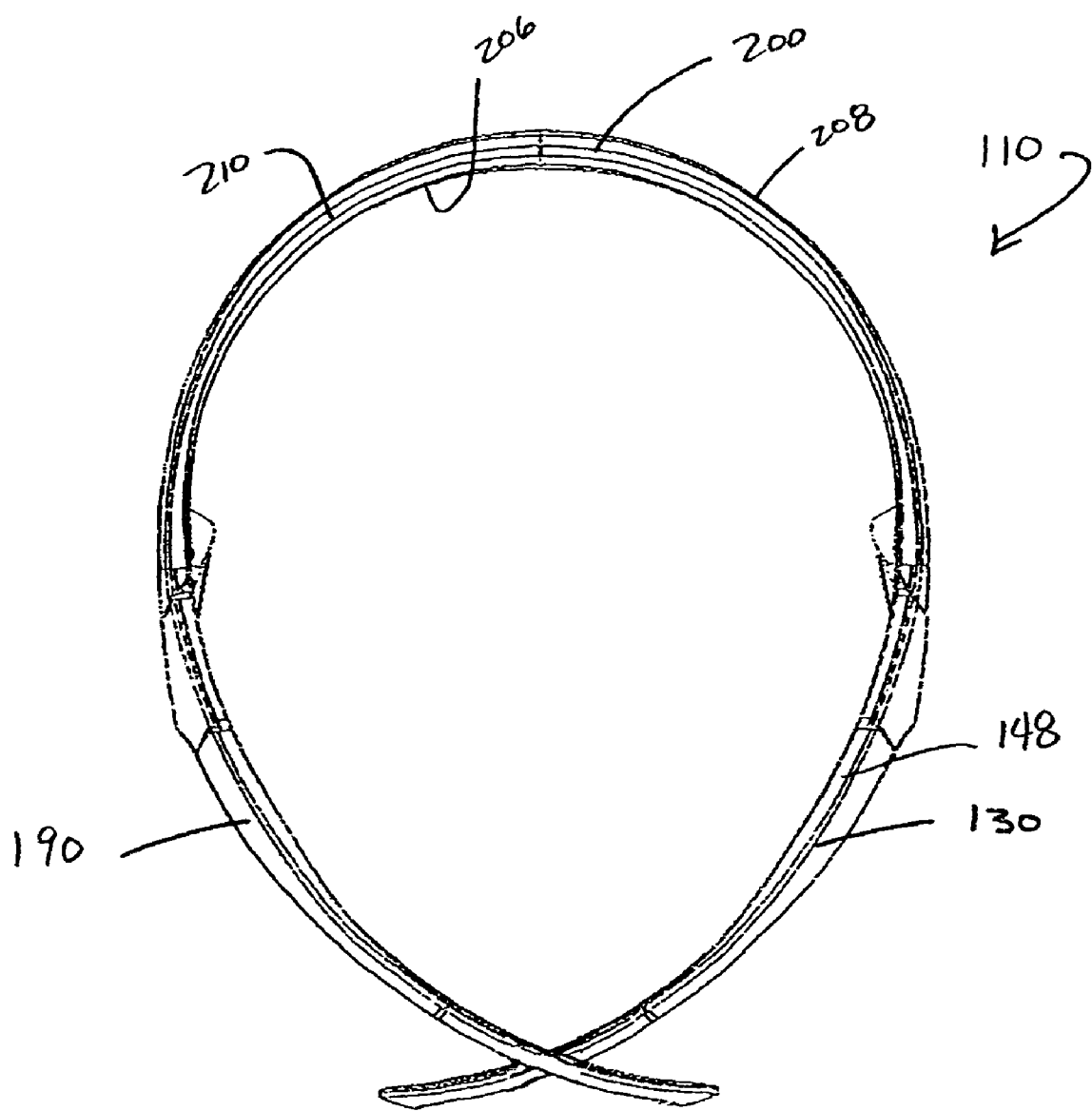
FIG. 5 is a top view of the frame of the ear warmer illustrated in FIG. 2.
Figure 6:
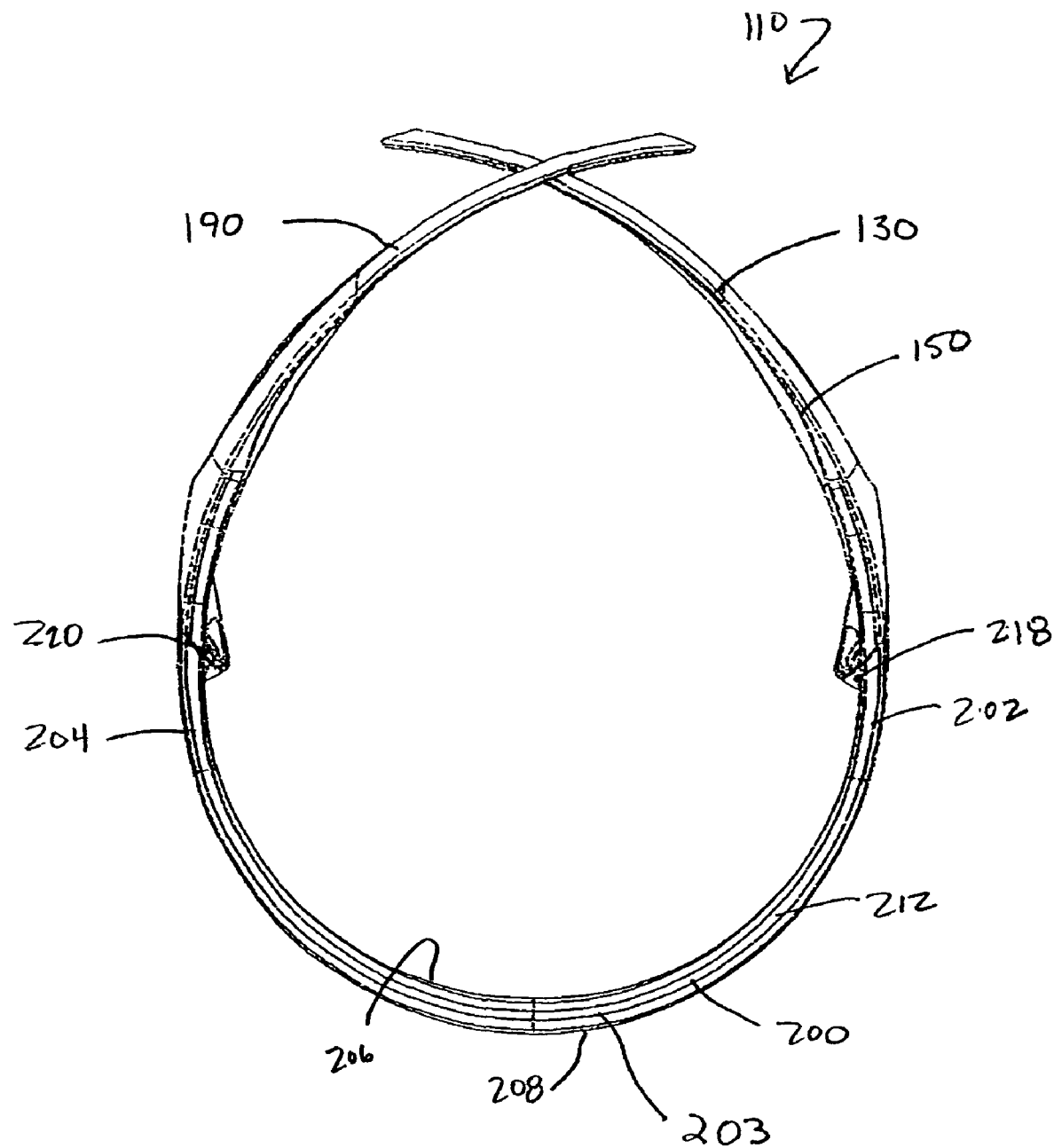
FIG. 6 is a bottom view of the frame of the ear warmer illustrated in FIG. 2.
Figure 7:
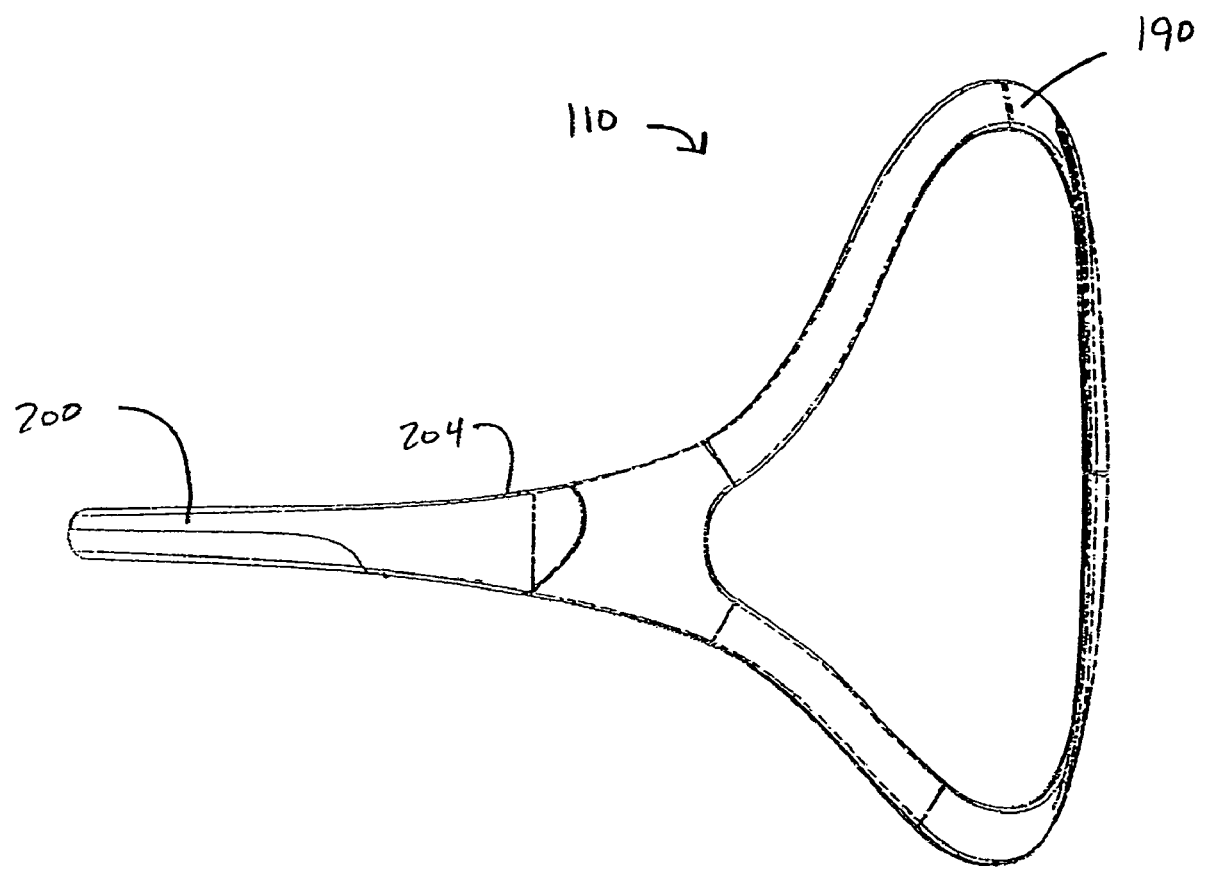
FIG. 7 is a right side view of the frame of the ear warmer illustrated in FIG. 2.
Figure 8:
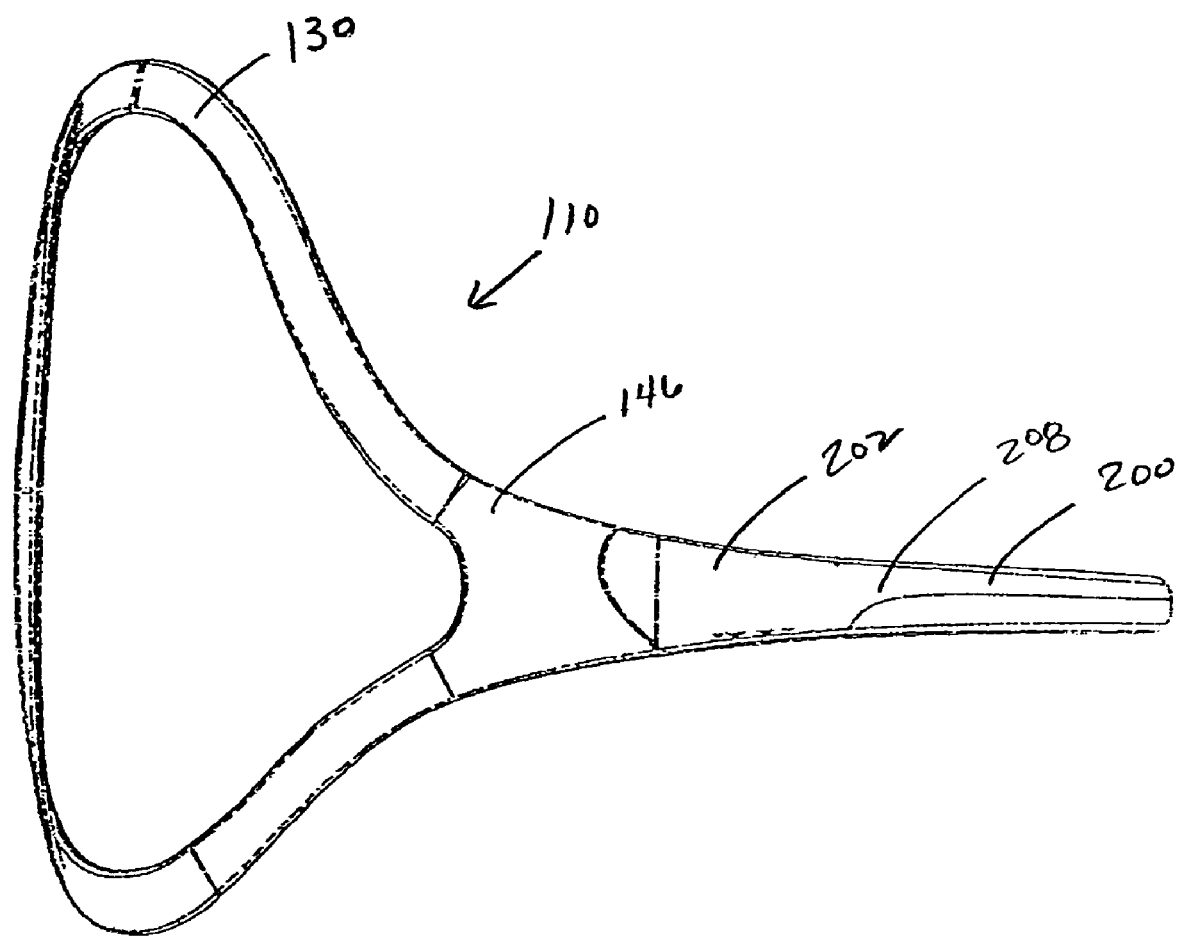
FIG. 8 is left side view of the frame of the ear warmer illustrated in FIG. 2.
Figure 9:
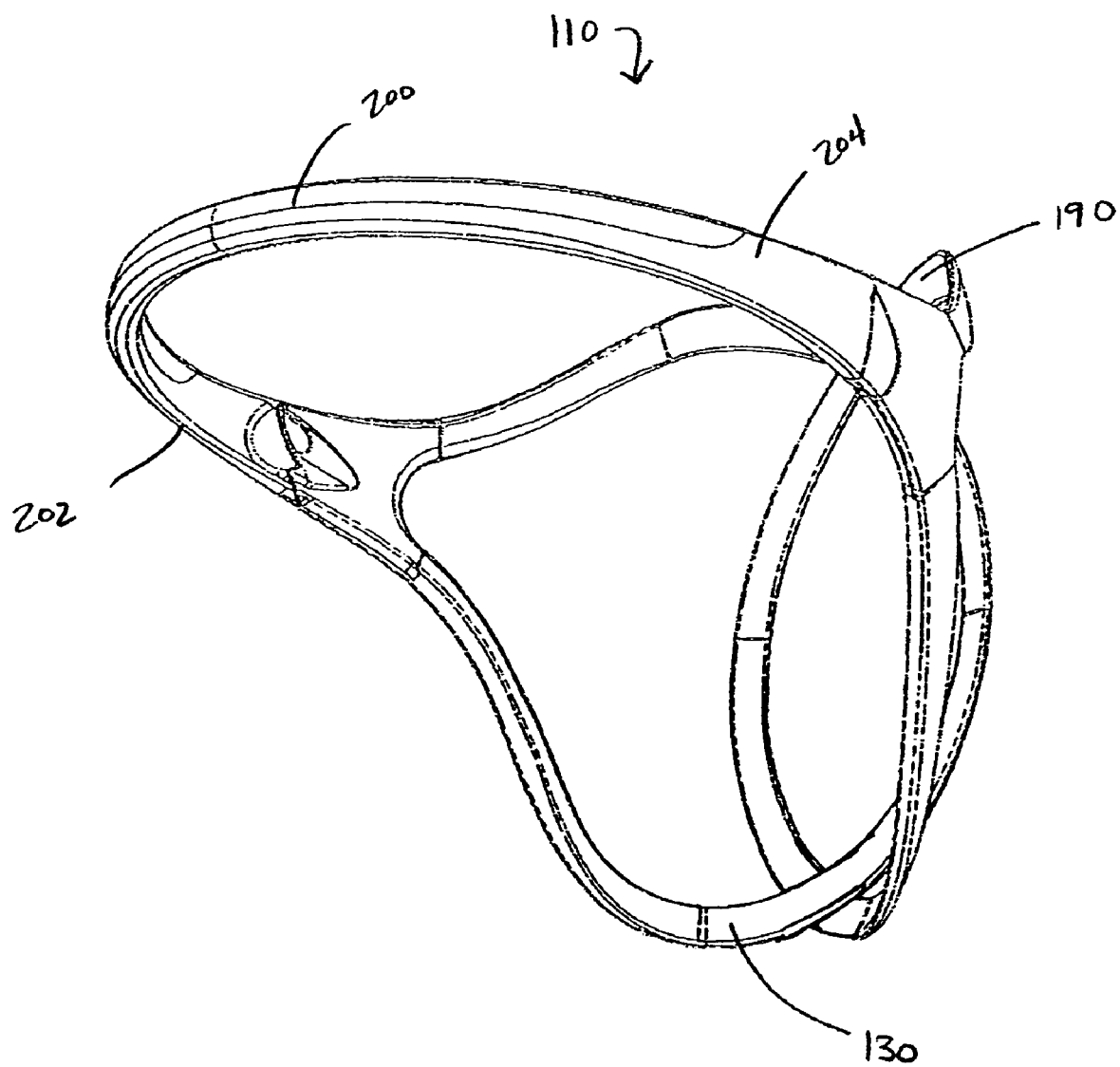
FIG. 9 is a rear perspective view of the frame of the ear warmer illustrated in FIG. 2.

In one embodiment the band portion 200 varies in a height dimension and has a substantially tapered shape (see FIG. 4). As illustrated in FIG. 4, the middle portion 203 of the band portion 200 is of a lesser height or thickness than either of the first end portion 202 of the band portion 200 and the second end portion 204 of the band portion 200. In an alternative embodiment, the band portion 200 has a constant height or thickness.

Referring to FIGS. 17-21, the first end portion 202 of the band portion 200 includes a first coupling portion 218 configured to be coupled to the first ear portion 130 of the frame 110. Similarly, the second end portion 204 of the band portion 200 includes a second coupling portion 220 configured to be coupled to the second ear portion 190 of the frame 110. In this embodiment, the first coupling portion 218 and the second coupling portion 220 are substantially similar in function and structure with the exception that they are reverse images of each other. Therefore, only the first coupling portion 218 of the band member 200 will be discussed in detail. In alternative embodiments, the coupling portions may have different configurations and/or structures.

Figure 17:
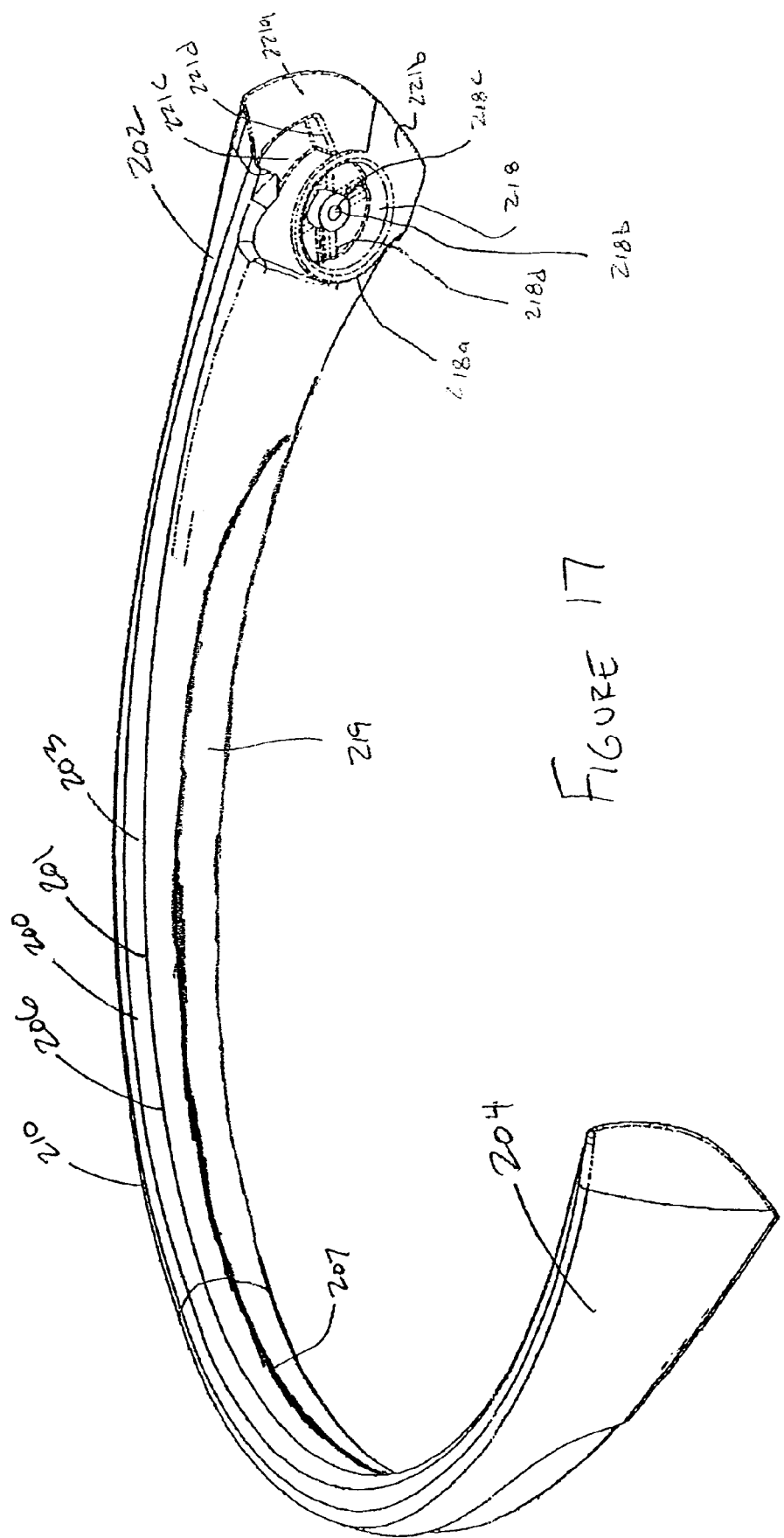
FIG. 17 is a perspective view of a band portion of the frame of the ear warmer illustrated in FIG. 2.
Figure 18:
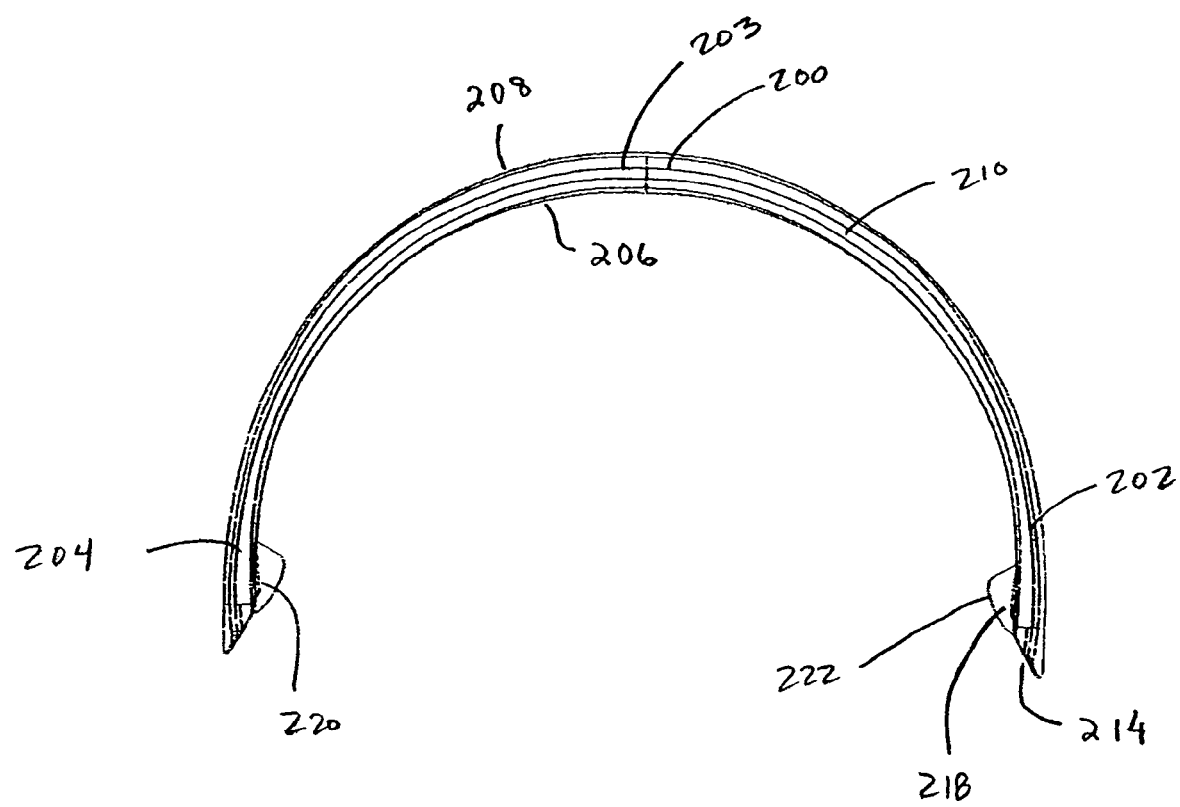
FIG. 18 is a top view of the band portion illustrated in FIG. 17.

As illustrated in FIGS. 17 and 18, the first coupling portion 218 includes an end surface 214 of the band portion 200 and includes distal end 222. The distal end 222 of the first coupling portion 218 has a mounting structure and defines a planar surface (also referred to herein as the "oblique plane"). Although in one embodiment the mounting structure is cylindrical in shape, the mounting structure need not be cylindrical in shape. The coupling portion and mounting structure may be of any shape, such as cubic or rectangular.

Figure 19:
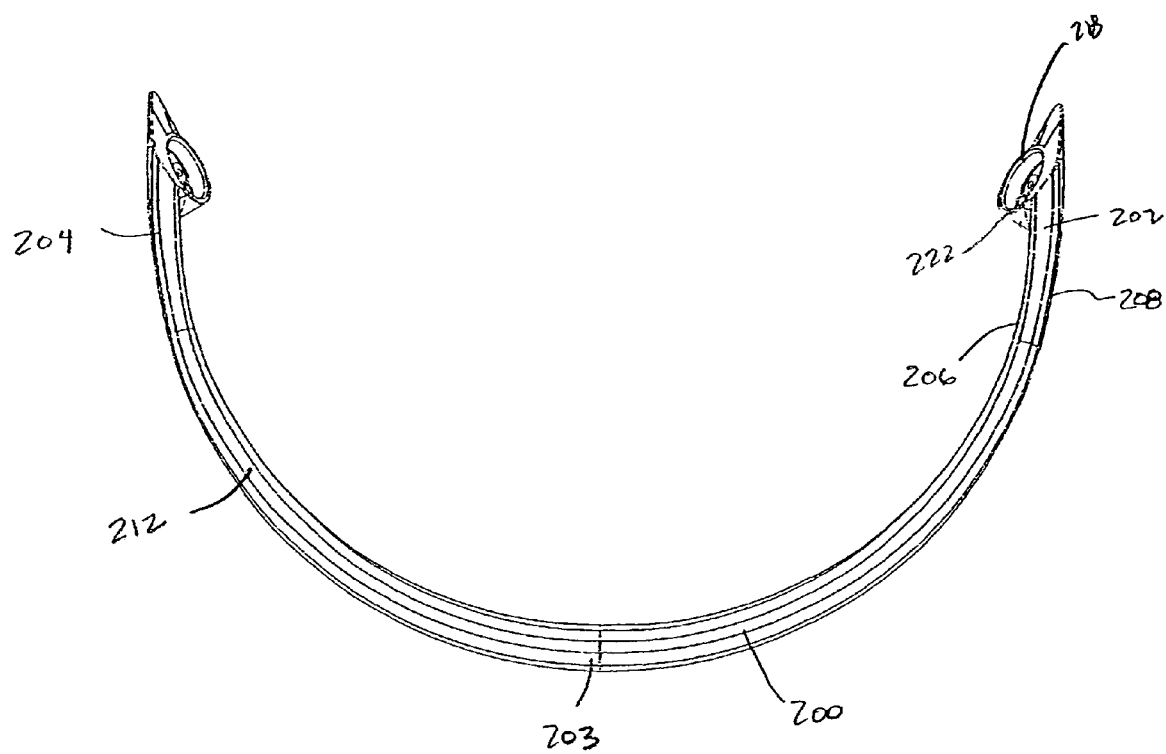
FIG. 19 is a bottom view of the band portion illustrated in FIG. 17.
Figure 20:
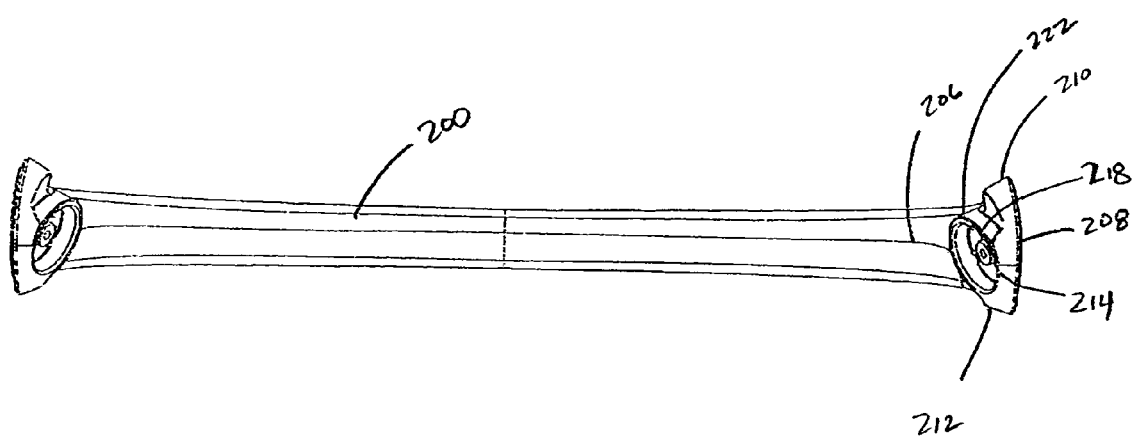
FIG. 20 is a front view of the band portion illustrated in FIG. 17.

Referring to FIG. 20, the oblique plane is oblique to the surfaces defined by the upper side 210 and lower side 212 of the band portion 200. Additionally, as illustrated in FIG. 19, the oblique plane is oblique to the surfaces defined by the inner side 206 proximate the coupling portion 218 and the outer side 208 of the band portion 200 proximate the coupling portion 218.

In one embodiment, the oblique plane enables the ear portion to move upwardly and inwardly to a collapsed configuration as described below. In an alternative embodiment, the end surface of the band portion is at an oblique plane with respect to only one side of the band portion. Alternatively, the end surface of the band portion can be substantially perpendicular to the outer surface of the band portion.

In one embodiment, the frame, including the band portion and the ear portions, is made of a single material. In another embodiment, the frame is made of polypropylene. In alternative embodiments, the frame is made of a thermoplastic resin material, such as Crastin® sold by DuPont, or Grillamid®.

In an alternative embodiment, the band portion 200 includes a recess 207 (see FIG. 17). In this embodiment, the band portion 200 is made of a first material 201 and a second material 219 (see FIG. 17). The second material 219 may be any material that increases friction contact. Also, the second material 219 can be any material that can distribute the force of the ear warmer 100 when retained on the user. In the embodiment shown in FIG. 17, the second material extends for less than the entire height of the band portion. In alternative embodiments, the second material can be on the inside of the band portion only, the inside and outside of the band portion, or the outside of the band portion only. Alternatively, the second material can be disposed in two or more separate locations on the band portion. In an alternative embodiment, the second material extends across an entire width of the band portion. In one embodiment, the first material 201 is a plastic material and the second material 219 is a rubber material. Although the band portion of the frame is illustrated as being elongated, the band portion need not be elongated in shape.

Referring to FIG. 17, the coupling portion 218 is illustrated and described in detail. In this embodiment, the coupling portions 218 and 220 are substantially the same. Accordingly, only coupling portion 218 is described in detail. It is to be understood that alternative embodiments of the band portion to not necessarily need to have all of the features and/or structures discussed with respect to coupling portion 218. In other words, alternative coupling portions can have any combination of the structures.

Referring to FIG. 17, the coupling portion 218 includes a mounting structure 218a that in substantially cylindrical in shape. The mounting structure 218a has a lower surface that can include one or more recesses or notches 218d, the function of which is described later. The mounting structure 218a also includes a center shoulder 218b that has an opening 218c that is configured to receive a connector, such as a screw.

In one embodiment, the end of the band portion 200 includes a first end surface 221a and a second end surface 221b that is proximate to surface 221a. The surfaces 221a and 221b are offset and at an angle with respect to each other. The configuration of surfaces 221a and 221b assist with the movement of the ear portion with respect to the band portion. In an alternative embodiment, surfaces 221a and 221b are disposed in the same plane. As described below, surfaces 221a and 221b form contact surfaces that limit the rotation of the ear portion relative to the band. The end of the band portion 200 also includes another surface 221a and a shoulder 221d adjacent surface 221c. The surface 221c and shoulder 221d form an abutment that is contacted by the ear portion to limit the rotation of the ear portion with respect to the band portion 200. In an alternative embodiment, the band portion does not include a surface and shoulder as previously described.

In one embodiment, the band portion includes a coupler that is configured to removably couple a label, such as a brand label, to the band portion. In one embodiment, the coupler is disposed at the rear of the band portion. In alternative embodiments, the coupler is disposed on a side of the band portion, for example near the portion of the band, which couples to the ear portion, or at any other location on the band portion.

Figure 21:
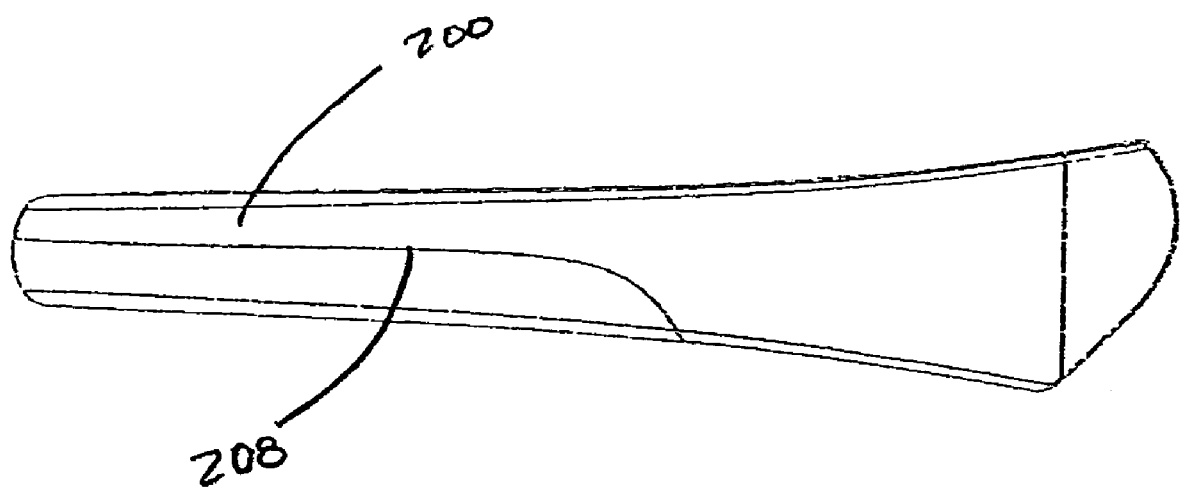
FIG. 21 is a side view of the band portion illustrated in FIG. 17.
Figure 21B:
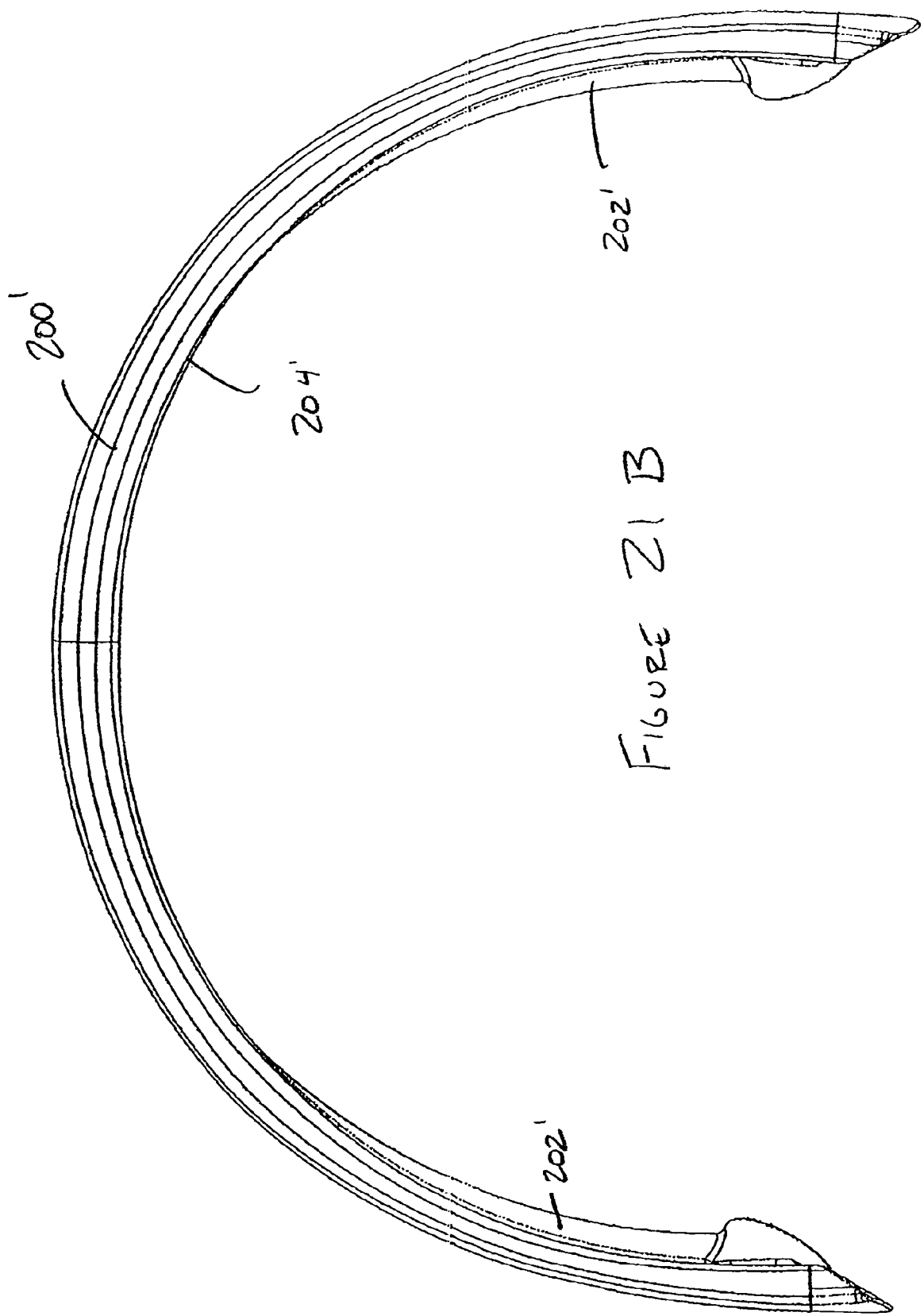
FIG. 21B is a top view of an alternative embodiment of a band portion of a frame according to an embodiment of the invention.

An alternative embodiment of the band portion is illustrated in FIGS. 21A and 21B. In this embodiment, a band portion 200' includes support members 202' disposed on the inner surface 204' of the band portion 200'. Support members 202' are configured to provide added strength and support to the band portion 200'.

An embodiment of an ear portion is illustrated in FIGS. 13-16. In this embodiment, the first ear portion 130 of the frame 110 and the second ear portion 190 of the frame 110 are substantially similar in function and structure. Therefore, only the first ear portion 130 is discussed in detail.

As illustrated in FIGS. 13 through 16, the first ear portion 130 of the frame 110 defines an opening 134 and a center point 152. The first ear portion 130 includes a proximal end portion 156, which includes a proximal end point 136 (the portion and point being proximate to the coupling of the first ear portion 130 and the band portion 200); a distal end portion 158, which includes a distal end point 138 (the portion and point being distal from the coupling of the first end portion 130 and the band portion 200); an uppermost portion 160, which includes an uppermost point 140 (the portion and point being uppermost when the ear warmer is disposed in an expanded configuration on a user); and a lowermost portion 162, which includes a lowermost point 142 (the portion and point being lowermost when the ear warmer is disposed in an expanded configuration on a user).

Although points on the first ear portion 130 have been identified as being proximal, distal, uppermost, and lowermost, it should be understood that there may be, for example, several uppermost points of the first ear portion. In such a case, the "uppermost point" includes the several points. The same is true for the proximal, distal, and lowermost points. In addition, the terms proximal, distal, uppermost, and lowermost are used for convenient reference with respect to the orientation shown in FIGS. 2 through 9 and 13 through 16. It should be understood that these locations of the frame are still applicable regardless of the orientation of the frame at any given time.

Figure 13:
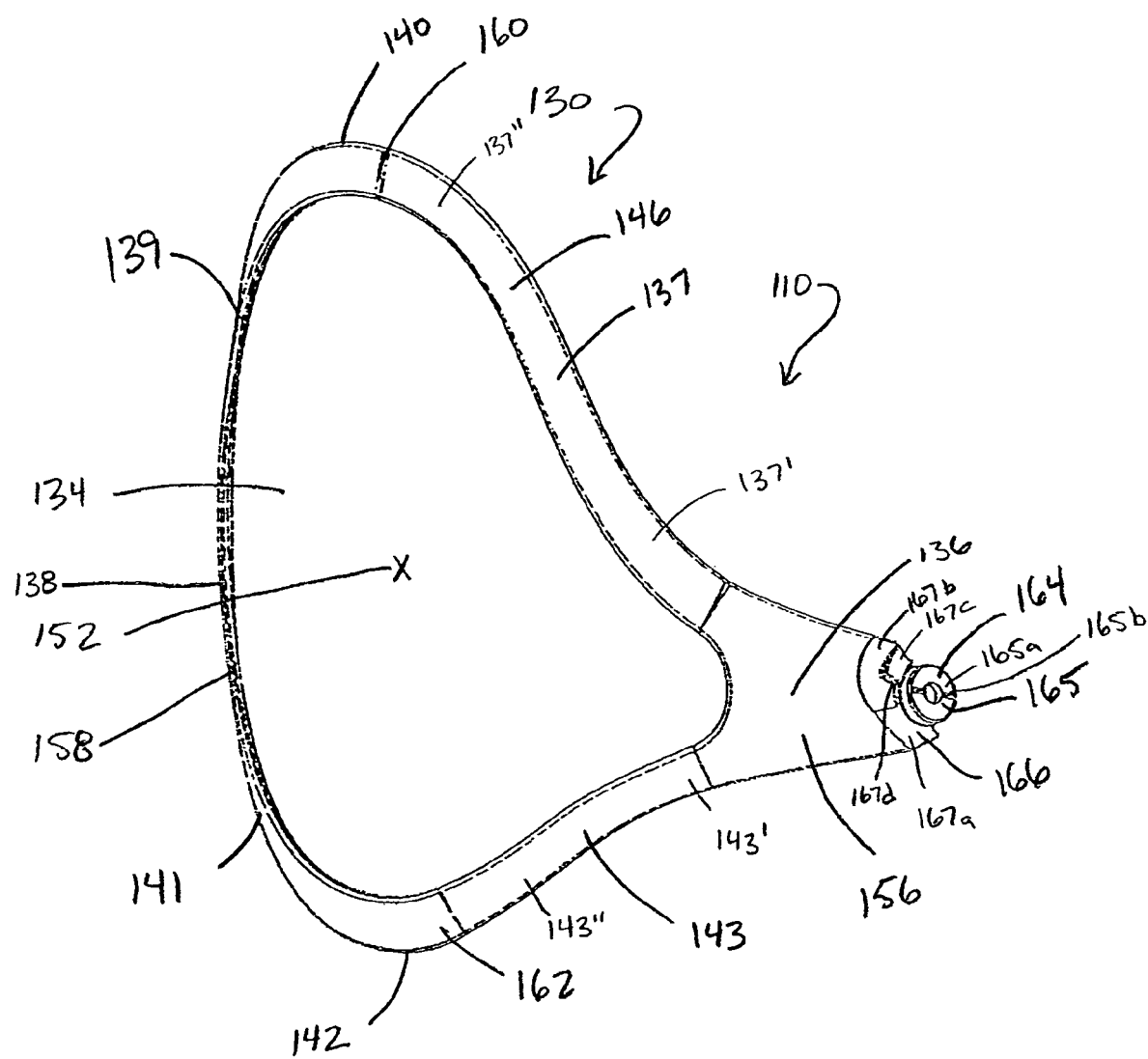
FIG. 13 is a perspective view of an ear portion of the frame of the ear warmer illustrated in FIG. 2.
Figure 15:
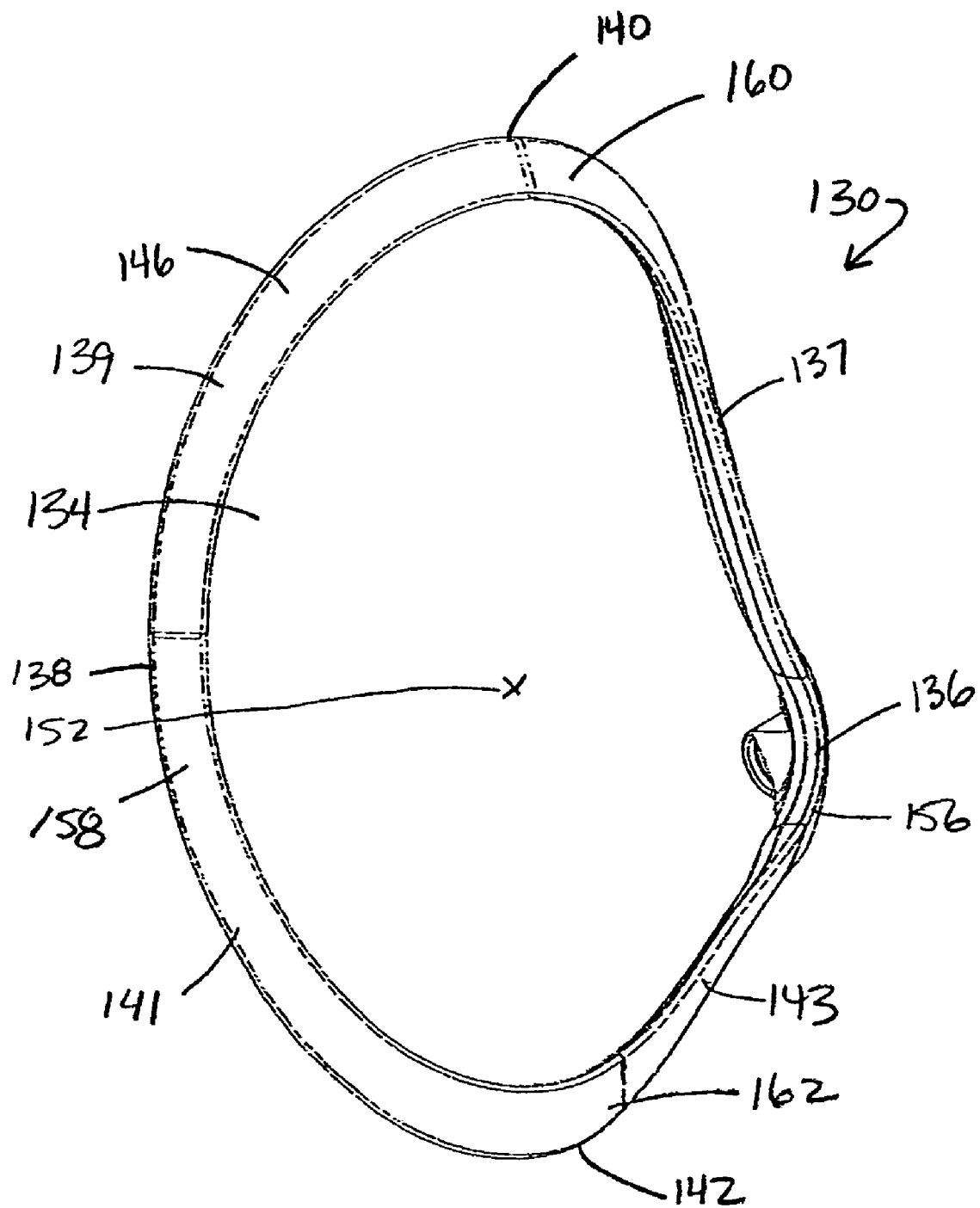
FIG. 15 is a front view of the ear portion illustrated in FIG. 13.
Figure 16:
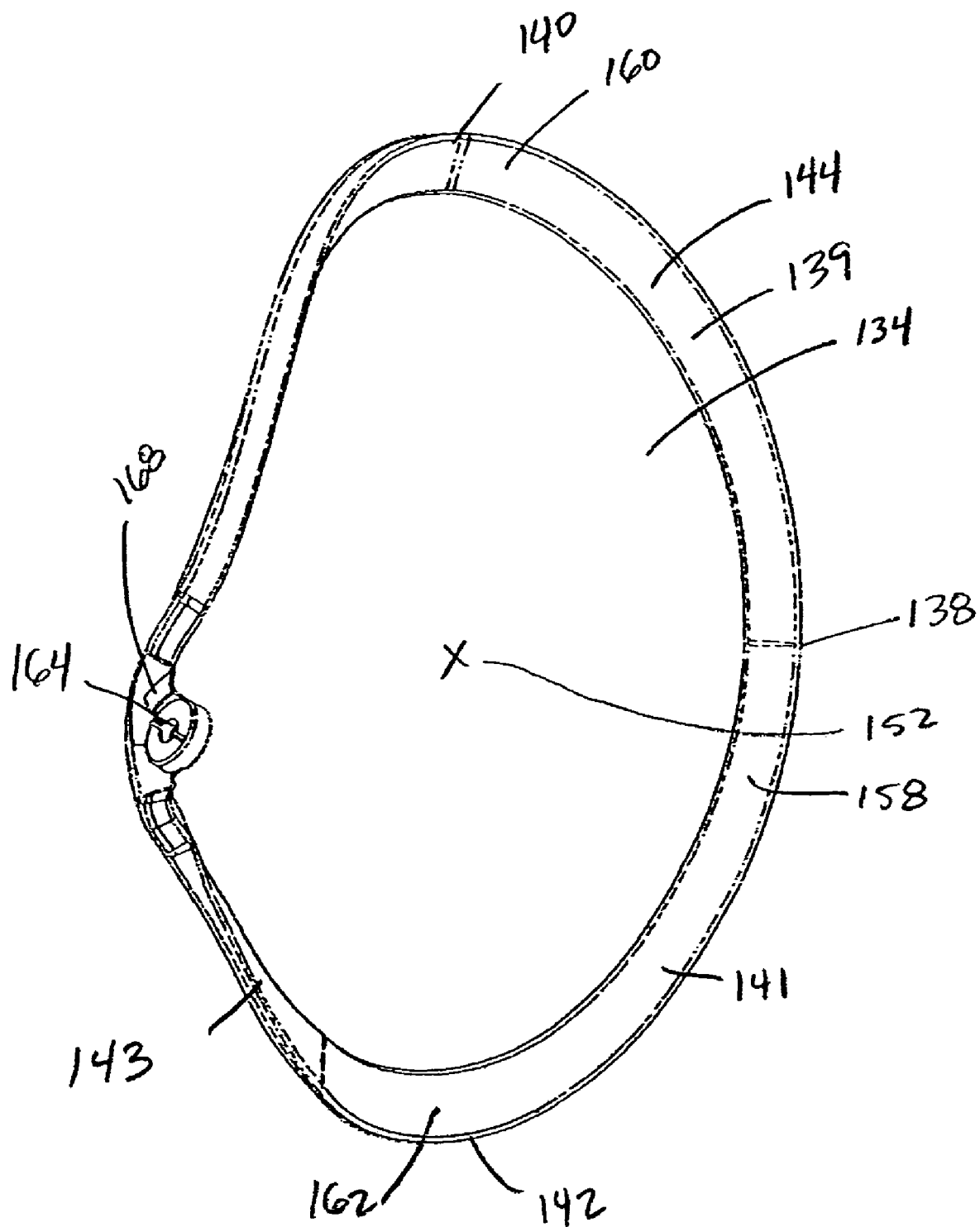
FIG. 16 is a rear view of the ear portion illustrated in FIG. 13.

As illustrated in FIGS. 13 and 15, a portion 137 of the first ear portion 130 of the frame 110 is disposed between the proximal end point 136 and the uppermost point 140 and has a first part 137' and a second part 137". From a side view of the first ear portion 130 (see FIG. 13), the first part 137' of the portion 137 has a convex configuration with respect to the center point 152. Similarly, a portion 143 of the first ear portion 130 of the frame 110 is disposed between the lowermost point 142 and the proximal end point 136. The portion 143 has a first part 143' and a second part 143". From a side view, the first part 143' of the portion 143 has a convex configuration with respect to the center point 152. In other words, at least a portion of each of the portions 137 and 143 of the first ear portion 130 bend or curve away from the center point 152. The location and number of inflection points in portions 137 and 143 can vary along the ear portion.

From a side view of the first ear portion 130, the portion 139 of the first ear portion 130 of the frame 110 that is disposed between the uppermost point 140 and the distal end point 138 has a concave configuration with respect to the center point 152. Similarly, the portion 141 of the first ear portion 130 of the frame 110 that is disposed between the distal end point 138 and the lowermost point 142 has a concave configuration with respect to the center point 152. In other words, at least a portion of each of the portions 139 and 141 of the first ear portion 130 bend toward the center point 152. In alternative embodiments one or both of the portions 139 and 141 can include a concave portion or section and a convex portion or section, relative to the center point.

Figure 14:
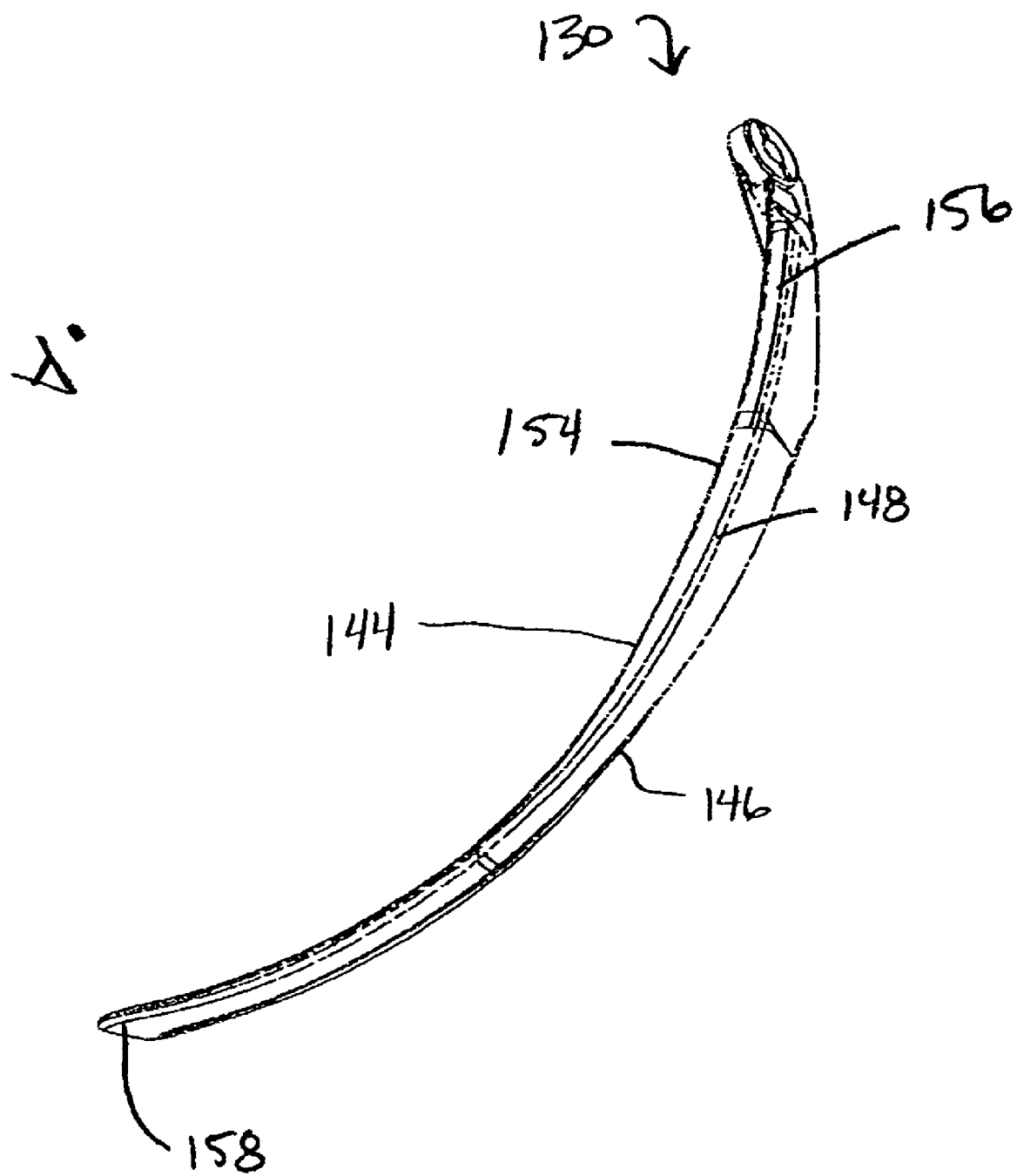
FIG. 14 is a top view of the ear portion illustrated in FIG. 13.

Referring to FIG. 14, the first ear portion 130 includes an inner side 144 (the side that is disposed adjacent a user when the ear warmer is worn by the user), an outer side 146 (the side opposite the inner side and distal from a user when the ear warmer is worn by the user), an upper side 148 (the side that faces up when the ear warmer is worn by a user), and a lower side 150 (see FIG. 13) (the side that faces down when the ear warmer is worn by a user). The inner side 144 of the first ear portion 130 defines an interior portion or region of the opening 134. Similarly, the outer side 146 of the first ear portion 130 defines an exterior portion or region of the opening 134.

As illustrated in FIG. 14, the inner side 144 of the first ear portion 130 of the frame 110 has an innermost surface 154. The innermost surface 154 is the portion of the inner side 144 of the first ear portion 130 directly adjacent a user's head when the ear warmer 100 is worn by the user. Referring to FIG. 14, a top view of a two-dimensional projection of the innermost surface 154 is a curved line that curves around a point A, which is disposed on the inner side of the first ear portion 130. In other words, the first ear portion 130 is curved such the distal end portion 158 is configured to be disposed closer to a user's head, or to place more pressure on the user's head (if the entire portion of the frame is contacting the user's head), than a mid-point of the innermost surface 154 when the ear warmer 100 is worn by the user. This is due to the fact that the curvature of the user's head may be different from the curvature of the ear portion. Said another way, the frame 110 is configured to apply lateral forces to the user's head inwardly where the forces are greatest at the distal end portion 158.

In one embodiment, the distal end portion 158 of the frame 110 is flexible. Thus, the lateral force of the distal end portion 158 against a user's head causes the distal end portion to bend or flex and, thus, to better fit along the user's head. In an alternative embodiment, the first ear portion is curved such that the distal end portion of the first ear portion is configured to be disposed closer to a user's head than the proximal end portion of the first ear portion when the ear warmer is worn by the user. In a further alternative embodiment, the portion of the innermost surface disposed between the proximal end portion and the distal end portion does not have a curved shape.

Figure 14A:
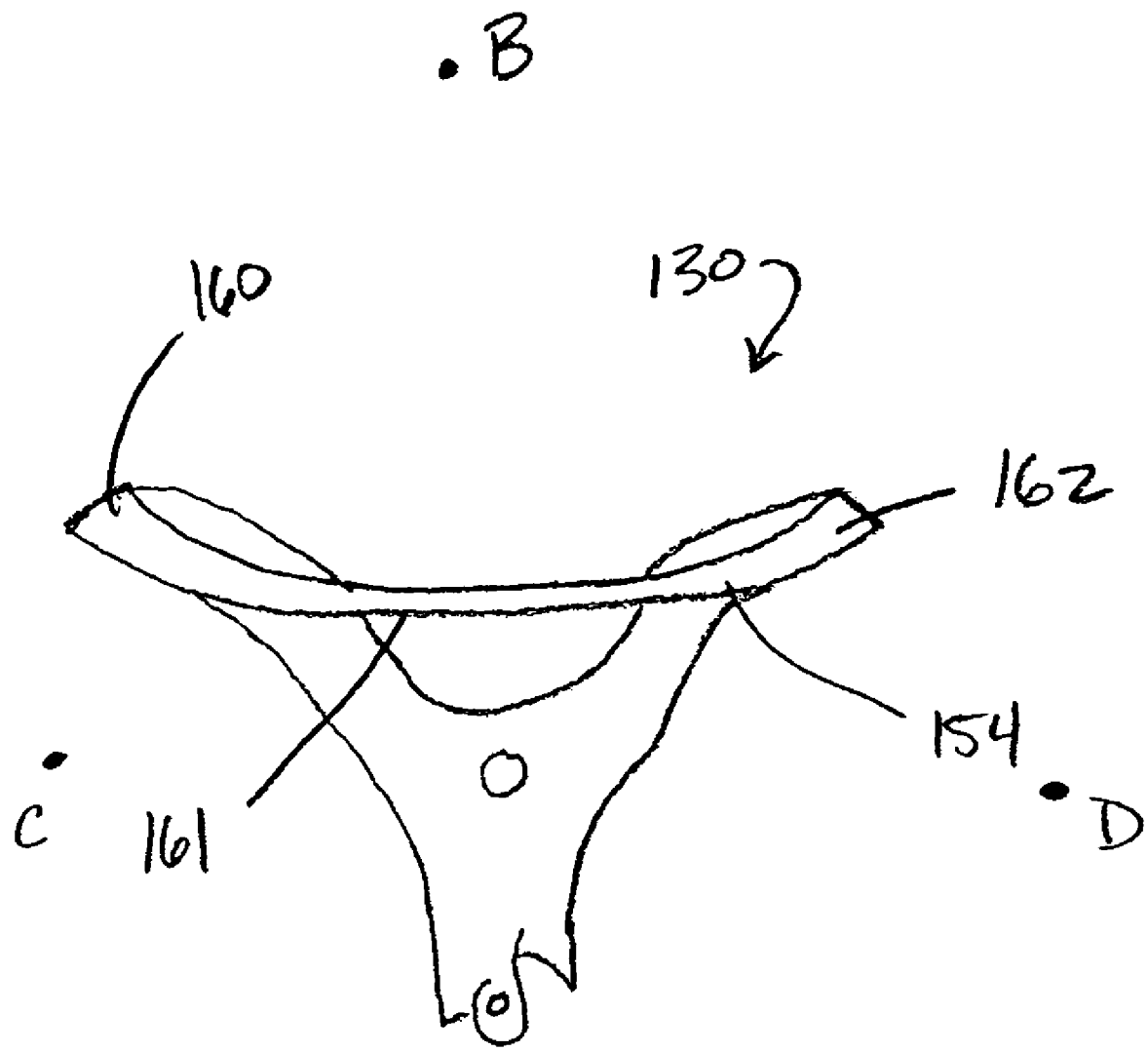
FIG. 14A is a front perspective view of the ear portion illustrated in FIG. 13.

As illustrated in FIG. 14a, a two-dimensional projection of a front view of the innermost surface 154 is a curved line that has three radii of curvature. Specifically, the two-dimensional projection has a first part that bends or curves around point B, a second part that bends or curves around part C, and a third part that bends or curves around point D.

In the illustrated embodiment, the distal end portion 138 is curved such that a center portion of the distal end portion 138 is configured to be disposed closer to a user's head than the remaining portions of the distal end portion 138 when the ear warmer is worn by a user. In an alternative embodiment, the uppermost portion is configured to be disposed closer to the user's head than the lowermost portion when the ear warmer is worn by the user. In a further alternative embodiment, the first ear portion is curved such that the lowermost portion is configured to be disposed closer to the user's head than the uppermost portion when the ear warmer is worn by the user.

Although the first ear portion 130 is described and illustrated as having a particular shape, in other embodiments, the first ear portion has different shapes. Additionally, in one embodiment, the first ear portion is made of a plastic material. In an alternative embodiment, the first ear portion is made of another material, such as a metal.

The first ear portion 130 has an abutting and complimentary fit with the band portion 200. More specifically, returning to FIG. 13, the first ear portion 130 includes coupling portion 164 that extends from an end surface 166 of the first ear portion 130. The coupling portion 164 includes a distal end 165 that defines a surface 165a. In one embodiment, the surface 165a includes one or more ridges or protrusions 165b that engage the recesses 218d as the ear portion rotates. The coupling portion 164 is received in structure 218a. In one embodiment, the end portion of the first ear portion 130 includes surfaces 167a and 167b that compliment and engage surfaces 221a and 221b on the band portion 200 when the ear portion 130 is in its collapsed configuration. The end portion also includes a protrusion 167c with a contact surface 167d that engages the surface 221c and shoulder 221d to form a secondary stop to limit the rotation of the ear portion. In alternative embodiments, the ear portion does not include protrusion 167c and band portion 200 does not include the surface 221c and shoulder 221d. As illustrated in FIG. 20, the surface defined by the distal end 222 of the coupling portion 218 of the band portion 200 abuts the surface defined by the distal end 165 of the coupling portion 164. Also, the end surface 214 of the band portion 200 of the frame 10 abuts the end surface 166 of the first end portion 130. In other words, the band portion 200 abuts the first ear portion 130 and has surfaces, including the surface defined by the distal end 222 of the coupling portion 218 and the end surface 214 of the band portion 200, that fit complimentary to surfaces of the first end portion 130, including the surface defined by the distal end 165 of the coupling portion 164 and the end surface 166 of the first ear portion 130, when the first ear portion 130 is in its collapsed configuration.

Because of abutting and complimentary fit of the band portion 200 and the first ear portion 130, the transition between the outer surface 208 of the band portion 200 and the outer surface 146 of the first ear portion 130 is a smooth transition or a substantially smooth transition. In other words, the outer surface 208 of the band portion 200 and the outer surface 146 of the first ear portion 130 form a substantially continuous surface when the ear warmer is in the expanded configuration. With the exception of the inner surface, the same is true for the remaining surfaces of the band portion 200 and the first ear portion 130. Specifically, the upper surface 210 of the band portion 200 and the upper surface 148 of the first ear portion 130 form a substantially continuous surface. The lower surface 212 of the band portion 200 and the lower surface 150 of the first ear portion 130 form a substantially continuous surface.

In one embodiment, the coupling portions of the ear portion and the band portion is located on the inner surface. In an alternative embodiment, the inner surface of the ear portion and the inner surface of the band portion form a substantially continuous surface. Alternatively, the coupling portions of the band portion and the ear portion are located at different locations.

The substantially continuous surface formed by the upper surface 210 of the band portion 200 and the upper surface 148 of the first ear portion 130 extends from the first ear portion 130 to the second ear portion 190. The substantially continuous surfaces formed by the lower, upper, and inner surfaces of the band portion 210 and the first ear portion 130 also extend to the respective surfaces of the second ear portion. Thus, the upper surface of the ear warmer 100, the lower surface of the ear warmer 100, and the outer surface of the ear warmer 100 collectively form a smooth contour. In alternative embodiments any combination of the corresponding surface, outer surface, upper surface and lower surface of any of the frame components can form a substantially continuous surface.

In one embodiment, a screw (not illustrated) is used to pivotally couple the first ear portion 130 to the band portion 210. A first end of the screw extends from the inner side 144 of the first ear portion 130 and a second end of the screw is disposed within the band portion 200 and is not outwardly visible. In other words, only a single end of the screw is exposed (i.e., disposed outside of the frame 110 of the ear warmer 100). In alternative embodiments, a rivet, a pin, a brad, or any other coupling device is used to pivotally couple the ear portions 130 and 190 to the band portion 200.

FIGS. 10 though 12 illustrate the frame 110 of the ear warmer 100 in a collapsed configuration. The first ear portion 130 and the second ear portion 190 are disposed adjacent to and substantially within the same plane as the band portion 200 when the frame 110 is in its collapsed configuration. The coupling arrangement between the band portion 200 and the ear portions (as described in detail above) allow the ear portions 130 and 190 to pivot into and out of the collapsed configuration. As illustrated in FIG. 12, the ear warmer 100 has a low profile when in its collapsed configuration. In one embodiment, the oblique plane defined by the band portion 200 allows the ear portion 130 and 190 to move in a way that contributes to this overall low profile. For example, the oblique plane allows the ear portions to rotate about the pivot connection while being substantially within or proximate the same plane as the band portion 200.

Ear warmer 100 is configured to allow a predetermined range of motion between the expanded configuration and the collapsed configuration. In one embodiment, this range of motion does not include movement from the expanded configuration to a different collapsed configuration, for example, where the ear portions of the frame are disposed on a side of the band opposite from their position in the collapsed configuration within the range of motion. In one embodiment, two different mechanisms each produce a respective stop that defines a respective end point of the range of motion (as discussed below).

In an alternative embodiment, the ear portions can rotate continuously and are not limited to a particular range. Alternatively, the ear portions can be slidably coupled to the band portion, or can rotate about another axis than that described above.

As illustrated in FIGS. 22 and 23, it is not necessary that the frame be separate items. In FIGS. 22 and 23, the frames 270 and 280, respectively, are of a unitary or monolithic structure. In these embodiments, the band portions 272 and 286, respectively, do not have adjustable lengths. In a further alternative embodiment, the band portion is an adjustable band. In yet a further alternative embodiment, the band portion of the frame includes several different and separate items.

Figure 24:
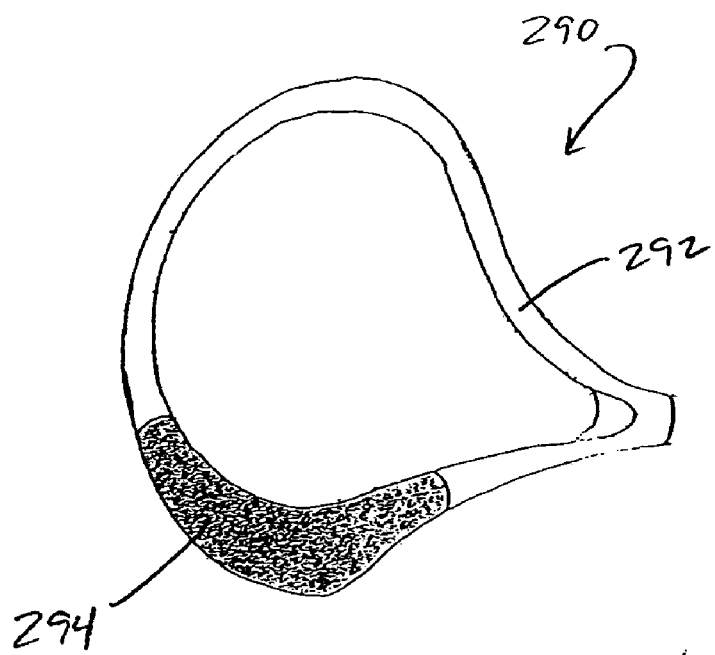
FIG. 24 is a side view of an ear portion according to another embodiment of the invention.
Figure 25:
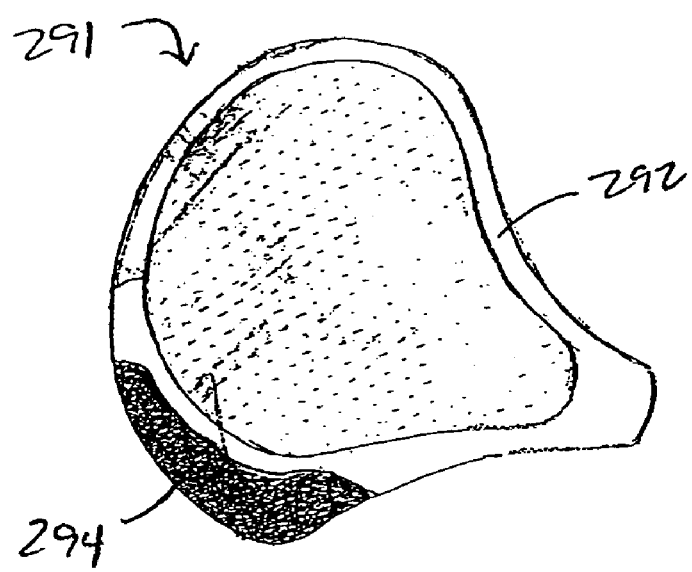
FIG. 25 is a side view of an ear portion according to another embodiment of the invention.

Alternative embodiments of ear portions are illustrated in FIGS. 24 and 25. In these embodiments, the ear portions may be formed of a first material and a second material that is different than the first material. In FIGS. 24 and 25, the ear portions 290 and 291, respectively, are made of a first material 292 and a second material 294. For example, the first material 292 may be any type of plastic and the second material 294 may be any type of resilient material, such as rubber. The resilient material 294 provides for an increased gripping surface for contact with the user or other article. The resilient material 294 also increases the distribution of the application of clamping or gripping force of the ear warmer on the user's head. In FIG. 24, the second material extends an entire width of a portion of the ear portion 290, whereas in FIG. 25, the second material only extends across a portion of width of a portion of the ear portion 292.

In alternative embodiments, the recess or opening in the ear portion in which the second material is disposed can have any size or configuration. The location of the recess or opening for the second material can vary along the ear portion. As previously discussed, the band portion of an ear warmer can also include a portion of a first material and a portion of a second material that is different from the first material. In an alternative embodiment, the ear portion and/or band portion can include several raised bumps formed on one of its surfaces. The raised bumps can be located on the first material and/or the second material if the ear portion includes two different materials.

As illustrated in FIG. 1, the ear warmer 100 includes fabric members 230 and 250. The fabric members 230 and 250 are coupled to the frame 110 of the ear warmer 100. The fabric members 230 and 250 are configured to substantially cover at least a portion of the ear portions 130 and 190 of the ear warmer 100. Various configurations of the fabric members are described below.

FIG. 26 shows a side view of a portion of an ear warmer according to an embodiment of the invention. In this embodiment, the frame 310 includes an ear portion 330. A fabric member 350 is fixedly coupled to the ear portion 330 of the frame 310. For example, the fabric member 350 can be fixedly coupled to the ear portion 330 of the frame 310 by any technique or method, including radio frequency (RF) welding, ultrasonic welding, or an adhesive such as glue. For example, the perimeter portion 352 of the fabric member 350 can be fixedly coupled to or proximate to the perimeter portion 332 of the ear portion 330 of the frame 310. The term "perimeter portion" is intended herein to include the perimeter or a portion offset from and proximate to the perimeter of a membrane, member or portion. Following the example shown in FIG. 26, a weld, adhesive or connector can be located along the actual perimeter of the fabric member 350 and a portion of the ear portion 330 of the frame 310 offset from and proximate to the perimeter of the ear portion 330.

In another embodiment, the fabric member includes binding coupled along at least a portion of the perimeter of the fabric member. In such an embodiment, the binding can be coupled to the frame using the techniques identified above. Alternatively, the fabric member can be coupled to the frame. In this embodiment, the binding provides additional support and cushioning to the user. Additionally, the binding provides a seal between the ear warmer and a user's head.

Figure 26A:
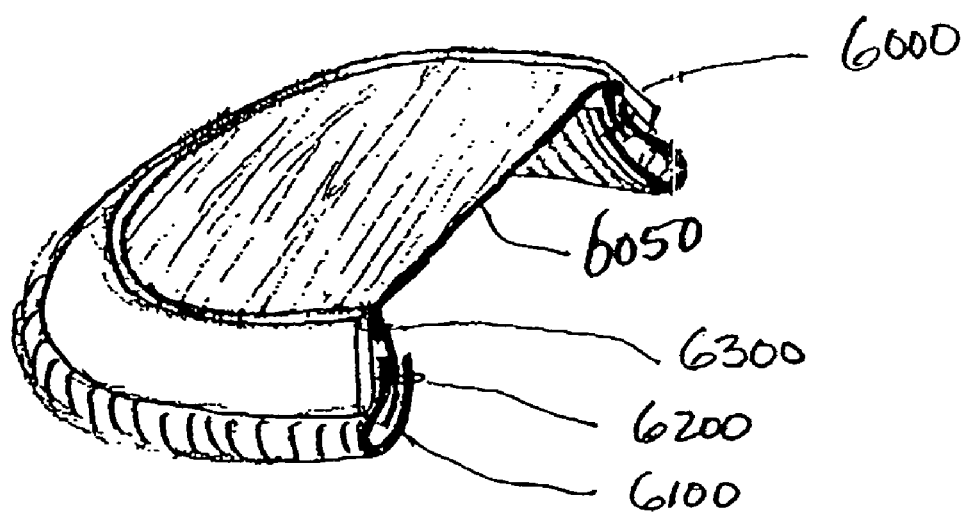
FIGS. 26A and 26B are partial cross-sectional views of an embodiment of a portion of an ear warmer according to an embodiment of the invention.
Figure 26B:

Referring to FIGS. 26A and 26B, which are partial cross-sectional views, an embodiment of an ear portion is illustrated. In this embodiment, the frame 6000, such as an ear portion, includes a fabric member 6050 coupled thereto. In one embodiment, fabric member 6050 includes a binding 6100 coupled thereto in any conventional manner. For example, the binding 6100 can be stitched or sewn to the fabric member 6050 by seam 6200. Fabric member 6050 can be coupled to the frame member 6000 using any conventional technique, including an adhesive, welding, such as RF or ultrasonic welding, or the like. In one embodiment, the binding 6100 is configured so that a portion of it is disposed adjacent to the innermost surface of the frame member 6000. The binding 6100 provides added cushioning, which provides a more comfortable fit. The binding 6100 also provides a better seal against a user's head to improve temperature control by preventing external air from entering any space between the ear portion and the user's head. In an alternative embodiment, the binding can be replaced by another piece of fabric material, a piece of foam, or any other structure that would assist with the cushioning and sealing functions above.

FIGS. 27 through 32 show examples of a fabric member that can be removably coupled to the ear portion of the frame. Although these figures show the fabric member being removably coupled to the ear portion of frame via press-fit connections, tongue-and-groove connections, clip-on connections and slide-and-lock connections, other types of the removable connections are also possible. In other words, FIGS. 27 through 32 merely provide examples of removable connections and other types of removable connections are possible.

FIGS. 27 and 28 show a side view and cross-section view along line 28-28 in FIG. 27, respectively, of a portion of an ear warmer 400 having a press-fit connection, according to an embodiment of the invention. Ear warmer 400 includes a frame 410 that has an ear portion 430. As shown in FIG. 27, the fabric member 450 can be fixedly coupled to an attachment member 460 along a portion of the perimeter of the fabric member 450. In this embodiment, the attachment member 460 can be made of, for example, plastic defining an opening 462 along its length and directed inwardly. As shown in FIG. 28, the opening 462 is configured such that the attachment member 460 forms a press fit over a portion of the perimeter 432 of the ear portion 430 of the frame 410. This configuration allows the fabric member 450 to be removably attached to the ear portion 430 of the frame 410. To fit over the outer side of the perimeter 432 of the ear portion 430 of the frame 410, the fabric member 450 can be made from an elastic material that is stretched when the fabric member 450 and attachment member 460 are coupled onto the ear portion 430 of the frame 410. Alternatively, the fabric member 450 can be larger than the ear portion 430 of the frame 410 so that the fabric member 450 can extend over the perimeter 432 of the ear portion 430 of the frame 410 when being configured onto the ear portion 430 of the frame 410.

Figure 27B:
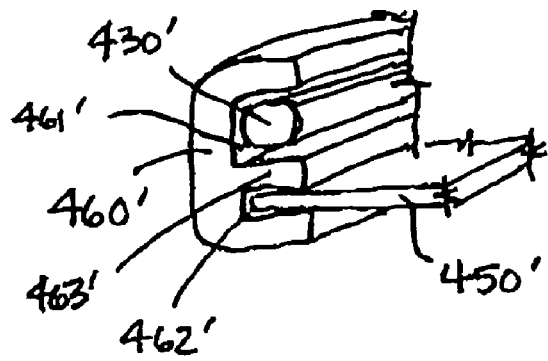
FIGS. 27A and 27B are a side view and cross-section view along line 27B-27B, respectively, of a portion of an ear warmer having a press-fit connection, according to an embodiment of the invention.
Figure 27A:
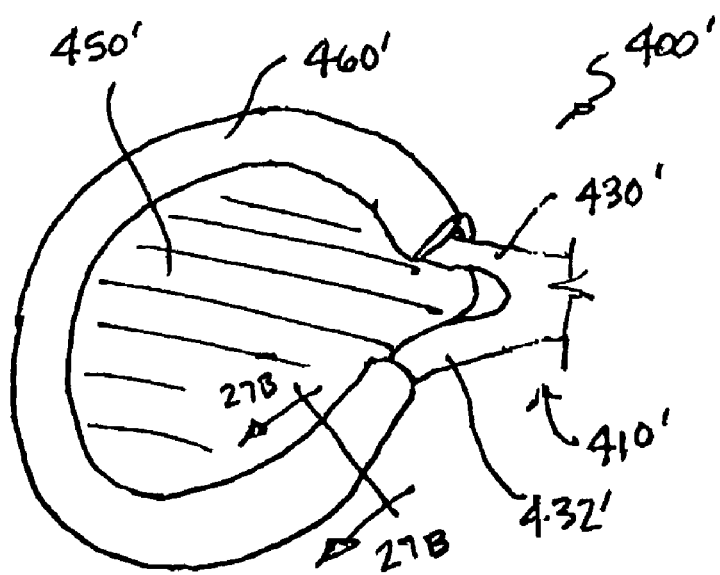

An alternative embodiment of a portion of an ear warmer 400' having a press-fit connection, according to the invention is illustrated in FIGS. 27A and 27B. Ear warmer 400' includes a frame 410' that has an ear portion 430'. As illustrated, the fabric member 450' can be fixedly coupled to an attachment member 460' along a portion of the perimeter of the fabric member 450'. In this embodiment, the attachment member 460' can be made of, for example, plastic or molded rubber. As illustrated in FIG. 27B, the attachment member 460' includes a shoulder 463' that defines openings or channels 461' and 462' along the length of the attachment member 460'. Opening 461' is configured such that the attachment member 460' forms a press fit over a portion of the perimeter 432' of the ear portion 430' of the frame 410'. This configuration allows the fabric member 450' to be removably attached to the ear portion 430' of the frame 410'. The shape of the ear portion 430' and opening 461' can vary in alternative embodiments.

To fit over the outer side of the perimeter 432' of the ear portion 430' of the frame 410', the fabric member 450' can be made from an elastic material that is stretched when the fabric member 450' and attachment member 460' are attached to the ear portion 430' of the frame 410'. Alternatively, the fabric member 450' can be larger than the ear portion 430' of the frame 410' so that the fabric member 450' can extend over the perimeter 432' of the ear portion 430' of the frame 410' when being attached to the ear portion 430' of the frame 410'.

In this embodiment, the fabric member 450' is coupled to the attachment member 460'. As illustrated in FIG. 27B, opening 462' of the attachment member 460' is configured to receive a portion of the fabric member 450'. The fabric member 450' can be fixedly coupled to the attachment member 460' by conventional coupling technique, including inserting an adhesive, such as glue, into the opening 462' to couple the fabric member 450' thereto. In an alternative embodiment, the fabric member is fused to the attachment member. In this embodiment the fabric member is inserted into the opening of the attachment member. The attachment member is then heated such that a portion of the material of the attachment member melts and is absorbed into the fibers of the fabric member. In one embodiment, the attachment member is made of rubber and may be heated via any known heating method, including radio frequency (RF) heating. In alterative embodiments, the relative sizes of openings 461' and 462' can vary.

Figure 28B:
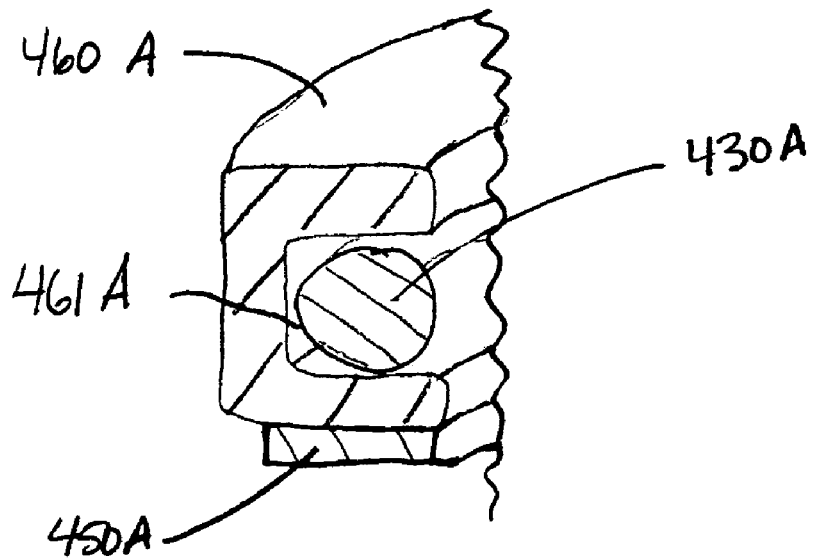
FIGS. 28A and 28B are a side view and cross-section view along line 28B-28B, respectively, of a portion of an ear warmer having a press-fit connection, according to an embodiment of the invention.
Figure 28A:
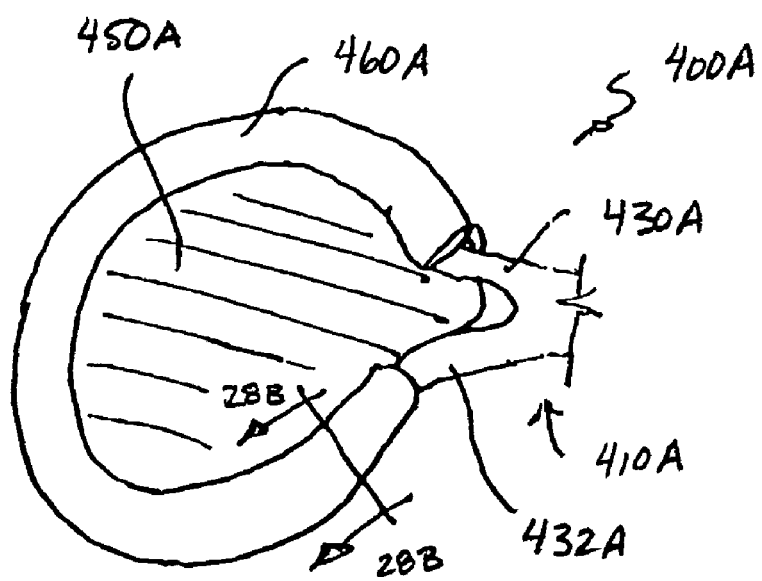

In alternative embodiment, a portion of an ear warmer 400' has a press-fit connection, according to the invention is illustrated in FIGS. 28A and 28B. Ear warmer 400A includes a frame 410A that has an ear portion 430A. As illustrated, the fabric member 450A can be fixedly coupled to an attachment member 460A along a portion of the perimeter of the fabric member 450A. In this embodiment, the attachment member 460A can be made of, for example, plastic or molded rubber. As illustrated in FIG. 28B, the attachment member 460A includes an opening or channels 461A along the length of the attachment member 460A. Opening 461A is configured such that the attachment member 460A forms a press fit over a portion of the perimeter 432A of the ear portion 430A of the frame 410A. This configuration allows the fabric member 450A to be removably attached to the ear portion 430A of the frame 410A. The shape of the ear portion 430A and opening 461A can vary in alternative embodiments.

To fit over the outer side of the perimeter 432A of the ear portion 430A of the frame 410A, the fabric member 450A can be made from an elastic material that is stretched when the fabric member 450A and attachment member 460A are attached to the ear portion 430A of the frame 410A. Alternatively, the fabric member 450A can be larger than the ear portion 430A of the frame 410A so that the fabric member 450A can extend over the perimeter 432A of the ear portion 430A of the frame 410A when being attached to the ear portion 430A of the frame 410A.

As illustrated in FIG. 28B the fabric member 450A is coupled to a side of the attachment member 460A via any known coupling apparatus and/or method, including for example an adhesive. In one embodiment, the fabric member is fused to the attachment member. In this embodiment, the fabric member is placed adjacent the attachment member. The attachment member is then heated such that a portion of the attachment member is melted and absorbed into the fibers of the fabric member. In one embodiment, the attachment member is made of rubber and may be heated via any known heating method, including RF heating.

Figure 28C:
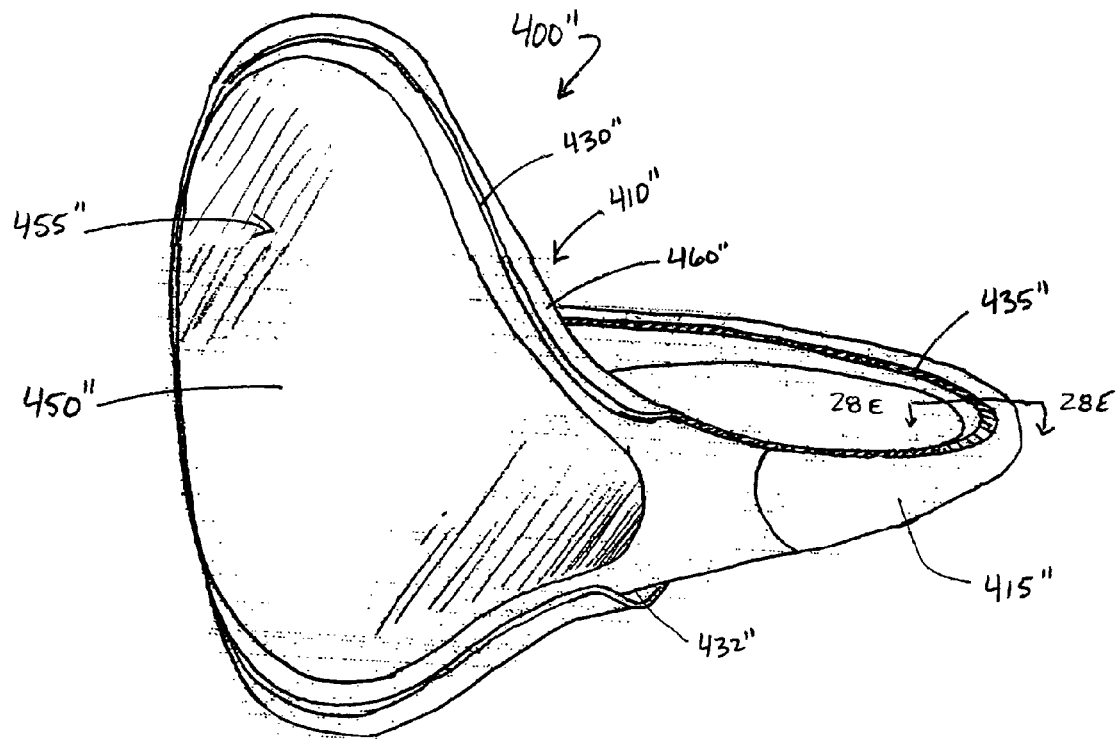
FIG. 28C is a perspective view of an ear warmer having a clip-on connection, according to an embodiment of the invention.
Figure 28D:
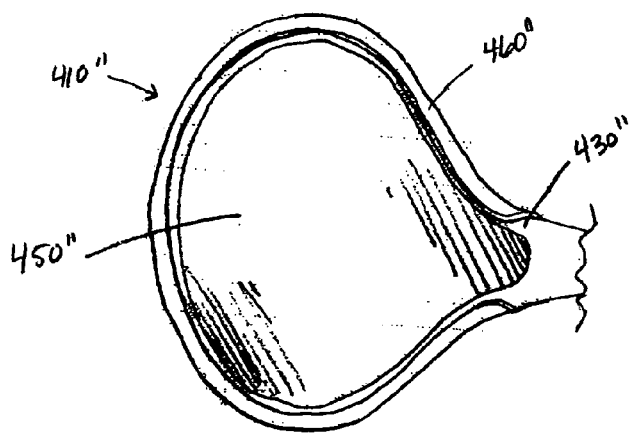
FIG. 28D is a side view of a portion of the ear warmer of FIG. 28C.

FIGS. 28C through 28G illustrate an ear warmer 400" having a press-fit connection, according to an embodiment of the invention. The ear warmer 400" includes a pair of fabric member/attachment member combinations 455" (only one is illustrated) and a frame 410" that has a first ear portion 430" with a perimeter 432", a second ear portion with a perimeter (not illustrated), and a band member 415". Although only one fabric member/attachment member combination 455" is illustrated and described in detail, it should be understood that both fabric member/attachment member combinations 455" can be structurally and functionally similar. As shown in FIG. 28D, a fabric member 450" is coupled (e.g., fixedly coupled) to an attachment member 460" along at least a portion of the perimeter of the fabric member 450". The attachment member 460" illustrated in FIG. 28D has a press-fit structure that defines an opening that is configured to receive the ear portion 430" along at least a portion of the perimeter of the ear portion 430". Specifically, the opening of the attachment member 460" is configured such that it forms a complimentary fit over at least a portion of the perimeter 432" of the ear portion 430" of the frame 410". This mating arrangement of the attachment member 460" and the ear portion 430" allows the fabric member 450" to be removably attached to the ear portion 430" of the frame 410". The attachment member 460" can be made of any material that allows the attachment member 460" to be coupled to the frame, including, for example, rubber, plastic, or metal. Additionally, the fabric member 450" can be made from an elastic material that is stretched when the fabric member 450" and attachment member 460" is coupled to the ear portion 430" of the frame 410" to fit of the outer side of the perimeter of the ear portion 430" of the frame 410". Alternatively, the fabric member 450" can be larger than the ear portion 430" of the frame 410" so that the fabric member 450" can extend over the perimeter 432" of the ear portion 430" of the frame 410" when being coupled to the ear portion 430" of the frame 410".

Figure 28E:
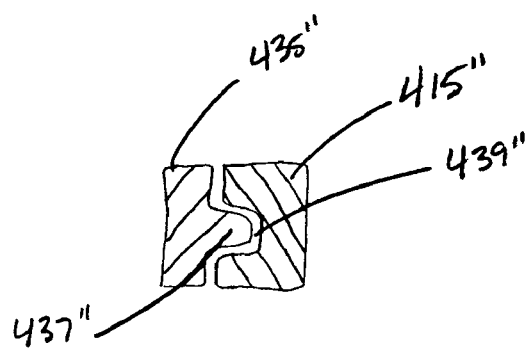
FIG. 28E is a cross-section view taken along line 28E-28E of the ear warmer of FIG. 28C.

As illustrated in FIG. 28C, the ear warmer 400" includes a connector 435" that is coupled to and extends between the fabric member/attachment member combinations 455". When the fabric member/attachment member combinations 455" are coupled to the first ear portion 430" and the second ear portion, respectively, the connector 435" extends along the band member 415" of the ear warmer 400". FIG. 28E is a cross-section taken along 28E-28E of FIG. 28C. As illustrated in FIG. 28E the connector 435" includes a protrusion 437" that is configured to be removably received by a recess 439" disposed in the band member 415". Thus, when the fabric member/attachment member combinations 455" are coupled to the first ear portion 430" and the second ear portion, the connector 435" can be secured to the band member 415".

Figure 28F:
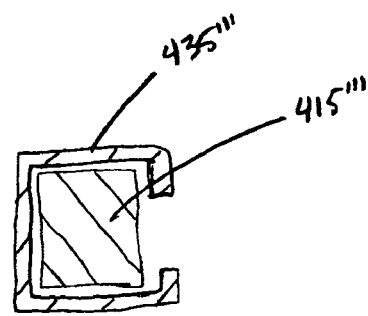
FIGS. 28F and 28G are cross-section views of an ear warmer having a clip-on connection, according to an embodiment of the invention.
Figure 28G:
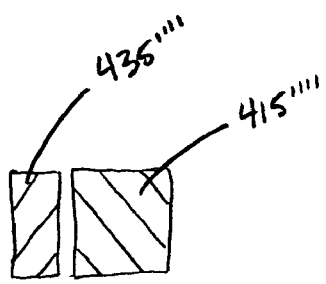

FIGS. 28F and 28G illustrate alternative embodiments of the connector. As illustrated in FIG. 28F, in one embodiment, the connector 435''' includes a opening that is configured to removably receive the band member 415'''. As illustrated in FIG. 28G, in another embodiment, the connector 435'''' is configured to be disposed adjacent the band member 415''''. In this embodiment, the connector 435'''' may be coupled to the band member 415'''' via a known coupling apparatus and/or method, such as an adhesive.

Figure 29:
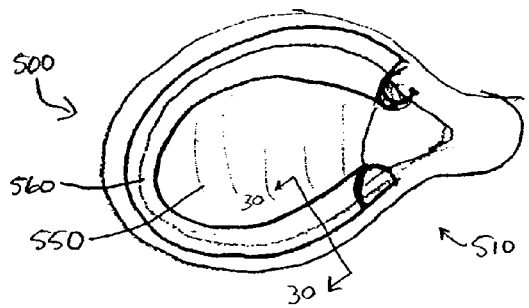
FIGS. 29 and 30 are a side view and cross-section view along line 30-30, respectively, of a portion of an ear warmer having a press-fit connection, according to another embodiment of the invention.
Figure 30:
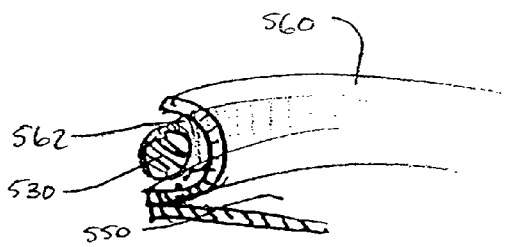

FIGS. 29 and 30 show a side view and cross-section view along line 30-30 in FIG. 29, respectively, of a portion of an ear warmer 500 having a press-fit connection, according to another embodiment of the invention. The ear warmer 500 includes a frame 510 that has an ear portion 530. Similar to that embodiment shown in FIGS. 27 and 28, in FIG. 30, the fabric member 550 can be fixedly coupled to an attachment member 560 along a portion of the perimeter of the fabric member 550. In this embodiment, however, the opening 562 defined by the attachment member 560 along its length is directed outwardly. As shown in FIG. 30, the opening 562 has a size such that the attachment member 560 forms a press fit along a portion of the ear portion 530 of the frame 510. In particular, the ear portion 530 of the frame 510 defines an interior region defined by a perimeter. The attachment member 560 removably attaches the fabric member 550 to a portion of this perimeter of the interior region. The attachment member 560 has sufficient strength and rigidity so that the attachment member 560 is inserted or "popped" into an opening defined in the ear portion 530.

Figure 31:
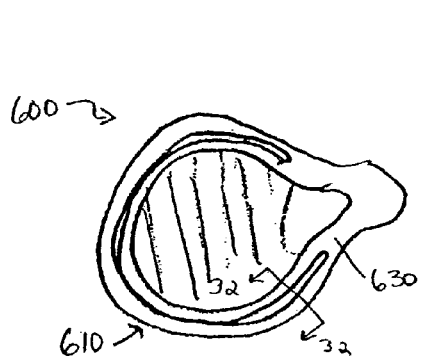
FIGS. 31 and 32 are a side view and cross-section view along line 32-32, respectively, of a portion of an ear warmer having a tongue-and-groove connection, according to an embodiment of the invention.
Figure 32:
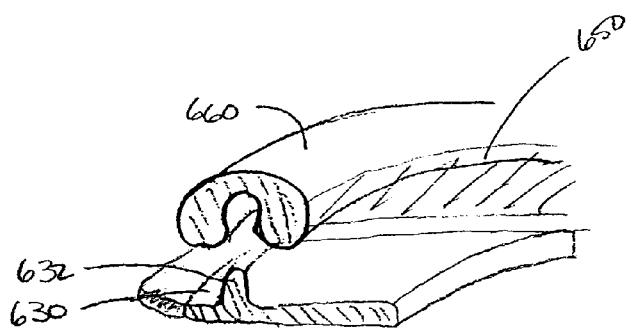

FIGS. 31 and 32 show a side view and cross-section view along line 32-32 in FIG. 31, respectively, of a portion of an ear warmer 600 having a tongue-and-groove connection, according to an embodiment of the invention. In this embodiment, the ear warmer 600 includes a frame 610 that has an ear portion 630. As shown in FIG. 32, the fabric member 650 can be coupled (e.g., fixedly coupled) to an attachment member 660 along a portion of the perimeter of the fabric member 650. In this embodiment, the attachment member 660 has a surface with a groove structure formed therein, and complimentary fits onto or receives the tongue-like portion 632 of the ear portion 630 of the frame 610. This mating of the attachment member 660 and the ear portion 630 allows the fabric member 650 to be removably attached to the ear portion 630 of the frame 610. The tongue-like portion 632 of the ear portion 630 of the frame 610 can be monolithically formed with the remaining portions of the ear portion 630 of the frame 610. Alternatively, a tongue-like member can be coupled (e.g., fixedly coupled) to the ear portion of the frame by welding or an adhesive. In another alternative embodiment, the tongue-like structure can be coupled (e.g., fixedly coupled) to the fabric member and the groove-like structure can be disposed on the ear portion or the frame, for example, either fixedly coupled to or monolithically formed with the ear portion of the frame.

Figure 33:
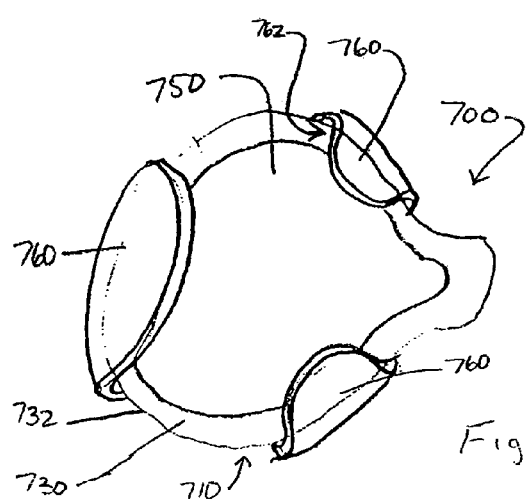
FIG. 33 is a side view of a portion of an ear warmer having a clip-on connection, according to an embodiment of the invention.

FIG. 33 shows a side view of a portion of an ear warmer 700 having a clip-on connection, according to an embodiment of the invention. The ear warmer 700 includes a frame 710 that has an ear portion 730 with a perimeter 732. As shown in FIG. 33, a fabric member 750 can be coupled (e.g., fixedly coupled) to one or more attachment members 760 along various positions of the perimeter of the fabric member 750. More specifically, FIG. 33 shows three attachment members 760 although in other embodiments, one, two, four or more than four attachment members are possible. The various attachment members can be formed integrally or can be coupled together by different structures. Each of the attachment members 760 shown in FIG. 33 has a clip-like structure that defines an opening 762 along its length and is directed inwardly. These attachment members 760 can be made of any material that allows the attachment members 760 to coupled to the frame, including, for example, plastic or metal. The opening 762 of each attachment member 760 in configured such that it forms a complimentary fit over a portion of the perimeter 732 of the ear portion 730 of the frame 710. This mating arrangement of the attachment members 760 and the ear portion 730 allows the fabric member 750 to be removably attached to the ear portion 730 of the frame 710. Similar to the embodiment described above in reference to FIGS. 27 and 28, to fit of the outer side of the perimeter of the ear portion 730 of the frame 710, the fabric member 750 can be made from an elastic material that is stretched when the fabric member 750 and attachment members 760 are coupled onto the ear portion 730 of the frame 710. Alternatively, the fabric member 750 can be larger than the ear portion 730 of the frame 710 so that the fabric member 750 can extend over the perimeter 732 of the ear portion 730 of the frame 710 when being coupled onto the ear portion 730 of the frame 710.

FIGS. 34 through 38 show examples of a fabric member removably coupled to the ear portion of the frame by covering substantially an entirety of the opening on the inner side of the ear portion of the frame and less than an entirety of the opening on the outer side of the ear portion of the frame. More specifically, the ear portion of the frame typically defines an opening through which sound can pass. This opening has an interior portion corresponding to the inner side of the ear portion of the frame and an exterior portion corresponding to the outer side of the ear portion of the frame. As described in more detail in reference to FIGS. 34 through 38, an ear portion of the fabric member can be configured such that it covers the interior portion of the opening substantially in its entirety and covers the exterior portion of the opening in less than its entirety. Covering the interior portion of the opening "substantially in its entirety" is intended to describe embodiments where the entire interior portion of the opening is covered except for minor exceptions such as, for example, small vents.

Figure 34:
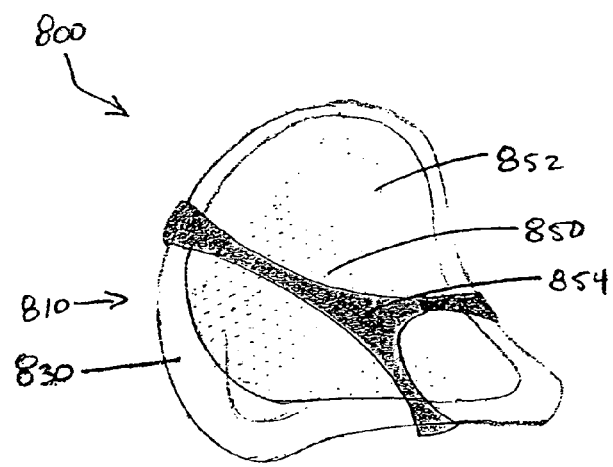
FIG. 34 is a side view of a portion of an ear warmer having a fabric member, according to an embodiment of the invention.

FIG. 34 shows a side view of a portion of an ear warmer 800 having a fabric member 850, according to an embodiment of the invention. The ear warmer 800 includes a frame 810 that has an ear portion 830. In one embodiment, the fabric member 850 includes an ear portion with a heat-retaining fabric 852 on the inner side. The ear warmer 800 can include an elastic fabric or member 854 on the outer side. In one embodiment, the elastic fabric 854 is coupled (e.g., fixedly coupled) to the heat-retaining fabric 852 at three locations. In alternative embodiments, the elastic or rubber fabric can be coupled to the heat-retaining fabric 852 at any number of locations. In one embodiment, the elastic member 854 can be a clip or snap-on structure that clips or clamps the heat-retaining fabric 852 to the ear portion 830. In an alternative embodiment, the elastic member 854 can be a separate piece that can wrap around the inner side and the outer side of a portion of the ear portion 830 and couple the fabric 852 thereto. In another embodiment, the heat-retaining fabric 852 and the elastic fabric 854 are coupled together in a manner other than fixedly coupled, such as removably coupled.

The fabric member 850 can be removably coupled to the ear portion 830 of the frame 810 by stretching the elastic fabric on the outer side of the fabric member 850 so that it can moved over the distal end of the ear portion 830 of the frame 810. As shown in FIG. 34, the heat-retaining fabric 852 on the inner side of the fabric member 850 covers the interior portion of the opening of the ear portion 830 of the frame 810 substantially in its entirety while the elastic fabric 854 covers the exterior portion of the opening of the ear portion 830 of the frame 810 in less than its entirety. Any combination of coupling techniques can be used to couple the fabric member 850 to the ear portion 830.

Figure 35:
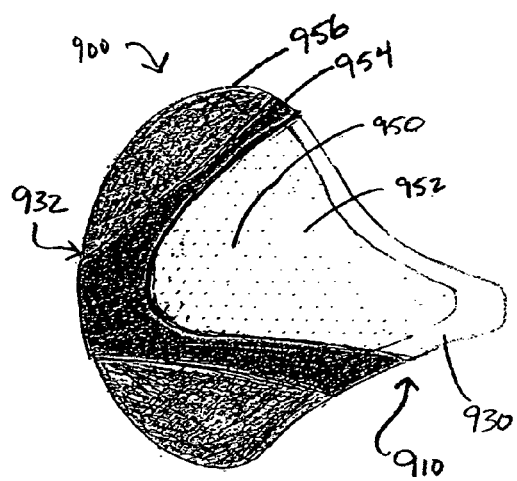
FIG. 35 is a side view of a portion of an ear warmer having a fabric member, according to another embodiment of the invention.

FIG. 35 shows a side view of a portion of an ear warmer 900 having a fabric member 950, according to another embodiment of the invention. As shown in FIG. 35, the ear portion of the fabric member 950 has a heat-retaining fabric 952 on the inner side, and an elastic fabric portion 954 and a heat-retaining portion 956 on the outer side. The elastic fabric can be, for example, a rubber material or a heat-retaining fabric. In this particular embodiment, the outer side of the fabric member 950 is coupled (e.g., fixedly coupled) to the heat-retaining fabric 952 on the inner side along a portion of the perimeter. Thus, the fabric member 950 can be removably coupled to the ear portion 930 of the frame 910 by stretching the elastic fabric 954 on the outer side of the fabric member 950 so that it can move over the distal end 932 of the ear portion 930 of the frame 910. In one embodiment, the fabric 952 and the heat-retaining portion 956 can be formed integrally.

Figure 36:
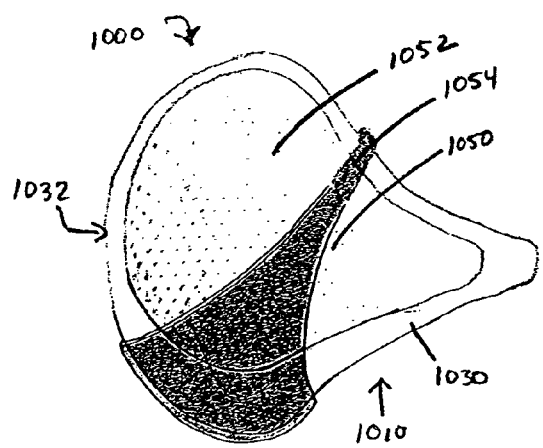
FIG. 36 is a side view of a portion of an ear warmer having a fabric member, according to another embodiment of the invention.

FIG. 36 shows a side view of a portion of an ear warmer 1000 having a fabric member 1050, according to another embodiment of the invention. Fabric member 1050 is coupled in a similar manner as fabric member 850 described above. As shown in FIG. 36, the ear portion of the fabric member 1050 has a heat-retaining fabric 1052 and an elastic fabric 1054. The elastic fabric can be, for example, a rubber material or a heat-retaining fabric. In this particular embodiment, the elastic fabric 1054 on the outer side is coupled (e.g., fixedly coupled) to the heat-retaining fabric 1032 on the inner side at two locations. The fabric member 1050 can be removably coupled to the ear portion 1030 of the frame 1010 by stretching the elastic fabric 1054 on the outer side of the fabric member 1050 so that it can move over the distal end 1032 of the ear portion 1030 of the frame 1010.

Figure 37:
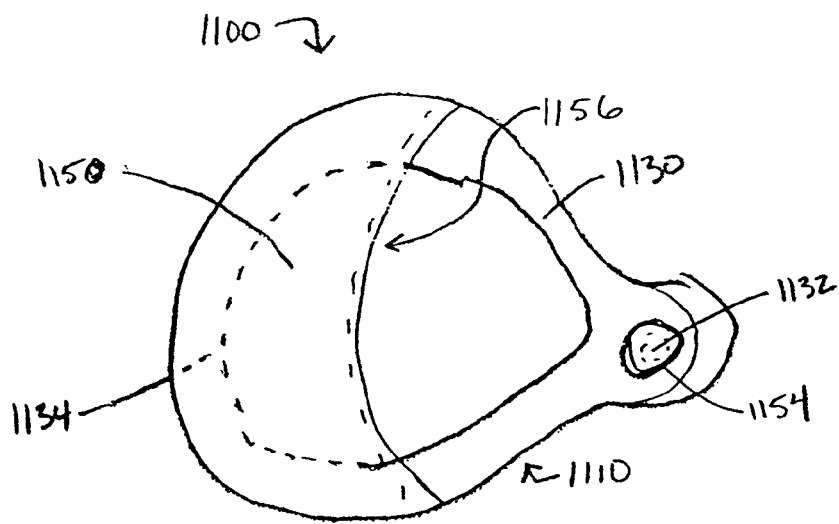
FIG. 37 is a side view of a portion of the ear warmer having a fabric member, according to another embodiment of the invention.
Figure 38:
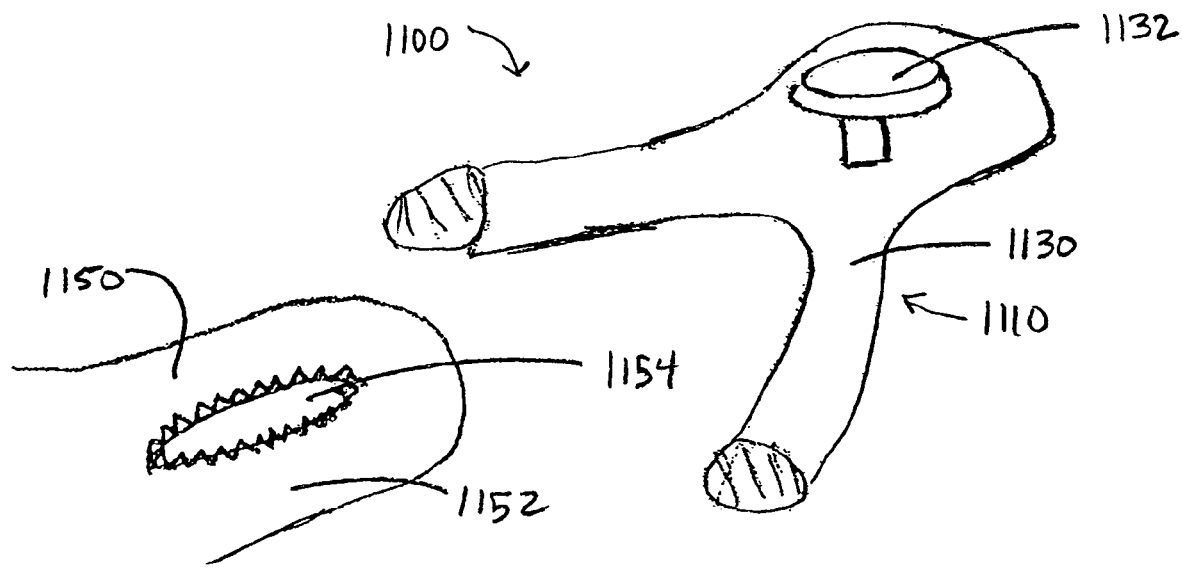
FIG. 38 is a perspective assembly view of the portion of the ear warmer shown in FIG. 37.

FIG. 37 shows a side view of a portion of the ear warmer 1100 having a fabric member 1150, according to another embodiment of the invention. FIG. 38 shows a perspective assembly view of the portion of the ear warmer 1100 shown in FIG. 37. As shown in FIG. 37, the fabric member 1150 (one is shown in FIG. 37 for one ear portion of the frame) has an inner side and an outer side. As shown in FIG. 38, the inner side 1152 of the fabric member 1150 includes a coupling portion 1154 embodied as a button hole. The ear portion 1130 of the frame 1110 includes a coupling portion 1132 embodied as a button and post. The coupling portion 1154 of the fabric member 1150 is configured to mate with the coupling portion 1132 of the ear portion 1130 of the frame 1110 such that the fabric member 1150 is removably coupled to the ear portion 1130 of the frame 1110. As shown in FIGS. 37 and 38, the coupling portion 1132 of the frame 1110 is disposed on the inner side of the frame.

More specifically, the inner side and outer side of the fabric member 1150 form a receptacle 1156 into which the distal end 1134 of the ear portion 1130 of the frame 1110 can be removably disposed. This side of the ear portion of the fabric member 1150 is referred to herein as the distal end. The proximate end of the fabric member 1150 is also removably coupled to the ear portion 1130 of the frame 1110, as discussed above, by the coupling portion 1154 of the fabric member 1150 fitting into the coupling portion 1132 of the ear portion 1130 of the frame 1110. Thus, the overall fabric member 1150 can be coupled to the ear portion 1130 of the frame 1110 by coupling the distal end of the fabric member 1150 to the distal end 1134 of the ear portion 1130 of the frame 1110, and then coupling the proximate end of the fabric member 1150 to the proximate end of the ear portion 1130 of the frame 1110. The fabric member 1150 can be removed from the frame 1110 by the reverse process.

Although the coupling portion 1132 of the ear portion 1130 of the frame 1110 is shown in FIGS. 37 and 38 as protruding from the inner side of the frame, in alternative embodiments, the coupling portion of the frame extends from a recess in the inner side of the frame. Thus, the distal end of the coupling portion of the frame corresponds to the remaining inner surface of the ear portion of the frame in that region and in general they form a smooth surface having the recess.

In alternative embodiments, the coupling portion of the ear portion of the frame and the coupling portion of the ear portion of the fabric member can be disposed on any part of the frame, including the outer side of the frame. In such an alternative embodiment, the outer side of the ear portion of the frame is substantially covered in its entirety and the inner side of the ear portion of the frame covered in less than its entirety.

In an alternative embodiment, the ear portion of the frame and the ear portion of the fabric member can be coupled together using any conventional technique, such as hook-and-loop fasteners, snap-fit connections, and button-and-hole arrangements having the hole on the frame.

Figure 39:
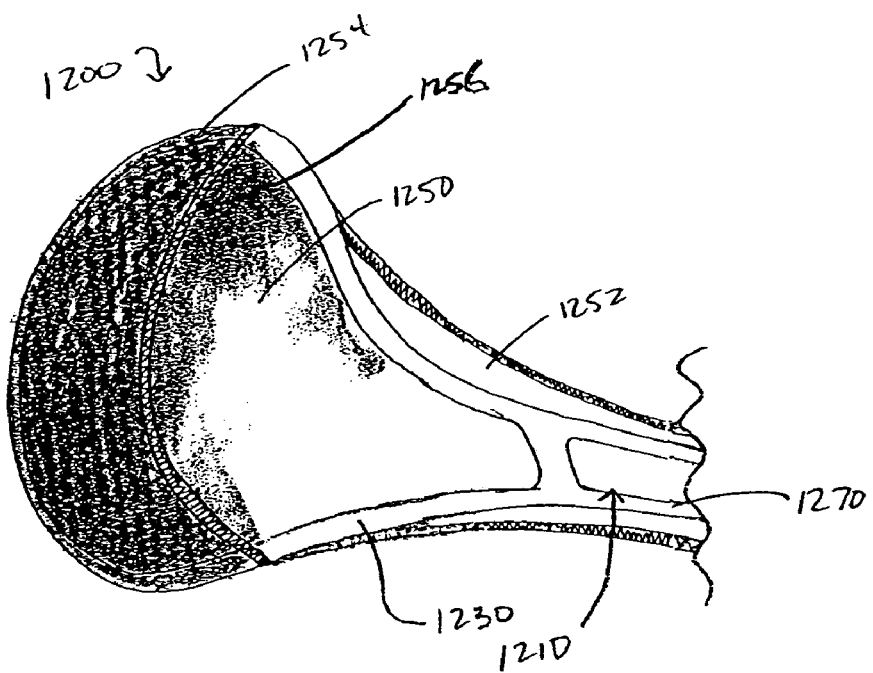
FIG. 39 is a perspective view of a portion of an ear warmer having a fabric member covering at least a portion of the inner side of the frame, according to an embodiment of the invention.
Figure 40:
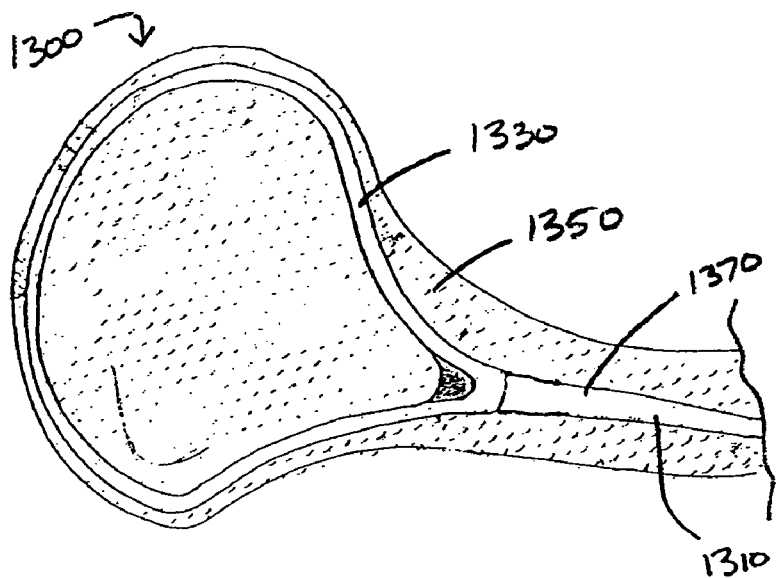
FIG. 40 is a perspective view of a portion of an ear warmer having a fabric member covering at least a portion of the inner side of the frame, according to another embodiment of the invention.

FIGS. 39 and 40 show examples of a fabric member removably coupled to the frame by covering substantially an entirety of the inner side of the frame and less than an entirety of the opening on the outer side of each ear portion of the frame. More specifically, the examples shown in FIGS. 39 and 40 show a fabric member that substantially covers the entirety of the inner side of the frame including its ear portions and band portion while covering less than the entirety of the outer side of the frame.

FIG. 39 shows a perspective view of a portion of an ear warmer 1200 having a fabric member 1250 covering the inner side of the frame 1210, according to an embodiment of the invention. As shown in FIG. 39, the fabric member 1250 has an inner-side portion 1252 and an outer-side portion 1254. The inner-side portion 1252 of the fabric member 1250 corresponds to both ear portions 1230 of the frame 1210 (of which only one is shown in FIG. 39) and the band portion 1270 of the frame 1210 (only a portion of which is shown in FIG. 39). In this embodiment, the outer-side portion 1254 of the fabric member 1250 can be extended over the distal end of the ear portions 1230 of the frame 1210. Thus, the distal end of the ear portions 1230 of the frame 1210 can be retained in a receptacle 1256 formed by the inner-side portion 1252 and the outer-side portion 1254 of the fabric member 1230. The outer-side portion 1252 of the fabric member 1250 can be made of, for example, an elastic fabric that allows the fabric member 1250 to be stretched over the distal end of the ear portions 1230 of the frame 1210 to insert and remove the frame 1210 from the fabric member 1250. In alternative embodiments, the fabric members can be bound, sewn, welded, coupled inside out, or monolithically formed (i.e., unitary construction).

FIG. 40 shows a perspective view a portion of an ear warmer 1300 having a fabric member 1350 covering the inner side of the frame 1310, according to another embodiment of the invention. As shown in FIG. 40, the fabric member 1350 has only an inner-side portion. The inner-side portion of the fabric member 1350 corresponds to both ear portions 1330 of the frame 1310 (of which only one is shown in FIG. 40) and the band portion 1370 of the frame 1310 (only a portion of which is shown in FIG. 40). In this embodiment, the inner-side portion of the fabric member 1350 can be fixedly coupled to the frame 1310 as described above in reference to FIG. 26, or can be removably coupled to the frame, for example, as described above in reference to FIGS. 31 and 32.

Although not explicitly shown in FIGS. 39 and 40, in alternative embodiments, the fabric member can cover substantially the entirety of the inner side of the frame while being removably coupled to the frame as described above, for example, in reference to FIGS. 27 through 30, 33 and 38. In a further alternative embodiment, the fabric member can have a first portion that covers one of the ear portions of the frame and a second portion that covers the other of the ear portions of the frame. In this embodiment, the first portion of the fabric member can be coupled to the second portion of the fabric member via any type of coupling device, such as hook and loop configuration.

Figure 41:
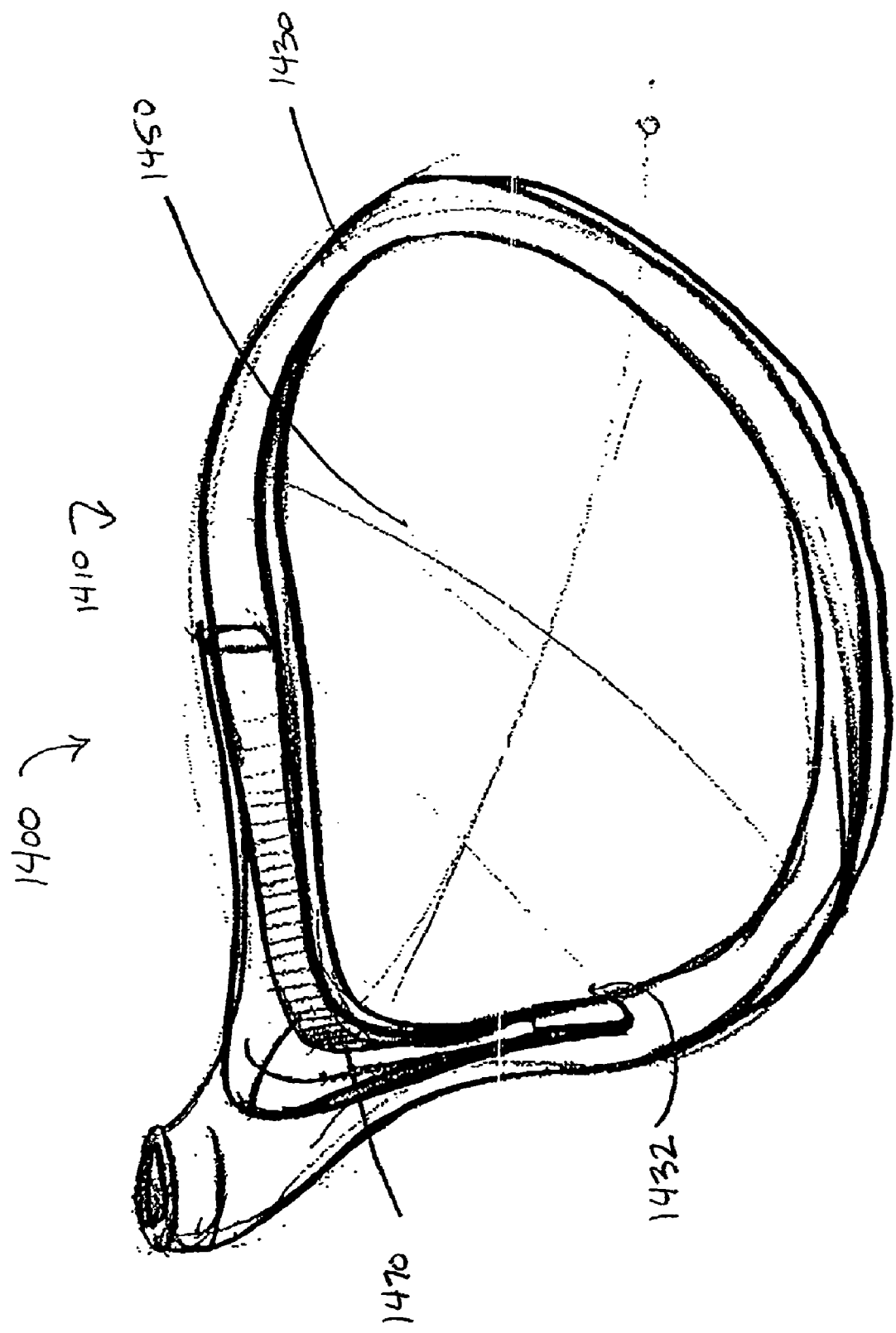
FIG. 41 is a perspective view a portion of an ear warmer having a fabric member and a support member, according to another embodiment of the invention.
Figure 42:
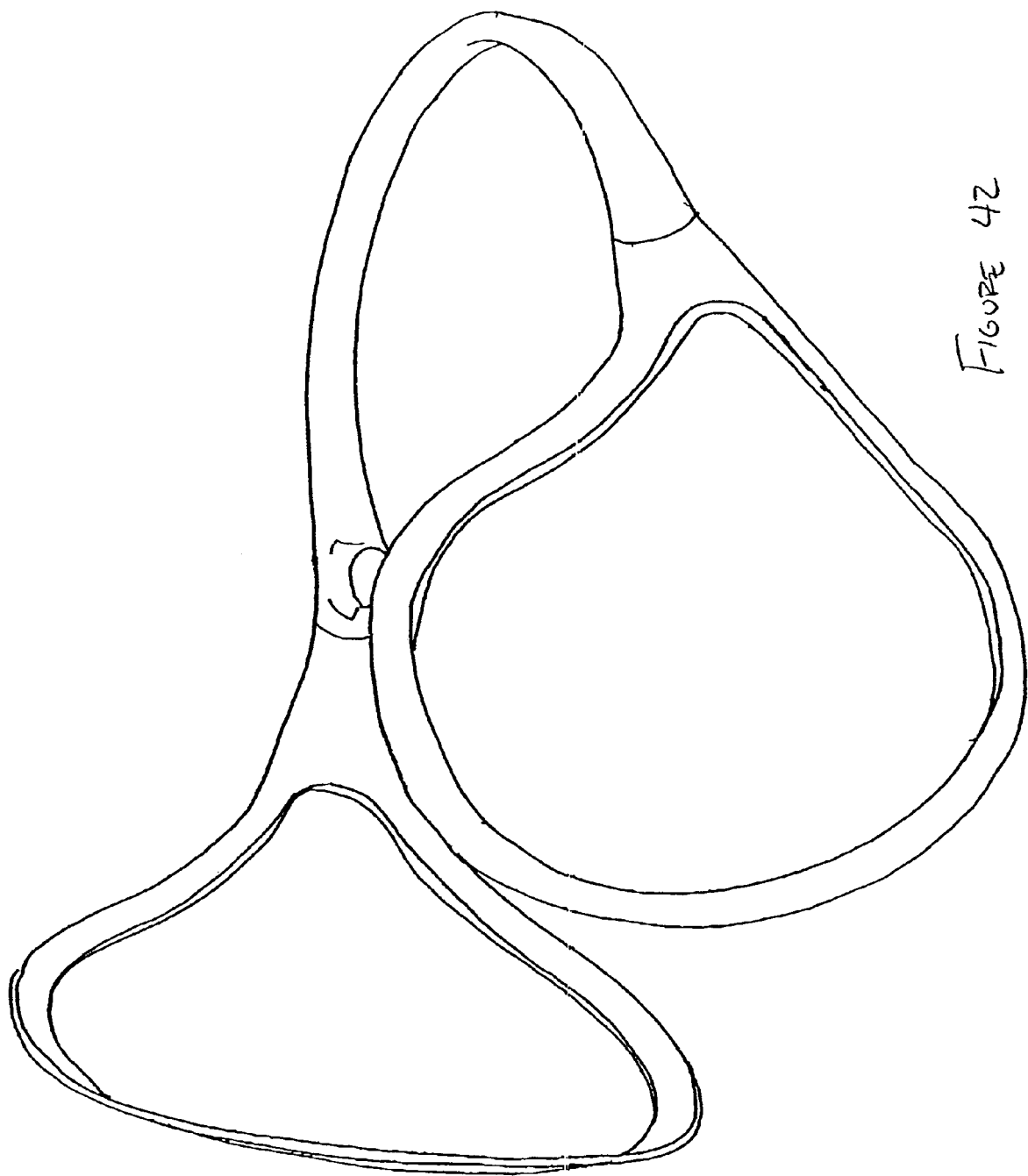
FIG. 42 is a perspective view of a frame of an ear warmer according to an embodiment of the invention.
Figure 43:
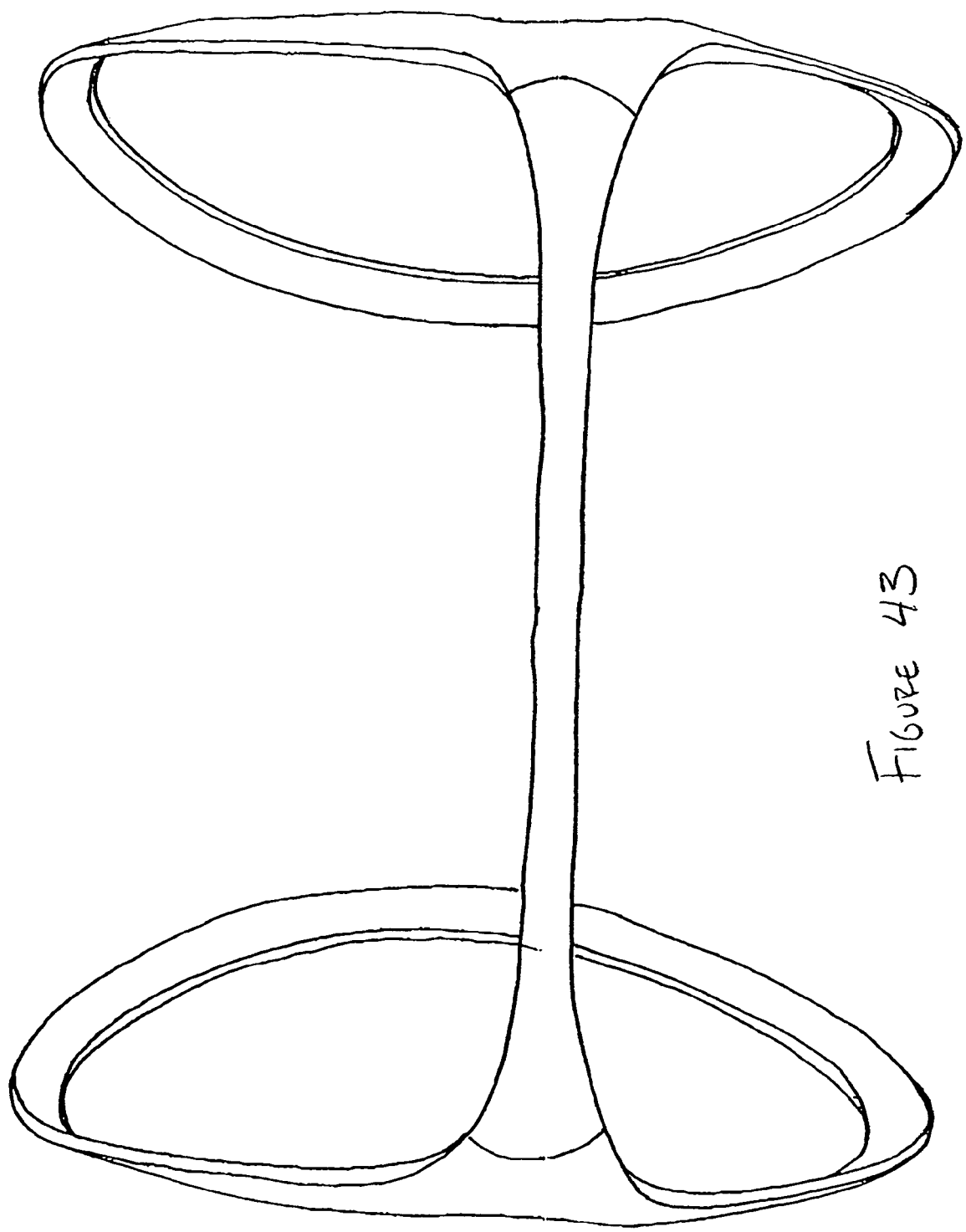
FIG. 43 is a rear view of the frame illustrated in FIG. 42.
Figure 44:
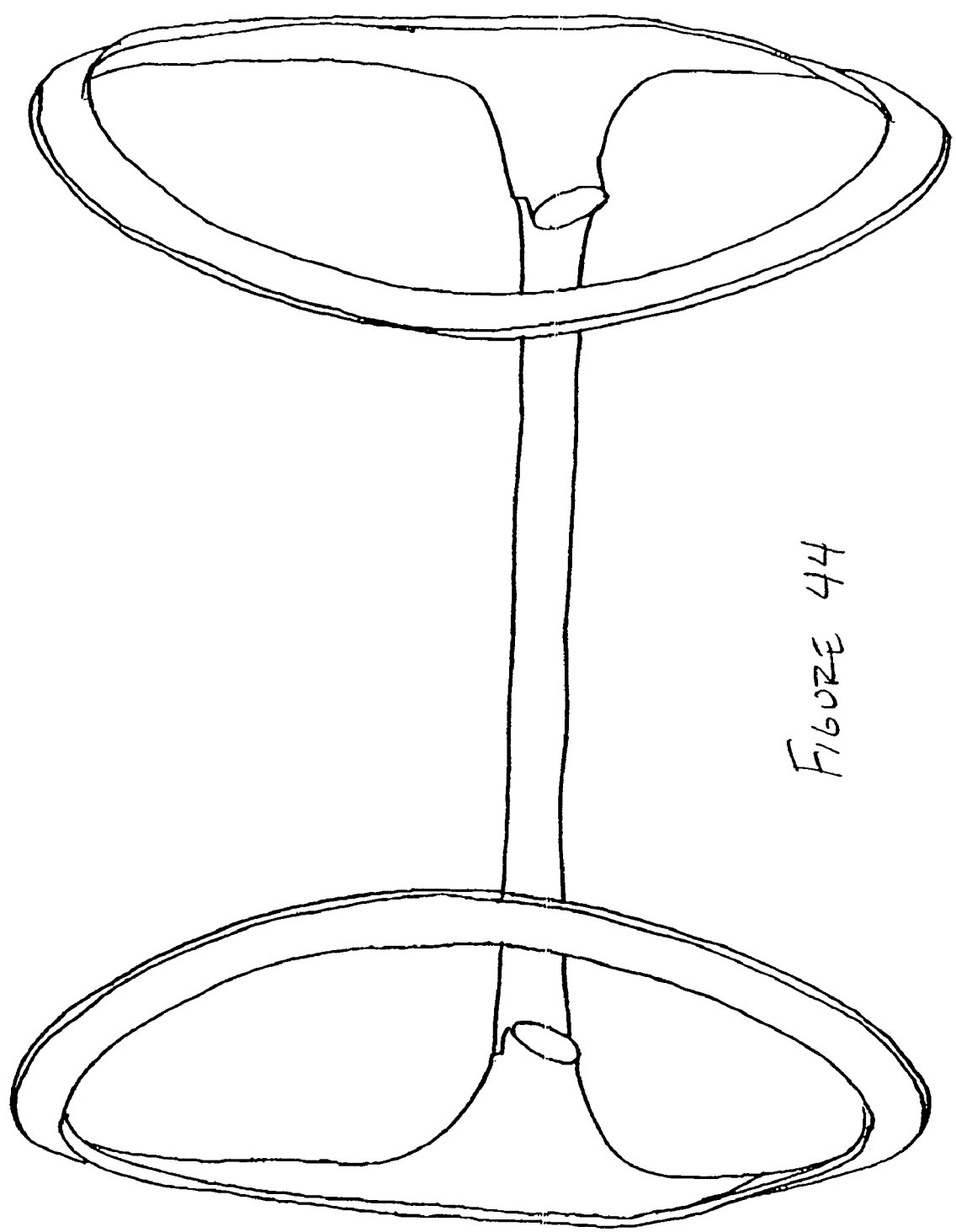
FIG. 44 is a front view of the frame illustrated in FIG. 42.
Figure 45:
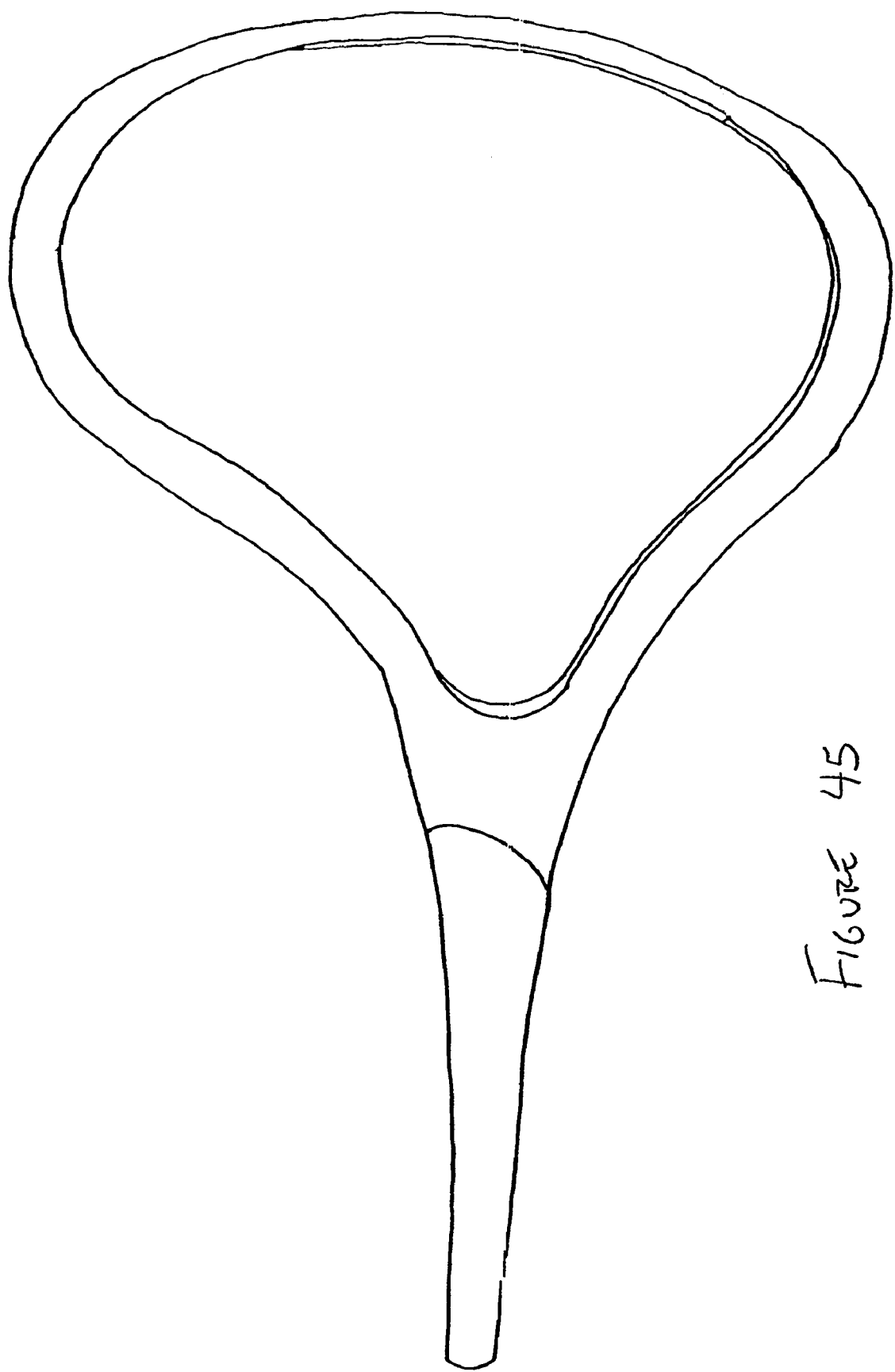
FIG. 45 is a right side view of the frame illustrated in FIG. 42.
Figure 46:
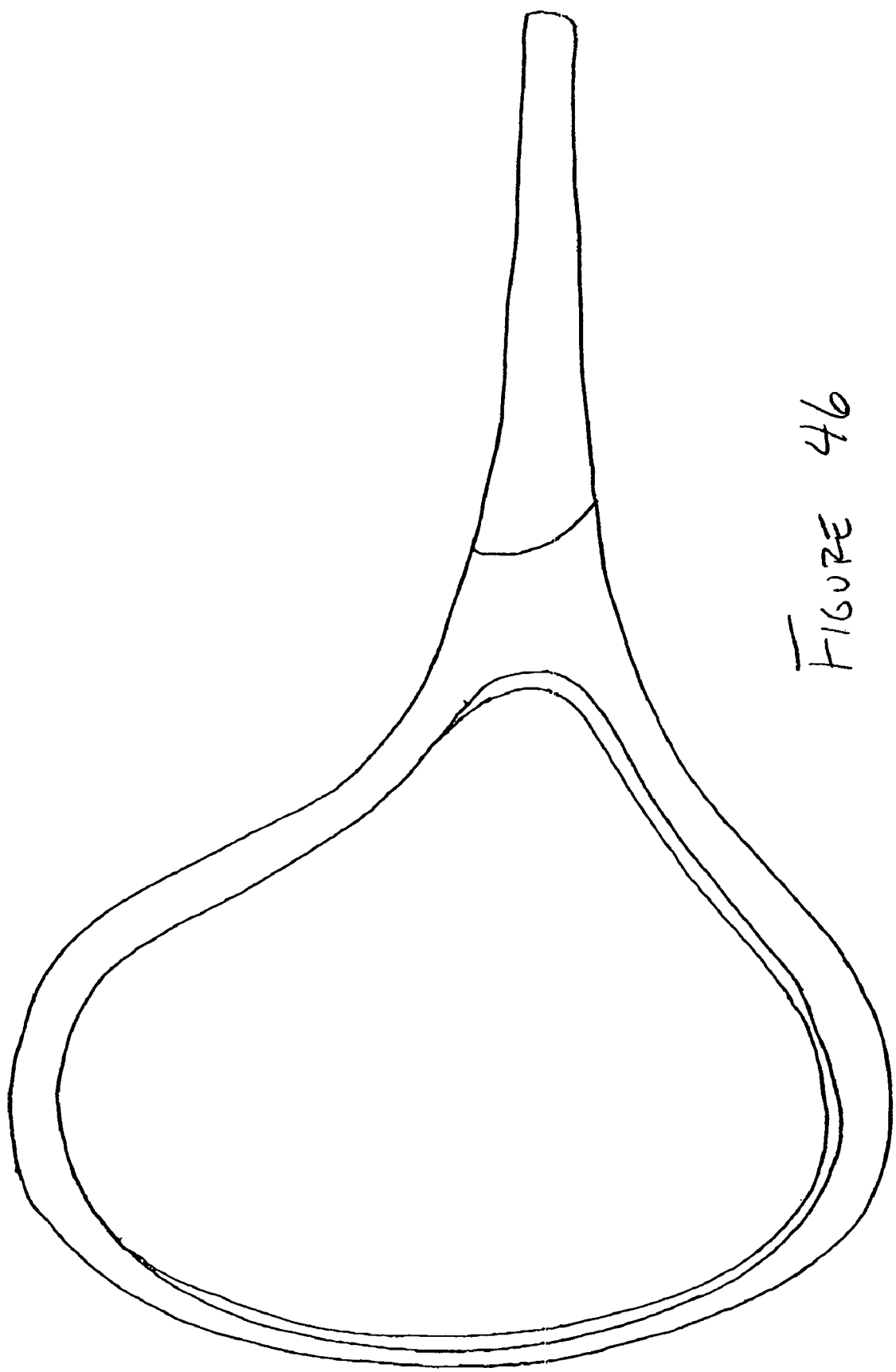
FIG. 46 is left side view of the frame illustrated in FIG. 42.
Figure 47:
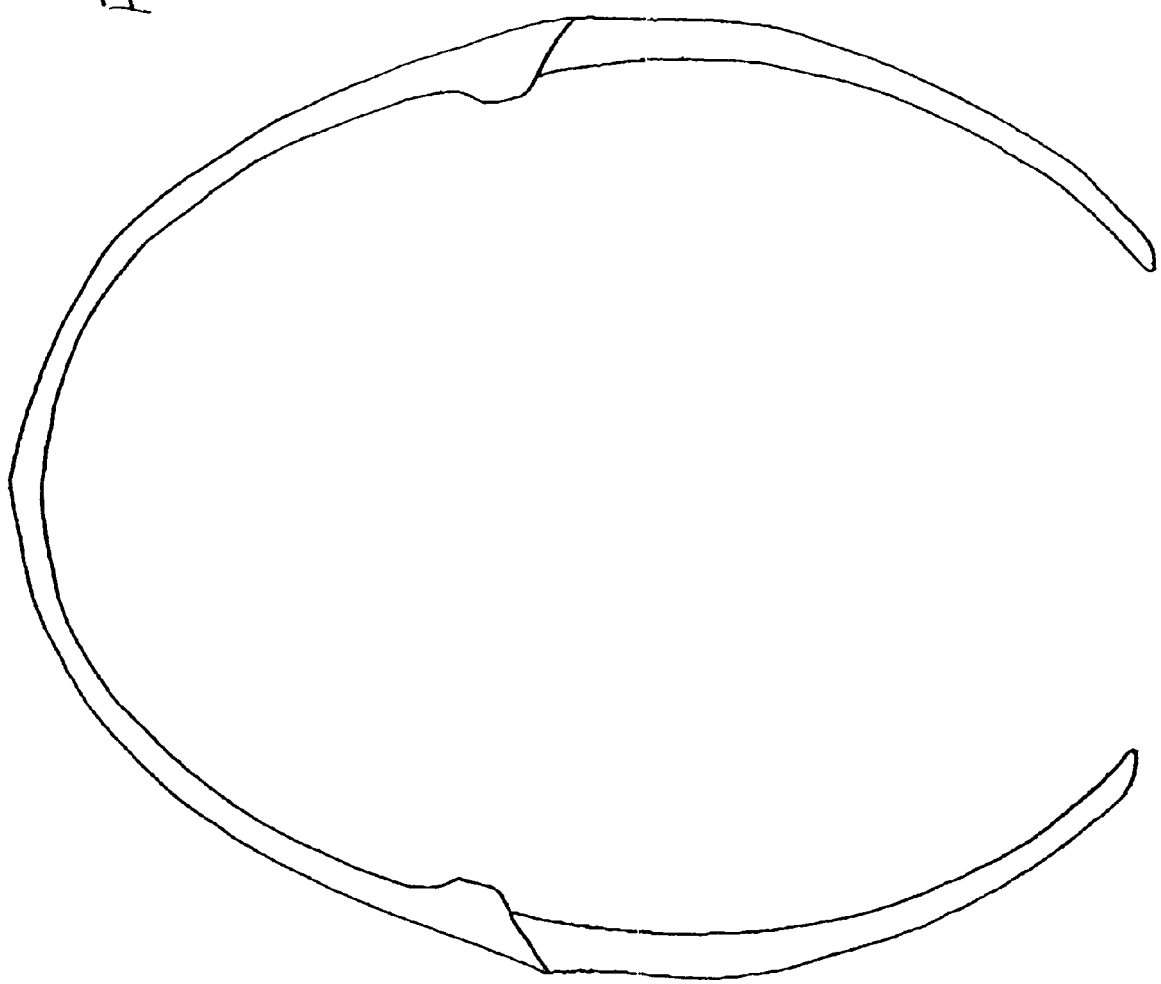
FIG. 47 is a top view of the frame illustrated in FIG. 42.
Figure 48:
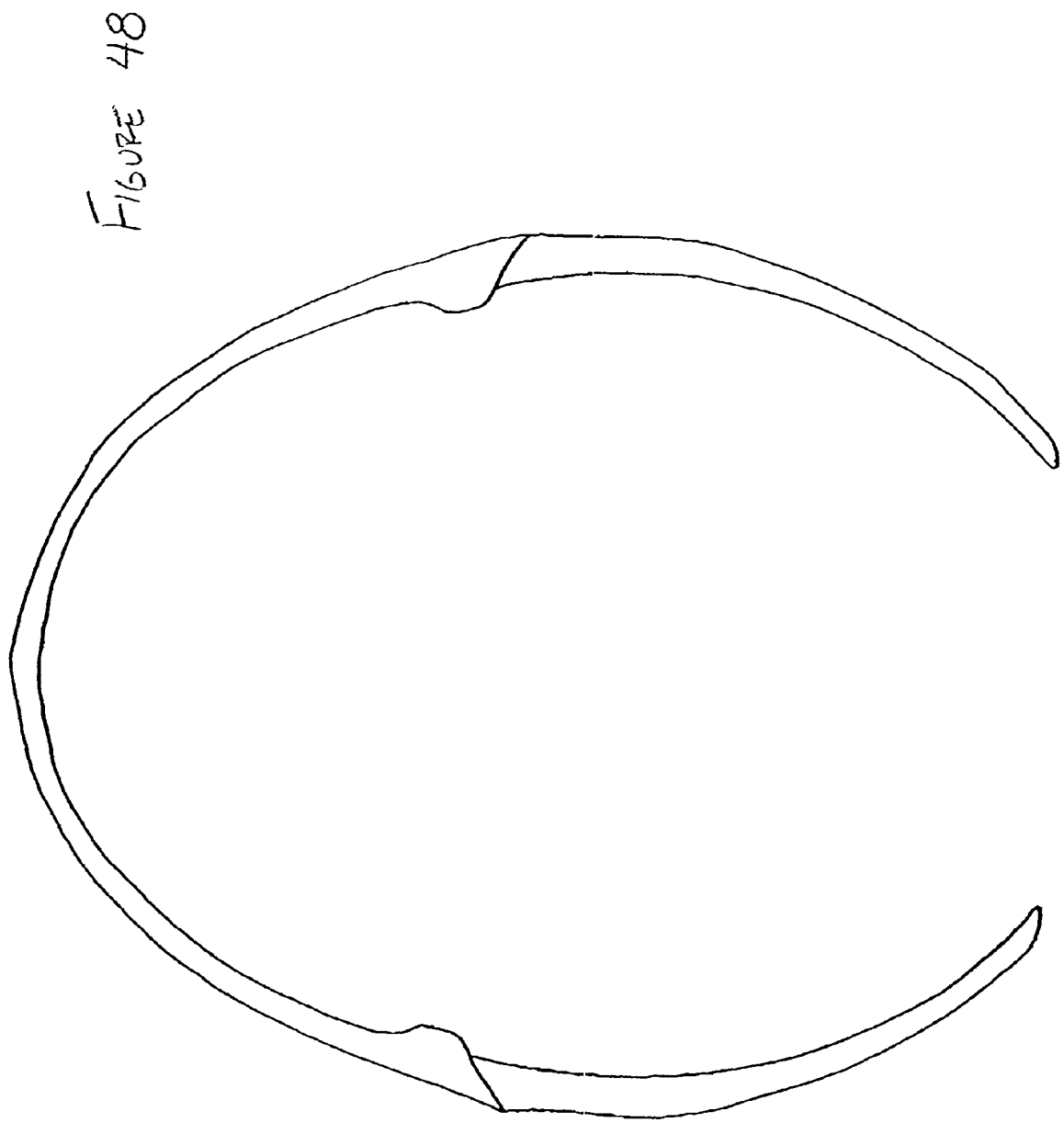
FIG. 48 is a bottom view of the frame illustrated in FIG. 42.

FIG. 41 shows a perspective view a portion of an ear warmer 1400 having a fabric member 1450 and a contact member 1470, according to another embodiment of the invention. As shown in FIG. 41, the frame 1410 includes a contact member 1470 disposed on the inner side 1432 of the ear portion 1430 of the frame 1410. The contact member 1470 is configured to provide support and comfort to the user of the ear warmer 1400 by contacting the portion of the user's head behind the user's ears. Additionally, the contact member 1470 provides a seal between the ambient conditions and the user's ear. In other words, the contact member fills the gap between the frame 1410 of the ear warmer 1400 and the user's head. In this embodiment, the contact member 1470 extends along a portion of the inner side 1432 of the ear portion 1430. In alternative embodiments, the contact member extends along substantially the entire inner side of the ear portion.

In one embodiment, the fabric member includes a receptacle that receives the contact member. In alternative embodiments, the contact member is otherwise coupled to the fabric member, such as via an adhesive. In an alternative embodiment, the contact member is coupled to another portion of the ear warmer, such as the band portion of the frame.

In one embodiment, the contact member can be made of a pre-formed foam or rubber material that is covered in fabric. The contact can be slightly deformed and inserted into the opening of the ear portion. The contact member is then released and retained via the opening.

In one embodiment, the contact member is a foam material or rubber material that is not covered in fabric. In an alternative embodiment, the contact member is made of a material other than foam. In a further alternative embodiment, the contact member is a foam material that is covered with a material other than fabric.

Figure 49:
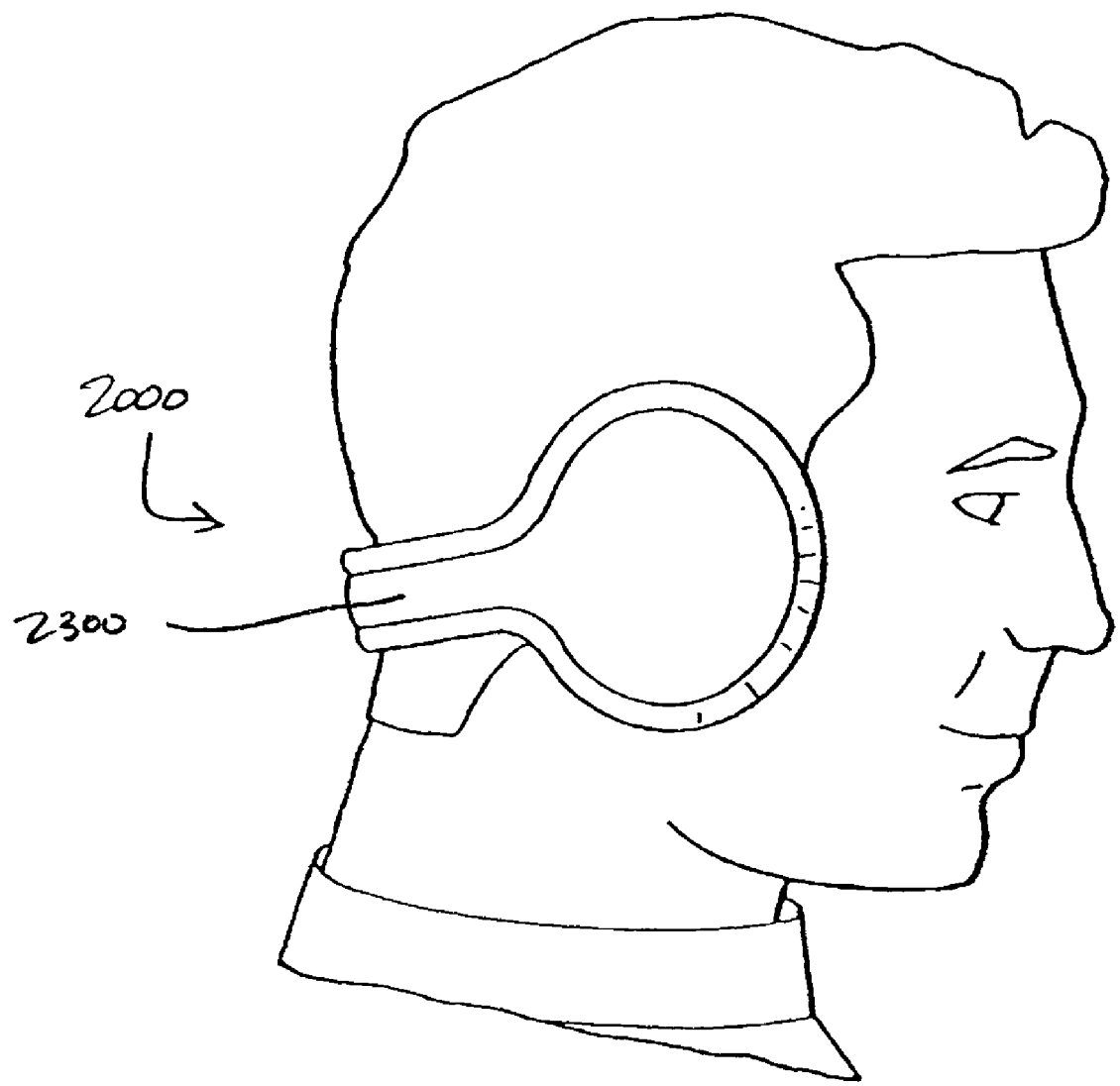
FIG. 49 is a side view of a ear warmer being worn by a user according to an embodiment of the invention.

An ear warmer according to an embodiment of the invention is illustrated in FIG. 49. The ear warmer 2000 includes a frame (not illustrated) disposed within a cavity of a shell 2300. The ear warmer 2000 is disposable in a collapsed configuration (i.e., when the ear portions are disposed parallel to and in substantially in the same plane as the band portion) and an expanded configuration (i.e., when the ear portions extend away from the band portion). When the ear warmer 2000 is in its expanded configuration, the ear warmer 2000 may be placed on a head of a user such that the ear warmer 2000 covers the two ears of the user and extends around a back of the head and/or neck of the user.

An embodiment of a frame according to the invention is illustrated in FIGS. 50 through 59. In this embodiment, the frame 2100 of the ear warmer 2000 includes a band portion 2106, a first ear portion 2102 coupled to a first end 2108 of the band portion 2106, and a second ear portion 2104 coupled to a second end 2110 of the band portion 2106. Band portion 2106 includes two or more members that are slidably coupled together so that the overall length of the band portion 2106 can be adjusted. In another embodiment, the band portion is a single member that does not adjust in length.

Specifically, in this embodiment, the first ear portion 2102 includes a first end portion 2112 and a second end portion 2114. The first end portion 2112 is coupled to the band portion 2106. The second end portion 2114 of the first ear portion 2102 is disposed opposite the first end portion 2112 of the first ear portion 2102 and distal from the band portion 2106 when the frame is in its expanded configuration. Similarly, the second ear portion 2104 includes a first end portion 2116 and a second end portion 2118. The first end portion 2116 is coupled to the band portion 2106. The second end portion 2118 of the second ear portion 2104 is disposed opposite the first end portion 2116 of the second ear portion 2104.

In one embodiment, the first ear portion 2102 and the second ear portion 2104 are movably coupled to the band portion 2106. Connectors 2120 and 2122 rotatably couple the first ends 2112 and 2116 of the ear portions 2102 and 2104 to the ends 2108 and 2110 of the band portion 2106, respectively. Connectors 2120 and 2122 are inserted through openings 2127 (only one is illustrated) formed in the ear portions 2102 and 2104 and through openings 2164 (only one is illustrated) formed in the band portion 2106. Thus, the ear portions 2102 and 2104 are coupled to the band portion 2106 such that the ear portions 2102 and 2104 may rotate or pivot about connectors 2120 and 2122 with respect to the band end portions 2108 and 2110, respectively. In one embodiment, the connectors 2120 and 2122 are rivets. In alternative embodiments, the connectors are other types of coupling mechanisms, such as brads or screws. In another embodiment, a connecting structure, such as a projection, is coupled to each ear portion and subsequently inserted through the opening in the band portion. In alternative embodiments, the first ear portion and the second ear portion are rotatably and/or slidably coupled to the band portion.

When the ear warmer is placed on a user's head, the ear portions and band portion collectively provide a clamping force which keeps the ear warmer on the user's head. The band portion and the ear portions act together as a biased clamp. If an ear portion is rigid or substantially rigid, the clamping pressure or force applied on the user's head by the ear portion is localized proximate to the uppermost and/or lowermost points on the ear portion. If the clamping pressure or force is applied over a small area, the pressure may become uncomfortable for the user.

Different embodiments of the ear warmer apply different amounts of pressure or force to a user's head. Additionally, different embodiments of the ear warmer apply the pressure or force to different locations on the user's head. Specifically, the pressure and pressure location can be adjusted between different embodiments of the ear warmer by modifying the band portion and/or the ear portions. In other words, the amount of pressure applied and the pressure location for one embodiment of an ear warmer is different than the amount of pressure applied and the pressure location for an ear warmer of another embodiment. For example, the applied pressure for one embodiment is less than or greater than the applied pressure for another embodiment having lesser or greater, respectively, the thickness and/or width of the band portion, but substantially equal thickness and width of the ear portions. Alternatively, the applied pressure for one embodiment having ear portions of a certain thickness is less than the applied pressure for another embodiment having ear portions of a lesser thickness. Additionally, one embodiment of an ear portion has a certain thickness and is less flexible than an ear portion of another embodiment having a thickness greater than the thickness of the ear portion of the one embodiment. Additionally, one embodiment of an ear portion has a certain thickness and applies pressure or force to a user's head over a smaller area than an embodiment of an ear portion having a lesser thickness than the ear portion of the one embodiment. Embodiments of ear portions which apply pressure to a large area of a user's head is more comfortable than embodiments of ear portions that apply pressure to a small area of the user's head.

The pressure that is applied by an ear warmer of a particular embodiment to a user's head over a particular area is a function of the thickness of the material and the surface area dimension over that area of the ear portion. For example, if one embodiment of the ear warmer is manufactured with an ear portion that is thinner than an ear portion of a further embodiment, then the clamping pressure produced by the ear warmer of the one embodiment will be less than the clamping pressure produced by the ear warmer of the further embodiment. Additionally, if one embodiment of the ear warmer is manufactured with a smaller overall size then the overall size of the ear warmer of a further embodiment, then the clamping pressure produced by the ear warmer of the one embodiment will be less than the clamping pressure produced by the ear warmer of the further embodiment. The ear warmer, however, should apply sufficient pressure to the user's head retain the ear warmer on the user.

Additionally, the clamping pressure and the location of the pressure can differ among different embodiments of an ear warmer by providing the ear portion with a curved configuration. Specifically, the configuration of the ear portion affects where the ear portion flexes when the ear warmer is placed on a user's head. For example, if one embodiment of the ear warmer is manufactured with an ear portion that is substantially flat (for example, having only a small curved portion), then, when forces are applied to the ear warmer, the ear portion will bend and flex at its weakest point or where it curves. Alternatively, if another embodiment of the ear warmer is manufactured with an ear portion that has a curved configuration (for example, having a substantial amount of the ear portion being curved), then, when forces are applied to the ear warmer, the ear portion will bend and flex over a substantial portion of the ear portion. As the flexible area or curved portion of the ear portion increases, the bending forces are distributed over a larger portion of the ear portion. A larger distribution of bending forces reduces the potential for a stress failure on the ear portion because the bending forces are spread out over a larger portion of the ear portion. An increase in the range of curvature and the flexibility of the ear portion also results in a more uniform distribution of the clamping force on the user's head. Additionally, as the curved portion of the ear portion is increased (between different embodiments of the ear warmer), the pressure applied by the ear warmer to the head of a user at any one location is decreased. In one embodiment of an ear warmer, the ear portion has a distal end disposed inwardly of its coupling to the band portion in its deployed configuration. The term "inwardly" is used herein to mean towards a user's head when the ear warmer is worn by a user or towards a point disposed such that the inner side of the ear portion is disposed between the point and the outer side of ear portion.

The increase in curvature of the ear portions also results in a smaller collapsed configuration of the ear warmer when the ear portions are moved to their collapsed positions relative to the band portion. When the ear warmer is collapsed, the distal end of each ear portion is disposed proximate to or extends slightly beyond the opposite end of the band portion than that to which the particular ear portion is coupled. The overall result is a lower and narrower profile of the ear warmer in its collapsed configuration.

In several embodiments of an ear warmer according to this invention, the amount of the ear portion that is curved is greater than other known ear warmers. Additionally, the profile or distance that the ear warmer extends from the user's head is also modified to achieve a different (such as a more comfortable) fit on the user's head. It can be appreciated that either or both of the curvature and the profile of a particular embodiment of an ear warmer can be different than the curvature and the profile of another embodiment of an ear warmer.

Returning to the embodiment of the ear warmer illustrated in FIGS. 50 through 59. The first ear portion 2102 of the frame 2100 and the second ear portion 2104 of the frame 2100 are functionally and structurally similar. Therefore, only the first ear portion 2102 is discussed in detail.

Figure 55:
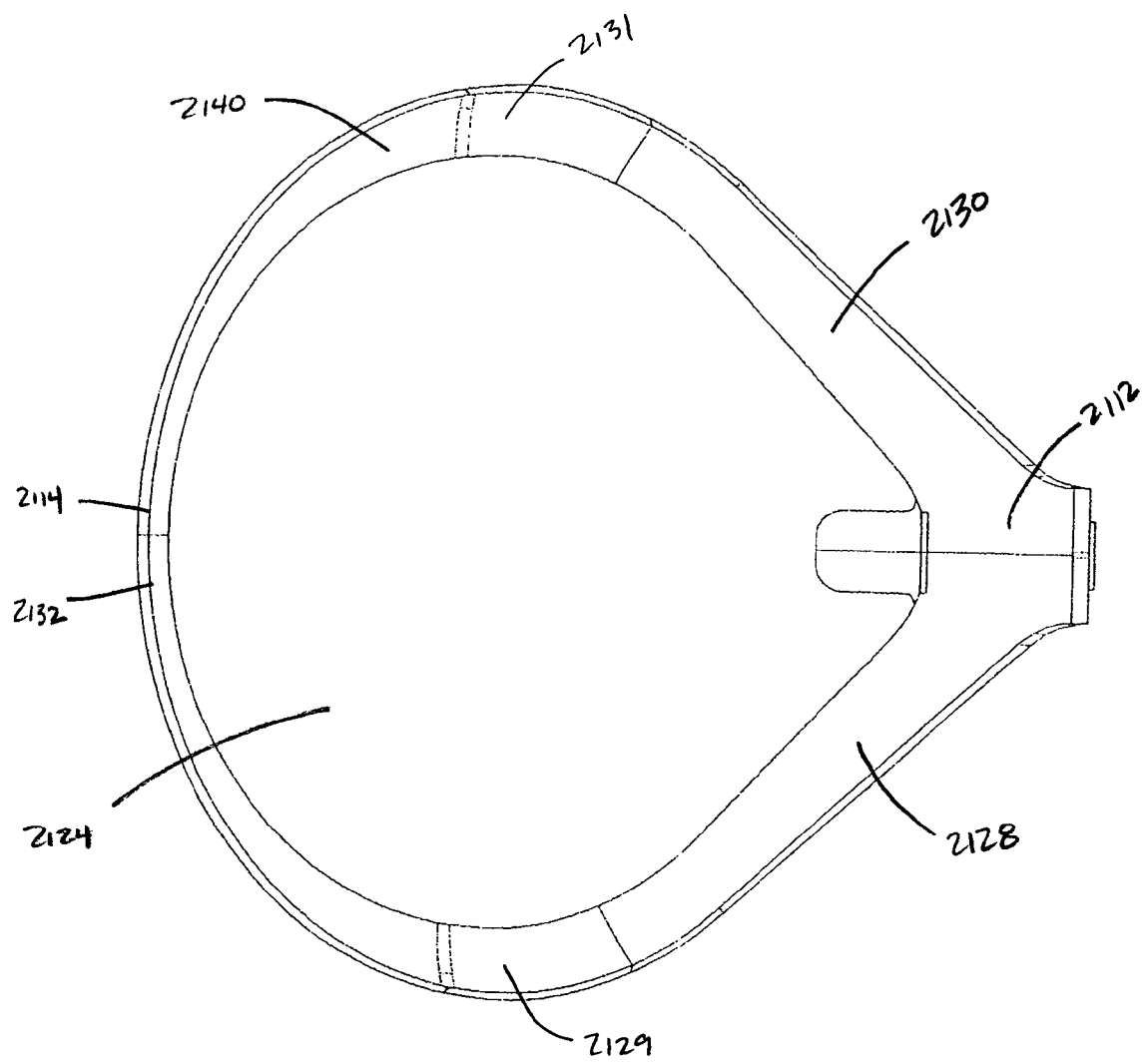
FIG. 55 is an inner side view of the ear portion illustrated in FIG. 51.
Figure 56:
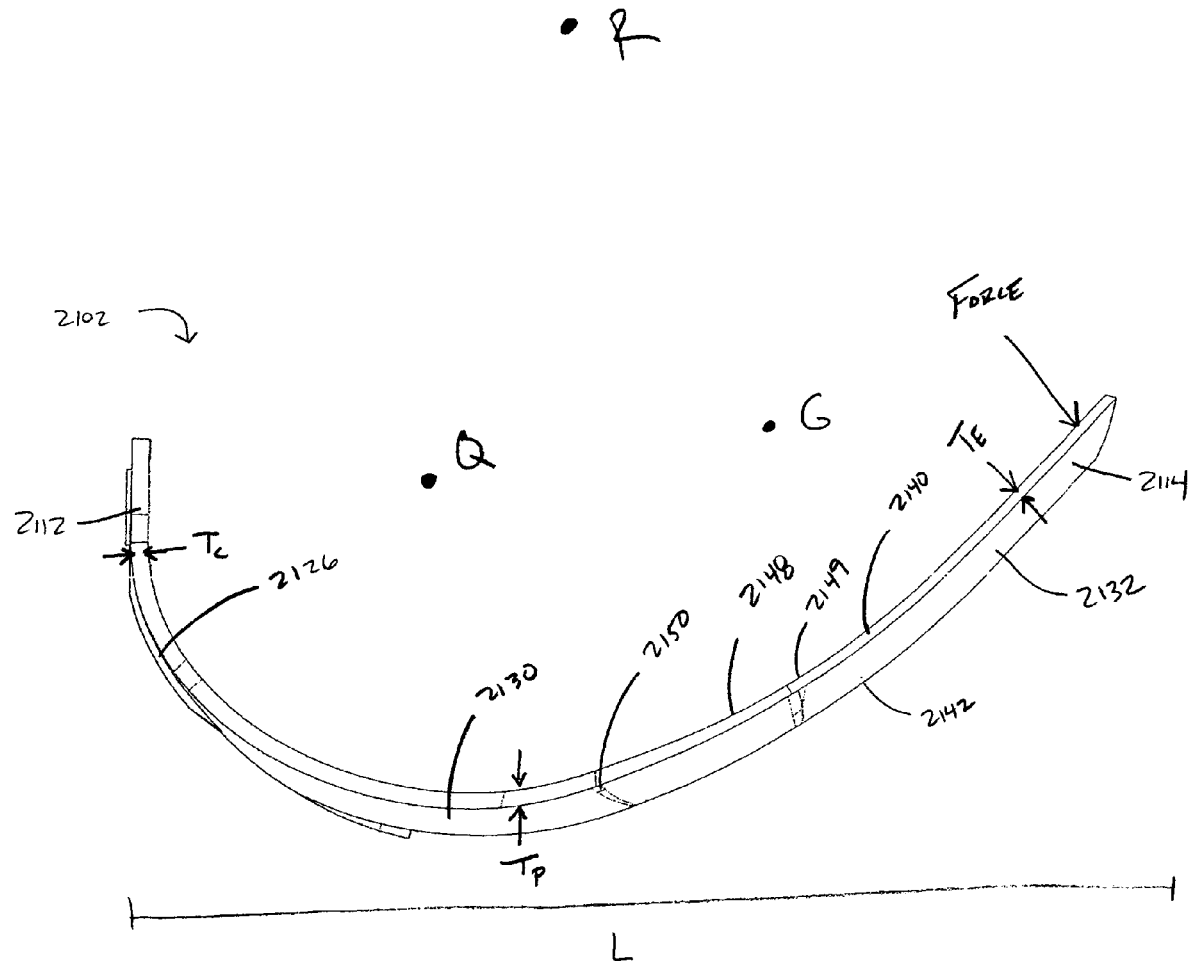
FIG. 56 is a top view of the ear portion illustrated in FIG. 51.
Figure 57:
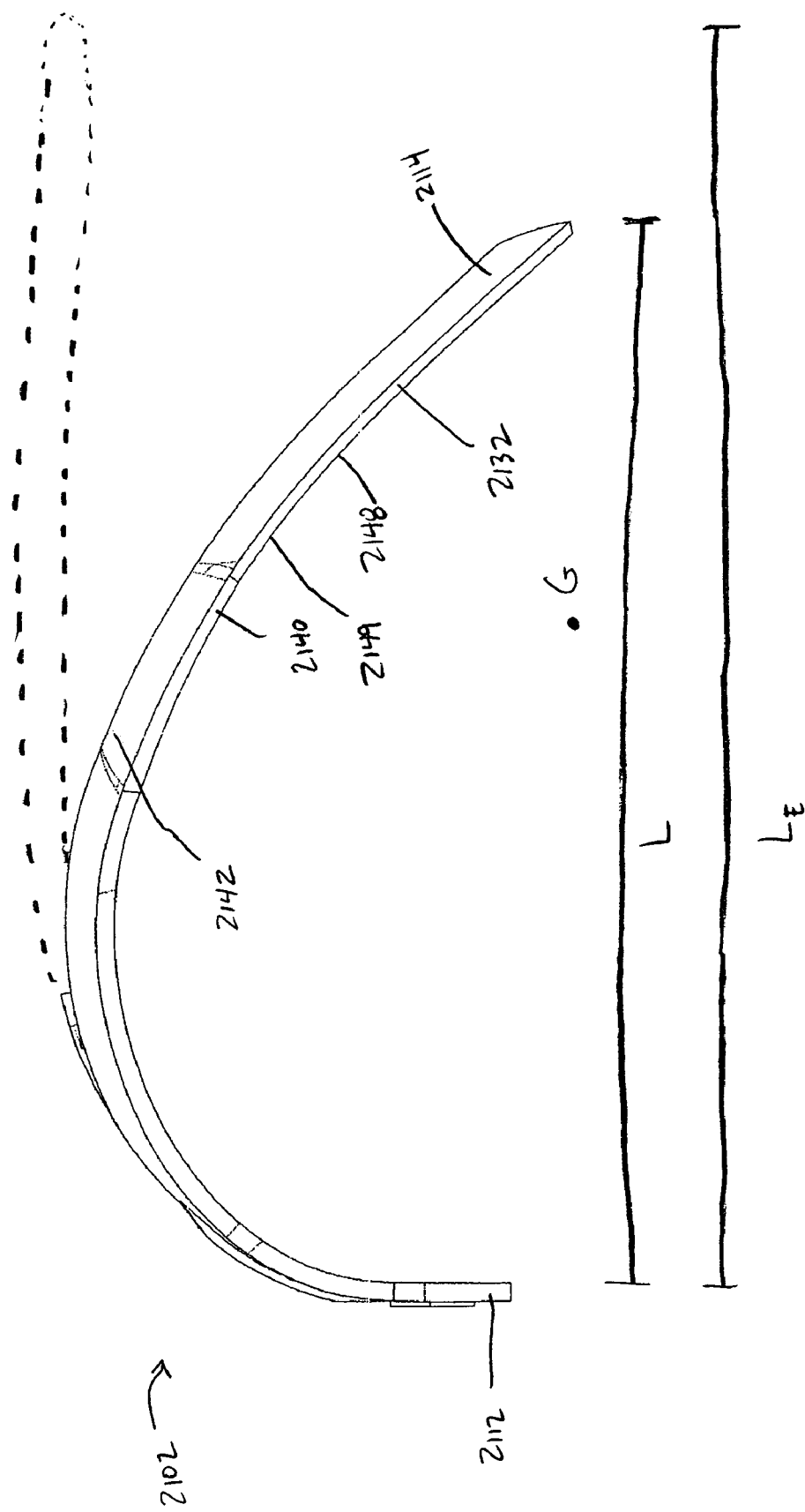
FIG. 57 is a bottom view of the ear portion illustrated in FIG. 51.

An embodiment of an ear portion is illustrated in FIGS. 51 through 57. In this embodiment, the first ear portion 2102 includes a coupling portion 2126, a first projecting portion 2128, a second projecting portion 2130, and an extension member or portion 2132. The first ear portion 2102 includes an opening 2124 that is defined by the first projecting portion 2128, the second projecting portion 2130 and the extension portion 2132. The first ear portion 2102 is curved such that the second end portion 2114 extends downwardly farther than the first end portion 2112 as illustrated in FIG. 57.

In one embodiment, the first projecting portion and the second projecting portion are structurally and functionally similar. In another embodiment, the first projecting portion and the second projecting portion are not structurally and functionally similar. For example, one of the projecting portions can be thicker than the other projecting portion to achieve a different spreading and intensity of pressure on a user's head such as the upper or lower side of the ear portion when worn by a user. Also, the length of one of the projecting portions can be different than the other projecting portion to achieve a different positioning of the ear portion on the user's head. Moreover, one or both of the projecting portions can be substantially linear, partially or substantially curved, or have any other shape or configuration.

In one embodiment of an ear portion, the first and second projecting portions extend from the coupling portion symmetrically about an axis along the coupling portion. For example, the first and second projecting portions can be substantially linear and can extend from the coupling portion to form an acute angle. Alternatively, the first and second projecting portions can be curved or have curved portions. In another embodiment, the first and second projecting portions do not extend from the coupling portion symmetrically.

In one embodiment, the first and second projecting portions and the extension member collectively have a frusto-conical configuration. In alternative embodiments, these parts collectively may have a different shape or configuration. Also, each of these parts may have an oval cross-section that is vertically upright or inclined, a circular cross-section, or a square or rectangular shaped cross-section. Different cross-sectional configurations of the projecting portions and the extension member result in different amounts and locations of pressure on the user's head.

The coupling portion 2126 is disposed adjacent to and is coupled to the band portion 2106 of the frame 2100. In this embodiment, the coupling portion 2126 of the first ear portion 2102 includes an mounting opening 2127 that is configured to receive a connector 2120 to couple the first ear portion 2102 to the band portion 2106.

The first projecting portion 2128 and the second projecting portion 2130 are each coupled to and extend from the coupling portion 2126. The extension portion 2132 extends between the ends of the first projecting portion 2128 and the second projecting portion 2130.

Figure 54:
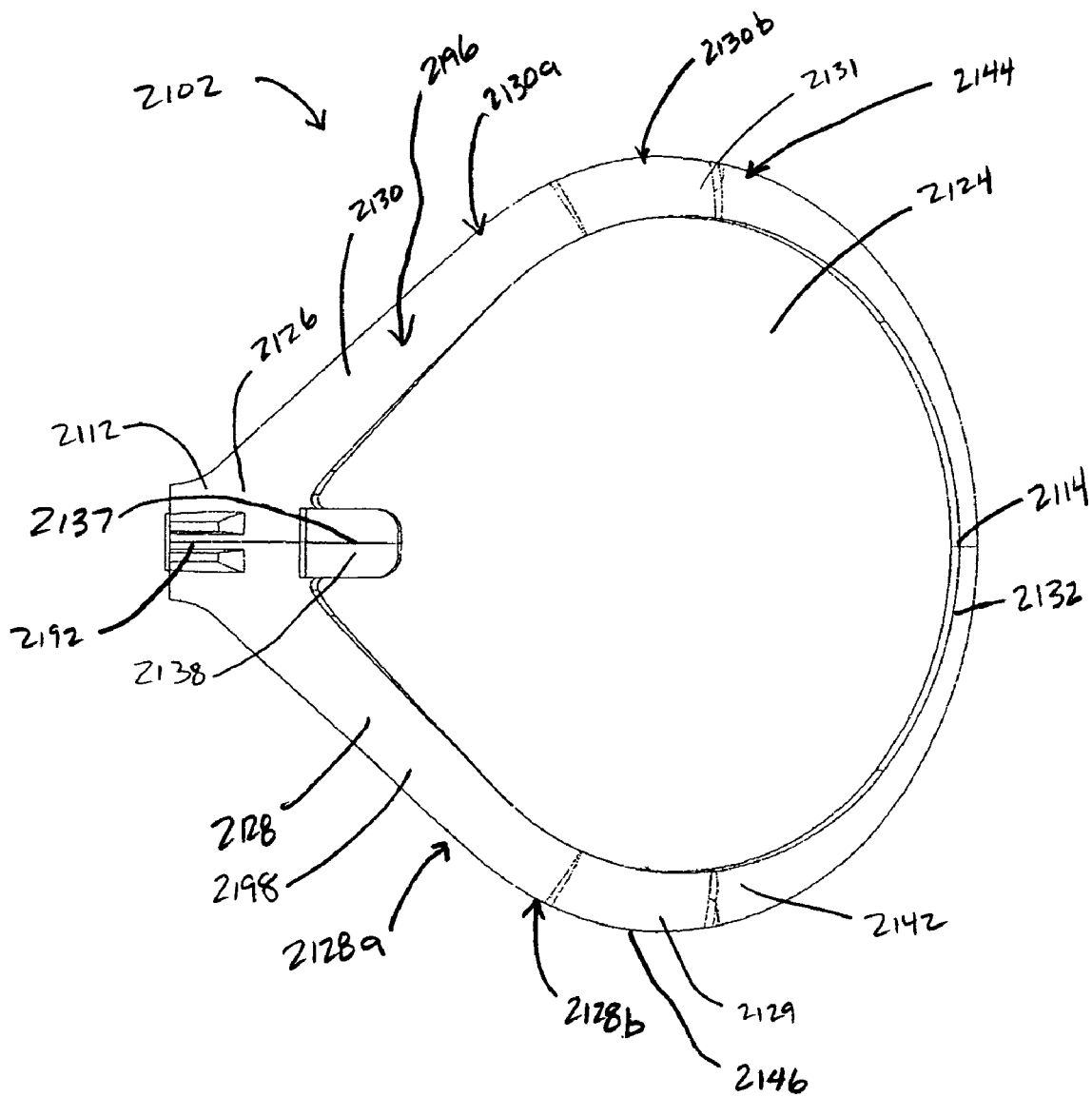
FIG. 54 is an outer side view of the ear portion illustrated in FIG. 51.

In this embodiment, the first projecting portion 2128 is coupled to the extension member 2132 proximate to the lowermost point 2129 of the first ear portion 2102 (see FIG. 54). The lowermost point 2129 of the first ear portion 2102 is the lowermost point of the first ear portion 2102 when the ear warmer 2000 is disposed on a head of a user. Similarly, the second projecting portion 2130 is coupled to the extension member 2132 proximate to the uppermost point 2131 of the first ear portion 2102. The uppermost point 2131 of the first ear portion 2102 is the uppermost point of the first ear portion 2102 when the ear warmer 2000 is disposed on a head of a user. In an alternative embodiment, the first projecting portion is coupled to the extension member at a location different than the lowermost point. In another embodiment, the second projecting portion is coupled to the extension member at a location different than the uppermost point of the first ear portion.

Although points on the first ear portion 2102 have been identified as uppermost and lowermost it should be understood that there may be, for example, several uppermost points of the first ear portion. In such a case, the "uppermost point" includes the several points. Similarly, there may be several lowermost points of the first ear portion. In such a case, the "lowermost point" includes the several points. It should be understood that the uppermost point and the lowermost point are fixed points on the ear portion and do not change according to the orientation of the frame at any given time.

In one embodiment, each of the first projecting portion 2128 and the second projecting portion 2130 has a substantially linear portion 2128a and 2130a (adjacent the coupling portion 2126) and a slightly curved portion 2128b and 2130b (adjacent the extension member 2132) when viewed from the side of the first ear portion (see FIGS. 54 and 55). In alternative embodiments, the first projecting portion and the second projecting portion are linear and do not include curved portions when viewed from the side of the first ear portion.

In one embodiment, the coupling portion 2126, the first projecting portion 2128, the second projecting portion 2130, and the extension member 2132 are unitarily (or monolithically) formed. In other words, the portions 2126, 2128, and 2130 and the extension member 2132 of the first ear portion 2102 are made of a singe piece of material.

The first ear portion 2102, including the portions 2126, 2128, and 2130 and the extension member 2132, can be manufactured by injection molding. Injection molding involves the introduction of the molten material, such as a plastic, into a mold. The molten material is inserted through an opening in the mold and fills the cavities in the mold. The location on the molded article that corresponds to where the molding material is inserted into the mold can be referred to as the molding gate. The molding gate represents a location or portion of the molded article that is more likely to fail or break due to stress than other locations or portions of the molded article. If the molding gate is located along any of the coupling portion 2126, the first projecting portion 2128, the second projecting portion 2130 and the extension member 2132, the ear portion may break at or near the molding gate during ordinary use of the ear warmer. Accordingly, by locating the molding gate on part of the ear portion that is offset from any of the portions 2126, 2128 and 2130 and extension member 2132, the potential for a failure or fracture during ordinary use of the ear warmer may be reduced.

Figure 51:
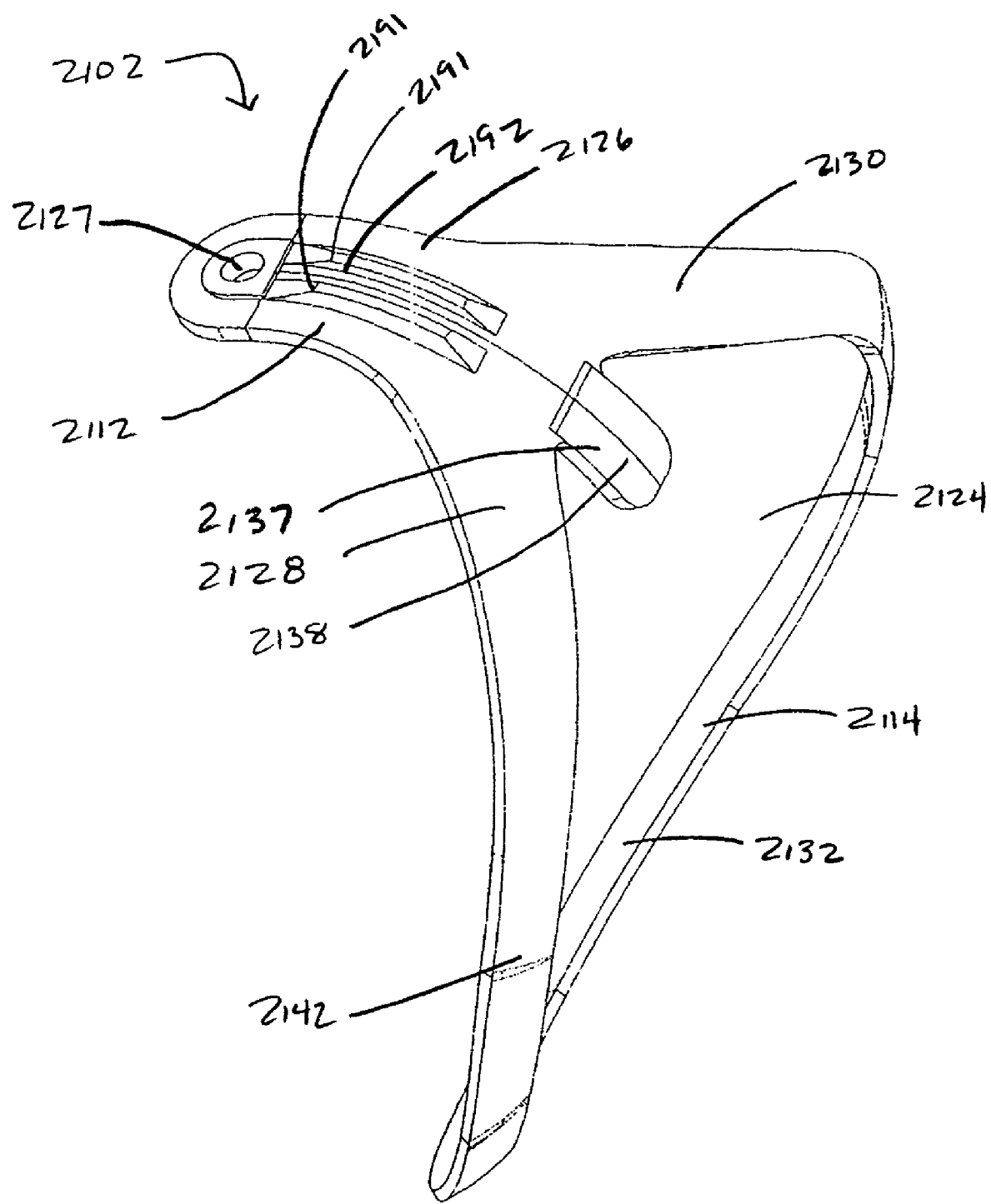
FIG. 51 is a perspective view of an ear portion of the frame illustrated in FIG. 50.

In the illustrated embodiment, the ear portion includes a projection 2137 that extends into the opening 2124 defined by the ear portion 2102. The molding gate 2138 is disposed or located on the projection 2137 as illustrated in FIGS. 51 and 54. In alternative embodiments, the molding gate can be located on a projection or other structure that is coupled to the ear portion at any location. For example, the projection that includes the molding gate can be coupled to the coupling portion, the first or second projecting portions, or the extension member or portion.

In alternative embodiments, the portions and the extension member of the first ear portion are several different individual pieces and are fixedly coupled to one another via a conventional coupling mechanism such as an adhesive, screws, or rivets.

Figure 52:
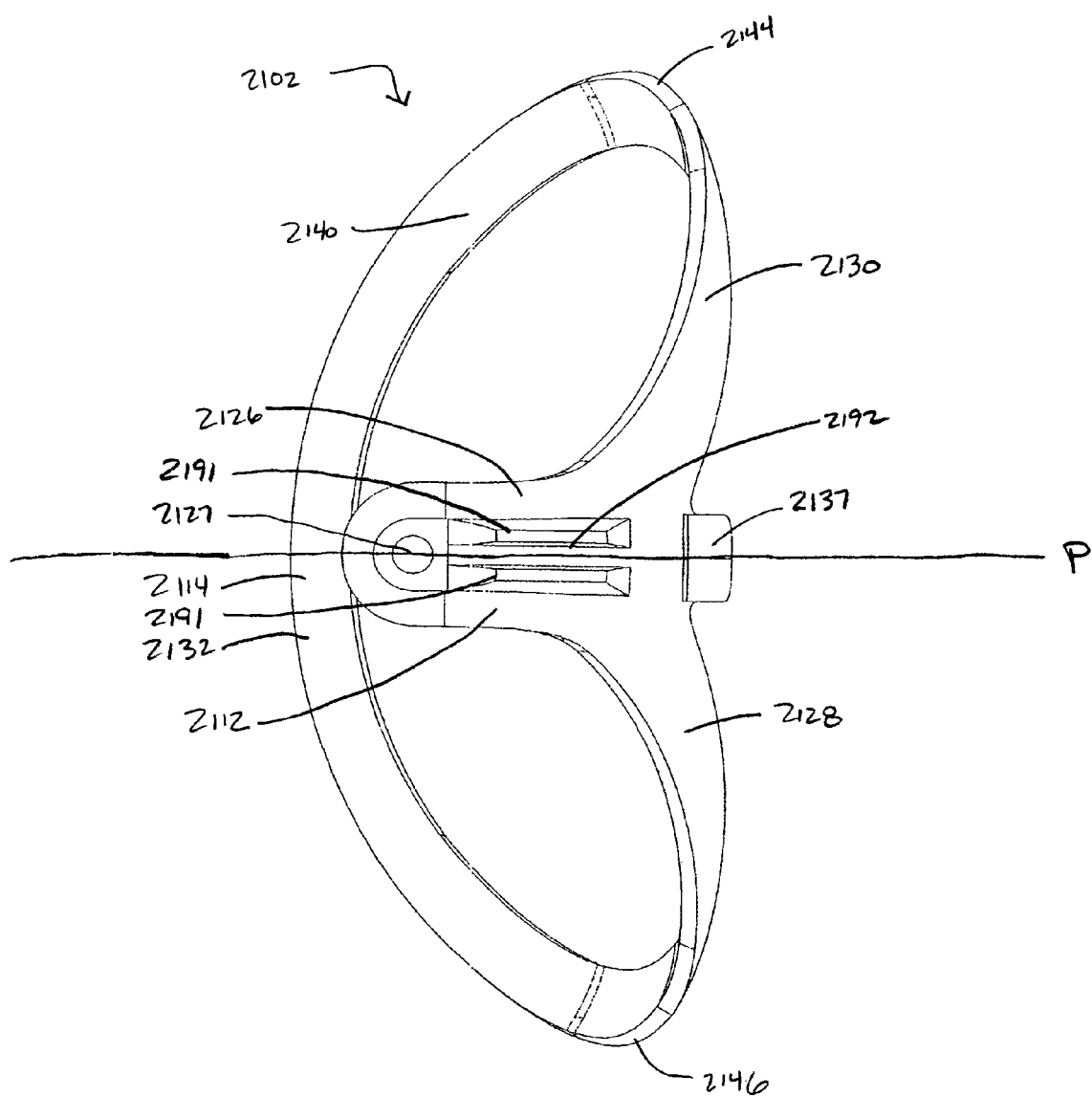
FIG. 52 is a rear view of the ear portion illustrated in FIG. 51.
Figure 53:
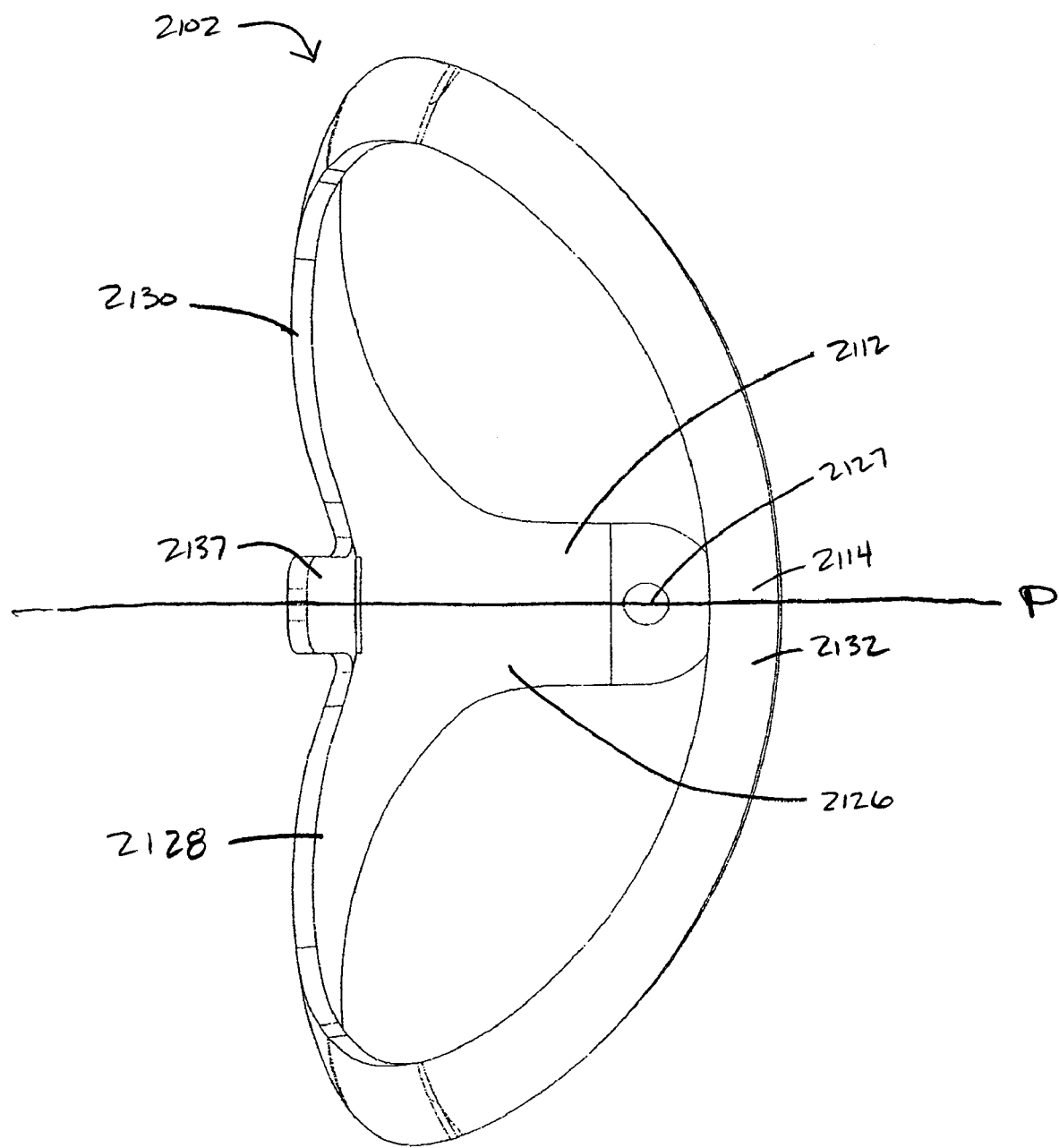
FIG. 53 is a front view of the ear portion illustrated in FIG. 51.

As illustrated in FIGS. 56 and 57, the first ear portion 2102 has a length L that extends from the first end portion 2112 of the first ear portion 2102 to the second end portion 2114 of the first ear portion 2102. As illustrated in FIGS. 52 and 53, the first ear portion 2102 also has a longitudinal plane P that extends from the first end portion 2112 to the second end portion 2114 along the length L. The first ear portion 2102 has an outer side 2142, an inner side 2140 (the side proximate the user's head and disposed between outer side 2142 and a user when the ear warmer is worn by the user), an upper side 2144 (see FIGS. 52 and 54— the side that faces up when the ear warmer is worn by a user), and a lower side 2146 (see FIGS. 52 and 54— the side opposite the upper side 2144 and that faces down when the ear warmer is worn by a user). The first ear portion 2102 also has an innermost surface or edge 2148. The innermost surface 2148 of the first ear portion 2102 is the portion or surface of the inner side 2140 of the first ear portion 2102 that is disposed closest to a user's head when the ear warmer is worn by the user. In one embodiment, the innermost surface 2148 extends along a perimeter of the first ear portion 2102. For example, in one embodiment, the innermost surface 2148 extends along an outer perimeter of the first ear portion. In an alternative embodiment, the innermost surface 2148 extends along an inner perimeter of the first ear portion.

In one embodiment, the first ear portion 2102 has a thickness dimension that is defined by the distance at a particular location on the first ear portion 2102 between the inner side 2140 and the outer side 2142. As illustrated in FIG. 56, the thickness dimension can vary along the length of the first ear portion 2102. In particular, the thickness dimension of the first ear portion varies along the first and second projecting portions 2128 and 2130 and the extension member 2132. A representative thickness dimension of the coupling portion 2126 is designated as $T_C$ in FIG. 56. Similarly, representative thickness dimensions of the projecting portions and the extension member 2132 are designated as $T_P$ and $T_E$, respectively. In this embodiment, $T_C$ is substantially the same as $T_P$, which is greater than $T_E$. Thus, the coupling portion 2126 is the thickest portion of the ear portion 2102 and the ear portion 2102 is tapered from the projecting portions 2126 and 2128 to the distal end 2114 of the ear portion 2102. The tapered configuration of the ear portion 2102 allows the ear portion 2102 to flex differently over various locations on the ear portion when the ear warmer 2000 is disposed on a user's head. In other words, the reduced thickness of the ear portion enables the ear portion to flatten out against the user's head when the ear warmer is disposed on a user's head. Thus, the forces that are applied by the ear warmer 2000 on the user's head is spread over a large portion of the ear portion 2102. Therefore, the force applied by the ear warmer 2000 on the user's head at any one point of the ear portion 2102 is less than would be otherwise be the case if the ear portion did not have a tapered configuration.

In an alternative embodiment, the ear portion can include a stepped taper as opposed to a gradual taper. In another embodiment, the ear portion can include a reverse taper with the extension member having a greater thickness than the coupling portion. In another embodiment, the thickness can vary. In another embodiment, the thickness of the coupling portion is greater than the thickness of the projecting portions, which in turn is greater than the thickness of the extension member.

As previously discussed, when a user wears the ear warmer 2000 on the user's head, the ear portions 2102 and 2104 are disposed proximate to the user's head. The ear warmer 2000 may have one or more layers of fabric coupled thereto. The shape of the ear portions and the band portion direct the ear portions inwardly to provide a clamping force on the user's head.

A substantial section of each ear portion (such as 50% or more of the length of the ear portion) contacts the user's head when the ear warmer is disposed on a user's head. In one embodiment, more than 50% of the length of the ear portion contacts the user's head when the ear warmer is disposed on the user's head. In particular, as illustrated in FIG. 54, the part of the first ear portion 2102 that extends continuously from approximately point 2196 on second projecting portion 2130, around extension member 2132, and to approximately point 2198 on first projecting portion 2128 is disposed proximate to the user's head when the user wears the ear warmer. This part of the first ear portion 2102 is a substantial portion of the extent or perimeter of the first ear portion 2102. Accordingly, pressure is applied to the user's head along this part of the first ear portion 2102 from point 2196 to point 2198.

The following data is only representative of several examples of an ear portion and is not intended to be limited in any respect. In one embodiment, the thicknesses $T_C$ and $T_P$ are approximately 0.057 inches (1.45 millimeters) and thickness $T_E$ at the distal end is approximately 0.035 inches (0.89 millimeters). In another embodiment, the thicknesses $T_C$ and $T_P$ are approximately 0.054 inches (1.37 millimeters) and thickness $T_E$ is approximately 0.033 inches (0.84 millimeters). In one instance, the change from a thickness of 0.057 inches (1.45 millimeters) to a thickness of 0.054 inches (1.37 millimeters) for $T_C$ and $T_P$ results in the distal or second end of the ear portion applying a one ounce less of force to the user's head.

In some embodiments of an ear warmer, the range of force applied by the distal end of the ear portion to the user's head is approximately six to sixteen ounces. In some embodiments, the pressure applied by the distal or second end of the ear portion to the head is in the range of nine to twelve ounces. The amount of pressure applied by the distal end portion of the ear portion is measured with the band portion disposed at a mid-length (when the band portion is disposed at the middle of its range of motion).

As illustrated in FIG. 56, the first ear portion 2102 includes several different curved portions. Specifically, in the illustrated embodiment, the first end portion 2112 of the first ear portion 2102 is substantially linear. Additionally, a middle portion 2150 of the first ear portion 2102, which is disposed between the first end portion 2112 of the first ear portion 2102 and the second end portion 2114 of the first ear portion 2102, and the second end portion 2114 of the first ear portion 2102 have a curved shape or configuration, as illustrated in FIGS. 56 and 57, when the ear warmer is in an unbiased condition. The term "unbiased" is used herein to mean without the application of an external force or pressure. In other words, the ear warmer is in its unbiased condition when it is at rest and does not have a user applied force, such as by a user's head or other body part, applied to it. The middle portion 2150 and the second end portion 2114 curve toward or are concave with respect to a point G that is disposed at a location apart from the first ear portion 2102 such that the inner side 2140 of the first ear portion 2102 is disposed between point G and the outer side 2142 of the first ear portion 2102. In other words, the first ear portion 2102 is curved such the second end portion 2114 of the first ear portion 2102 is configured to be disposed closer to a user's head, or to place more pressure on the user's head, than the first end portion 2112 of the first ear portion 2102. This enables the pressure applied by the second or distal end of the first ear portion to the user's head to be less. This configuration also directs the frame pressure toward the distal end 2114 of the ear portion.

In one embodiment, a substantial amount (such as 50% or more) of the first ear portion 2102 along its length L, including part or all of the projecting portions and all of the extension member, is curved inwardly toward the inner side 2140 of the first ear portion 2102. In other embodiments, less than a substantial amount of the length L of the first ear portion 2102 is curved. As illustrated by the dashed line in FIG. 57, the ear portion 2102, in one example, has a length $L_E$ when the ear portion 2102 is flexed such that the ear warmer 2000 may be disposed on a user's head.

In one embodiment, the different parts of the first ear portion 2102 have different radii of curvature. In other words, one part of the first ear portion 2102 has a first radius of curvature and another part of the first ear portion 2102 has a second radius of curvature different from the first radius of curvature. Specifically, a first part or section of the curved portion, corresponding in part to the first and second projecting portions, is curved about a first axis Q and has a radius of curvature. The first axis Q is disposed substantially orthogonal to the longitudinal plane P of the ear portion. The second part or section of the curved portion, corresponding to the extension member, is curved about a second axis R and has a radius of curvature different from that of the first part of the curved portion. The second axis R is disposed substantially orthogonal to the longitudinal plane P of the ear portion. In one embodiment, the first axis is spaced apart from the second axis. In this embodiment, the middle portion 2150 of the first ear portion 2102 has a first radius of curvature. Similarly, the second end portion 2114 of the first ear portion 2102 has a second radius of curvature, which is greater than the first radius of curvature. In an alternative embodiment, the curved portion of the first ear portion has a constant radius of curvature. In another embodiment, the first radius of curvature is greater than the second radius of curvature.

In one embodiment, the sum of the length of the first curved portion of the ear portion and the length of the second curved portion of the ear portion is half of the length of the ear portion. In another embodiment, the sum of the length of the first curved portion and the length of the second curved portion of the ear portion is two-thirds the length of the ear portion. In a further embodiment, the sum of the length of the first curved portion of the ear portion and the second curved portion of the ear portion is four-fifths the length of the ear portion. In a further embodiment, the sum of the length of the first curved portion of the ear portion and the length of the second curved portion of the ear portion is equal to the length of the ear portion.

In the illustrated embodiment, the extension member 2132 includes an innermost surface or edge 2149 which is a portion of the innermost surface 2148 of the first ear portion 2102. The innermost surface 2149 of the extension member 2132 is curved toward the inner side 2140 of the first ear portion 2102 and is non-planar. In other words, the innermost surface 2149 of the extension member 2132 has a curved configuration and is not disposed in any one plane. In an alternative embodiment, only a portion of the innermost surface of the extension member is curved.

In one embodiment, a substantial amount (such as 50% or more) of the first ear portion 2102 along its length L of the first ear portion 2102 is configured to flex or bend when the ear warmer 2000 is disposed on a head of a user. In particular, part or all of the projecting portions and the extension member have tapered configurations and curved profiles or configurations that allow the ear portion to flex or bend. The curved configuration of the ear portion 2102 results in the flexing of the ear portion along the length of the ear portion, thereby distributing the flexing forces along a substantial portion of the length of the ear portion. When the ear warmer 2000 is disposed on the user's head, a clamping force is applied to the user's head and the reactionary force on the ear portion 2102 is shown in FIG. 56. The curvature of the ear portion 2102 alone or in combination with other features of the ear portion 2102 allow the ear portion to flex along a substantial portion of its length (such as 50% or more) when the ear warmer 2000 is disposed on a head of a user. The flexing is also enhanced by the reduced thickness of the ear portion. Thus, as pressure is applied to the ear portion, the ear portion flattens out so that an increased amount of the ear portion is proximate to and applying pressure to the user's head and more pressure is applied to the end 2114. In particular, the extension member can follow the contour of the face and bone structure of the user. The first ear portion 2102 in its flexed configuration is illustrated in FIG. 57 in dashed lines.

Thus, a substantial amount of the length L of the first ear portion 2102 conforms to and applies pressure to a side of a head of a user when the ear warmer 2000 is disposed on the user's head. In other embodiments, the extent of the ear portion that is configured to flex when the ear warmer is disposed on a head of a user can vary. In other words, the extent of the ear portion of one embodiment that is configured to flex when the ear warmer is disposed on a head of a user may be different than the extent of the ear portion of another embodiment that is configured to flex when the ear warmer is disposed on a head of a user in a different embodiment. For example, in one embodiment, only the extension member bends or flexes. In alternative embodiments, the other parts of the ear portion can bend or flex.

As discussed above, the extension member 2132 is configured to flex or bend when the ear warmer 2000 is disposed on a head of a user. The extension member 2132 is configured to conform to the shape of a head of a user to comfortably secure the ear warmer 2000 to the head of the user. In one embodiment, the projecting portions and the extension member collectively have a frusto-conical configuration. The extension member and the projecting portions flatten out as the ear portion contacts the user's head. In an alternative embodiment, only a portion of the extension member is configured to flex or bend when the ear warmer is disposed on a head of a user. In a further embodiment, the extension member is not configured to flex or bend when the ear warmer is disposed on a head of a user. Rather, another portion of the frame such as the band portion is configured to flex.

Figure 57A:
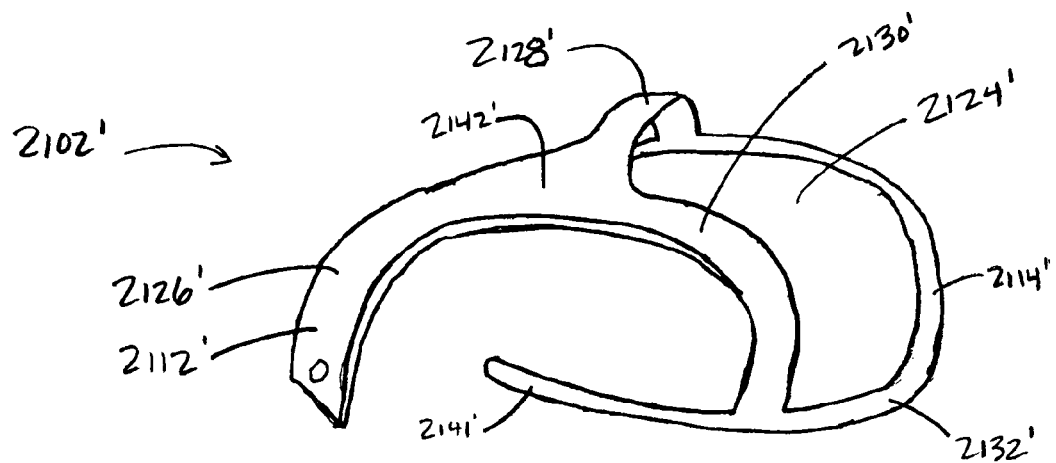
FIG. 57A is a perspective view of an ear portion for a frame of an ear warmer according to an embodiment of the invention.
Figure 57B:
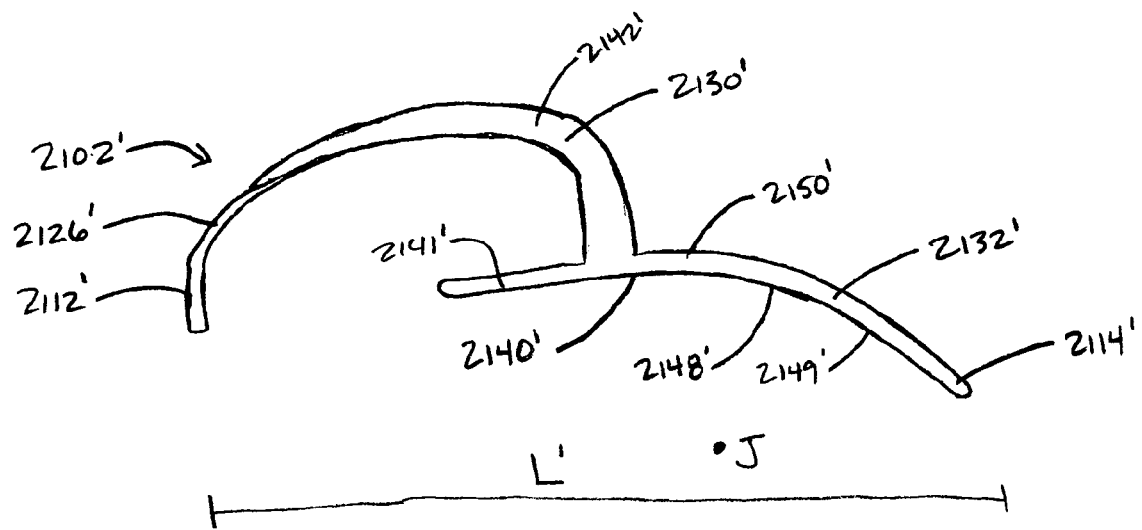
FIG. 57B is top view of the ear portion illustrated in FIG. 57A.

Referring to FIGS. 57A and 57B, an embodiment of an ear portion for a frame of an ear warmer is illustrated. The ear portion 2102' defines an opening 2124' and includes a coupling projection 2126', a first support projection or projecting portion 2128', a second support projection or projecting portion 2130', and an extension member or portion 2132'. The first support projection 2128' and the second support projection 2130' are each coupled to and extend from the coupling projection 2126'. The extension member 2132' is coupled to the first support projection 2128' and to the second support projection 2130'. In one embodiment, the extension member 2132' can have a substantially circular cross-section. In another embodiment, the extension member 2132' can have any type of cross-section, such as rectangular or triangular.

The ear portion 2102' includes a length L' that extends from a first end portion 2112' of the ear portion 2102' to a second end portion 2114' of the ear portion 2102'. The ear portion 2102' has an outer side 2142' and an inner side 2140' (the side disposed between outer side 2142' and a user when the ear warmer is worn by the user). The ear portion 2102' also has an innermost surface 2148'. The innermost surface 2148' of the ear portion 2102' is the portion or surface of the inner side 2140' of the ear portion 2102' that forms the inner edge of the ear portion 2102' and is disposed closest to a user's head when the ear warmer is worn by the user.

Referring to FIG. 57B, the ear portion 2102' includes several different curved portions. Specifically, the first end portion 2112' of the first ear portion 2102' is substantially linear. Additionally, in the illustrated embodiment, a middle portion 2150' of the ear portion 2102', which is disposed between the first end portion 2112' of the ear portion 2102' and the second end portion 2114' of the first ear portion 2102', and the second end portion 2114' of the first ear portion 2102', have a curved shape. The middle portion 2150' and the second end portion 2114' curve toward a point J that is disposed at a location apart from the first ear portion 2102' such that the inner side 2140' of the first ear portion 2102' is disposed between point J and the outer side 2142' of the first ear portion 2102'. In other words, the ear portion 2102' is curved such that the second end portion 2114' of the first ear portion 2102' is configured to be disposed closer to a user's head, or to place more pressure on the user's head, than the first end portion 2112' of the ear portion 2102'.

In this embodiment, a substantial amount of the length L' of the ear portion 2102' is curved toward the inner side 2140' of the ear portion 2102'. In other embodiments, less than a substantial amount of the length L' of the ear portion 2102' is curved.

In this embodiment, the curved portions of the first ear portion 2102' do not form a continuous curve. Specifically, a first part of the curved portion is curved about a first point and the second part of the curved portion is curved about a second point. The first part or section of the curved portion has multiple radii of curvature and the second part or section of the curved portion has its own radius of curvature, which is different than any of the radii of curvature of the first part or section.

The extension member 2132' includes an innermost surface 2149' which is a portion of the innermost surface 2148' of the ear portion 2102'. The innermost surface 2149' of the extension member 2132' is curved toward the inner side 2140' of the first ear portion 2102' and is non-planar. In other words, the innermost surface 2149' of the extension member 2132' is not disposed in any one plane. In this embodiment, the extension member includes a rear portion 2141' that is substantially linear and that extends beyond the coupling point with portion 2130'. In alternative embodiments, the entire extension member is curved. In other words, the extension member does not include a linear portion. In an alternative embodiment, the extension member 2132' does not include rear portions 2141' that extend beyond portions 2128' and 2130'.

A substantial amount (such as 50% or more) of the length L' of the extension member 2132' is configured to flex or bend when the ear warmer is disposed on a head of a user. Thus, a substantial amount of the length L' of the extension member 2132' is configured to conform to and apply pressure to a side of a head of a user when the ear warmer is disposed on a user's head.

The innermost surface 2149' of the extension member 2132' is configured to flex or bend when the ear warmer is disposed on a head of a user. In other words, the innermost surface 2149' of the extension member 2132' is configured to conform to the shape of a head of a user to comfortably secure the ear warmer to the head of the user.

Turning to the band portion of the frame, the band portion is configured to extend around a back of a head of a user when the ear warmer 2000 is disposed on the user. Several examples of such a band portions are disclosed in U.S. patent application Ser. No. 10/056,093, filed on Jan. 28, 2002, the disclosure of which is incorporated herein by reference.

Figure 58:
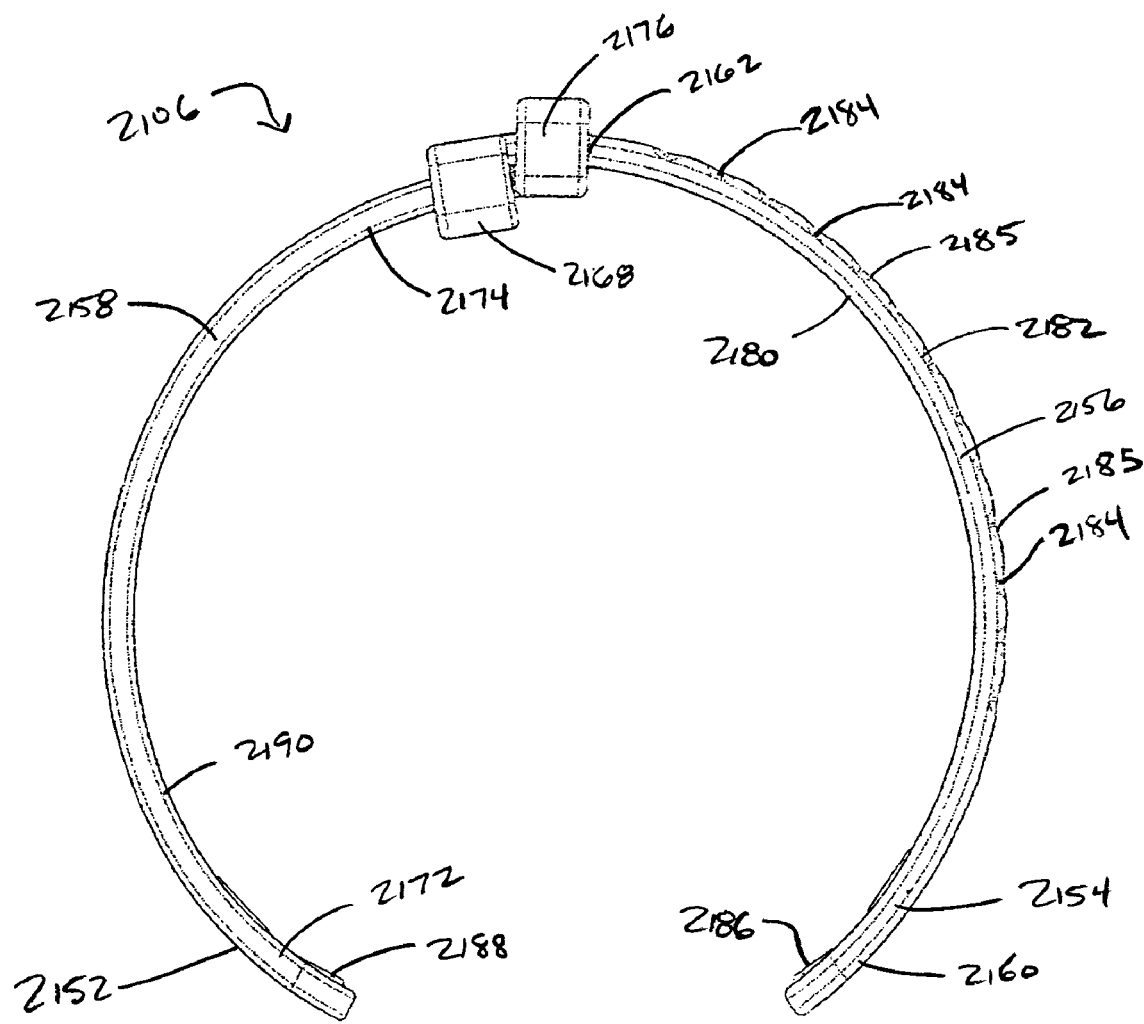
FIG. 58 is a top view of the band portion of the frame illustrated in FIG. 50.
Figure 59:
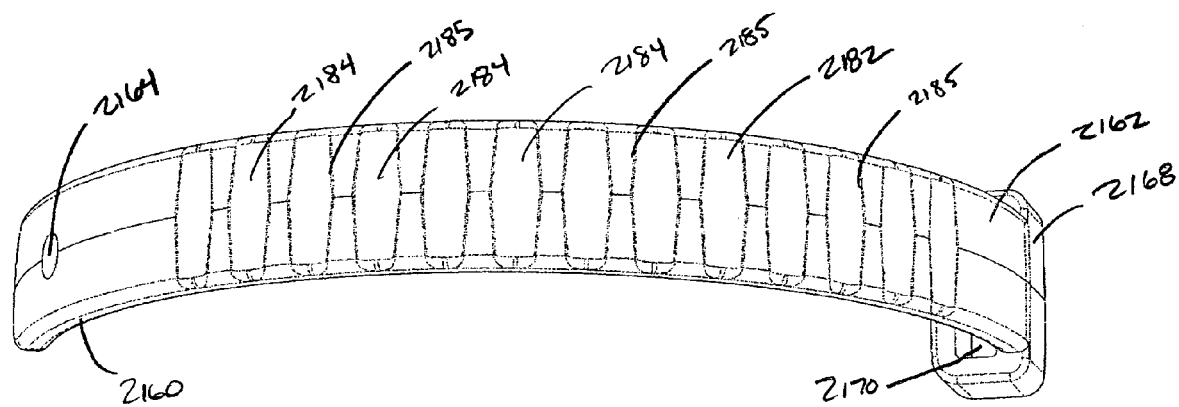
FIG. 59 is a top view of a member of the band portion illustrated in FIG. 58.

FIGS. 58 and 59 illustrate a band portion 2106 of the frame 2100 according to an embodiment of the invention. The band portion 2106 has a first end 2152 and a second end 2154 opposite the first end 2152 of the band portion 2106. The band portion 2106 has a length, which extends from the first end 2152 of the band portion 2106 to the second end 2154 of the band portion 2106. The length of the band portion 2106 may be adjusted by a user to change the length of the band portion 2106 between the first end 2152 of the band portion 2106 and the second end 2154 of the band portion 2106. In other words, the length of the band portion 2106 may be adjusted to change the length of the band portion 2106 between the first ear portion 2102 and the second ear portion 2104. Thus, the size of the ear warmer 2000 may be changed. As the length of the band portion 2106 is changed, the pressure applied by the ear portions varies because the ear portions are disposed at different angles.

As illustrated, the band portion 2106 has a first member 2156 and a second member 2158, which are slidably coupled to one another. The first member 2156 of the band portion 2106 has a curved configuration and includes a first end 2160 and a second end 2162. The first member 2156 has a coupler 2168 disposed proximate the second end 2162 of the first member 2156. The coupler 2168 defines an opening 2170 (see FIG. 59) that is configured to receive the second member 2158 of the band portion 2106, and thereby, slidably couple the second member 2158 of the band portion 2106 to the first member 2156 of the band portion 2106.

Similar to the first member 2156 of the band portion 2106, the second member 2158 of the band portion 2106 has a curved configuration and includes a first end 2172 and a second end 2174. The second member 2158 includes a coupler 2176 disposed proximate the second end 2174 of the second member 2158. The coupler 2176 defines an opening (not illustrated) that is configured to receive the first member 2156 of the band portion 2106, and thereby, slidably couple the first member 2156 of the band portion 2106 to the second member 2158 of the band portion 2106.

In an alternative embodiment, either the first member of the band portion slidably receives the second member of the band portion or the second member slidably receives the first member of the band portion.

In the illustrated embodiment, the couplers 2168 and 2176 are formed unitarily or monolithically with the first member 2156 of the band portion 2106 and the second member 2158 of the band portion 2106, respectively. In an alternative embodiment, the couplers are coupled to the members of the band portion via brads, screws, an adhesive, or any other known coupling mechanism.

The first member 2156 of the band portion 2106 includes an inner side 2180 and an outer side 2182 opposite the inner side 2180. The inner side 2180 of the first member 2156 of the band portion 2106 is disposed between a head of a user and the outer side 2182 when the ear warmer is disposed on the head of the user. The outer side 2182 of the first member 2156 of the band portion 2106 is the side of the band portion that is disposed away from a head of a user when the ear warmer is placed on the head of the user. In one embodiment, the outer side 2182 of the first member 2156 includes an alignment mechanism, such as several ridges or several spaced-apart recesses 2184 formed therein. The recesses 2184 are shallow recesses formed in the first member 2156. The edges 2185 of the recesses 2184 and the recesses 2184 are configured to be engaged by an edge of the coupler 2176 of the second member 2158 that defines the opening of the coupler 2176. The recesses 2184 allow the band portion 2106 to be temporarily retained in several different lengths and configurations. The coupler 2176 engages the edges 2185 and the recesses 2184 of the second member 2158 and provides some resistance to the movement of the first member 2156 of the band portion 2106 relative to the second member 2158. Thus, a user may move or slide the first member 2156 with respect to the second member 2158 to place the band portion 2106 of the ear warmer 2000 in any one of the several different discrete locations. When the ear warmer is put on a user's head, the first ends 2152 and 2160 are spread apart and the friction between the couplers and the band members increases, thereby resisting movement of the members of the band portion relative to each other.

In an alternative embodiment, another surface, such as the inner surface, an upper surface, or a lower surface, of the first member of the band portion includes recesses. In another alternative embodiment, the second member of the band portion includes recesses that are configured to be engaged by the coupler of the first member of the band portion. In a further alternative embodiment, each of the first member and the second member of the band portion includes recesses that are configured to be engaged by the coupler of the second member and the first member, respectively. In another embodiment, the band portions include an alignment mechanism, such as raised areas or ridges.

Openings are disposed proximate the first end of each of the first member and the second member to couple the ear portions 2102 and 2104 to the band portion 2106. For example, as illustrated in FIG. 59, an opening 2164 is disposed proximate the first end 2160 of the first member 2156. The openings 2164 are configured to receive the connectors 2120 and 2122 to pivotally couple the ear portions 2102 and 2104 to the ends 2172 and 2160 of the members 2158 and 2156, respectively. The ear portions 2102 and 2104 can be pivoted from a collapsed configuration to an expanded configuration.

As illustrated in FIG. 58, each band member includes an aligning component, such as a groove or a projection. A projection 2186 is disposed on the inner side 2180 of the first member 2156 of the band portion 2106. Similarly, a projection 2188 is disposed on an inner side 2190 of the second member 2158 of the band portion 2106. The projection 2186 is configured to be received by slot 2192, which is defined by ridges 2191 (as illustrated in FIGS. 51, 52, and 54) disposed on the outer side of the ear portion 2102 when the ear warmer 2000 is in its expanded configuration. Similarly, projection 2188 is configured to be received by a slot that is defined by ridges disposed on the outer side of the ear portion 2104 when the ear warmer 2000 is in its expanded configuration. The interaction between the projections 2186 and 2188 and the slots 2192 removably retain the ear warmer in its expanded configuration and provide tactile and/or audible feedback to the user when the ear warmer 2000 is moved into or out of its expanded configuration.

A user may apply force to the ear portions 2102 and 2104 to pivot the ear portions 2102 and 2104 to convert the ear warmer 2000 from its collapsed configuration to its expanded configuration. When the ear portions 2102 and 2104 are moved into their expanded positions, the projections 2186 and 2188 of the band members 2156 and 2158 engage the slots 2192 of the ear portions 2102 and 2104, respectively. Similarly, the user may apply force to the ear portions 2102 and 2104 to pivot the ear portions 2102 and 2104 to convert the ear warmer 2000 from its expanded configuration to its collapsed configuration, and thereby remove the projections 2186 and 2188 of the band members 2156 and 2158 from the slots 2192 of the ear portions 2102 and 2104, respectively. In alterative embodiments, each of the slots can be formed by another configuration such as a "U" shaped projection or an oval projection. In alternative embodiments, ridges and projections can be disposed on the band members and the projections are disposed on the ear portions.

Figure 50:
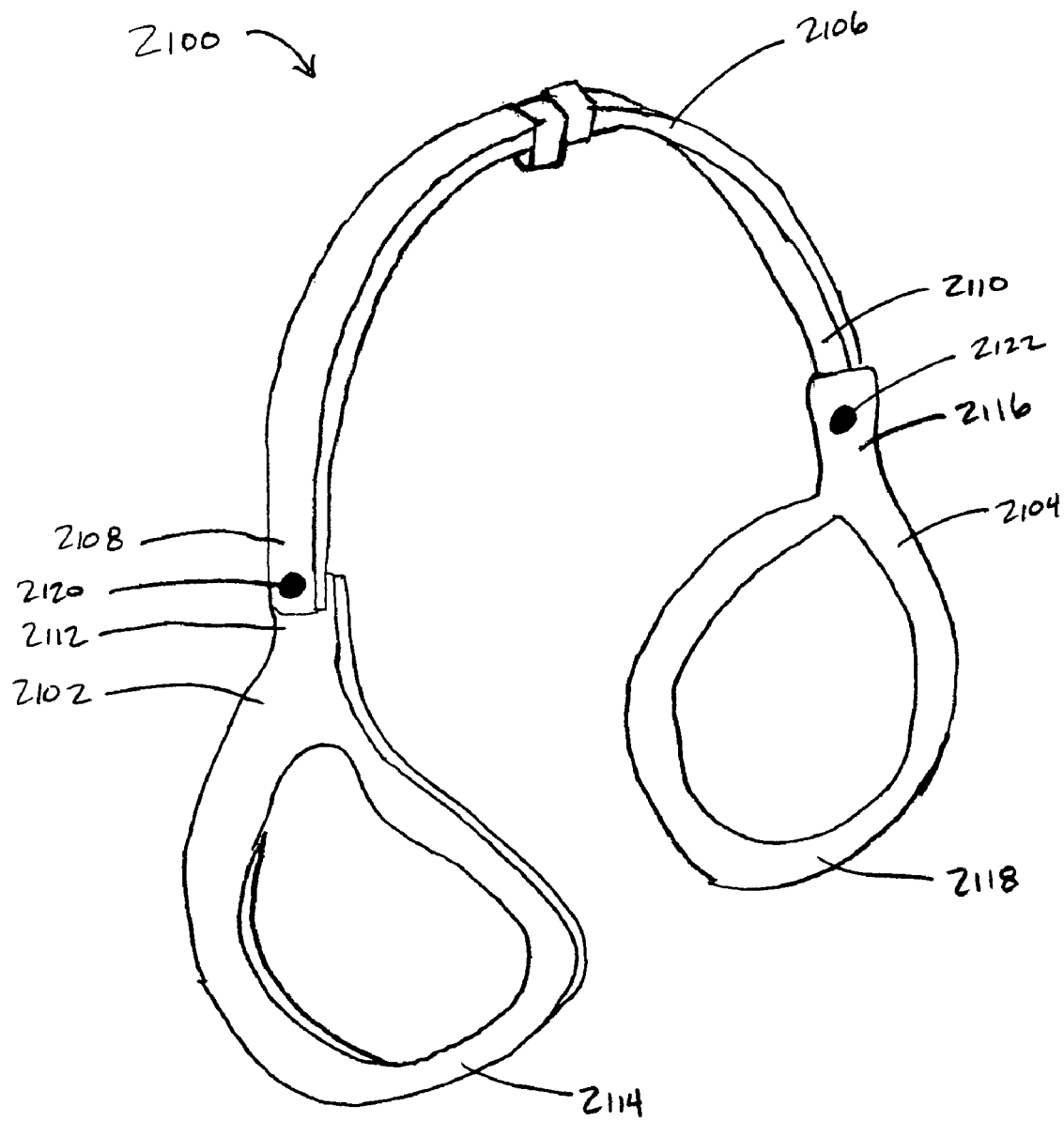
FIG. 50 is a perspective view of a frame of an ear warmer according to an embodiment of the invention.

Turning to the fabric member or shell of an ear warmer incorporating a frame such as that illustrated in FIG. 50, the shell includes a cavity configured to receive the frame of the ear warmer. Several examples of such a shell are disclosed in U.S. patent application Ser. No. 10/056,093, filed on Jan. 28, 2002; the disclosure of which is incorporated herein by reference.

FIG. 60 illustrates a set of membranes for use in constructing a shell 2300 of the ear warmer 2000, according to an embodiment of the invention. The shell 2300 of the ear warmer 2000 includes a first ear membrane 2302, a second ear membrane 2304, a middle membrane 2306, and an outer membrane 2308. The membranes 2302, 2304, 2306, and 2308 can be made of various types of material appropriate for providing warmth while also being comfortable on the wearer's skin. For example, the membranes 2302, 2304, 2306, and 2308 can be made of such materials as fleece, wool, cotton, foam and/or neoprene.

Figure 61:
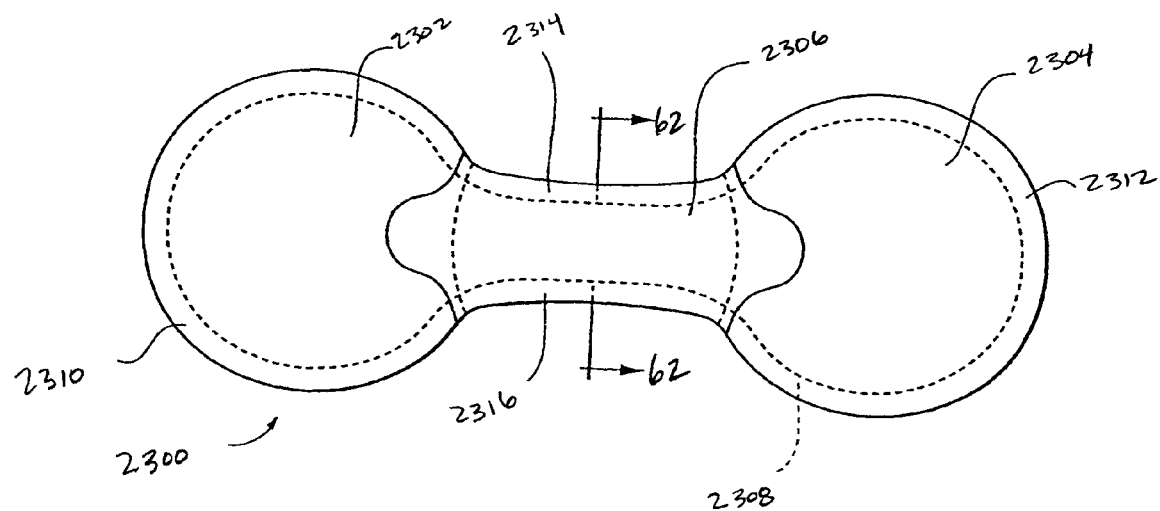
FIG. 61 illustrates an arrangement of the ear warmer shell of FIG. 60 during an interim step in an assembly process.

In the illustrated embodiment, shell 2300 of the ear warmer 2000 can be constructed by first disposing first ear membrane 2302 and second ear membrane 2304 on top of outer membrane 2308. Middle membrane 2306 can then be placed on top of the set of the outer membrane 2308, the first ear membrane 2302, and the second ear membrane 2304 as illustrated in FIG. 61. The ear membranes 2302 and 2304 and the middle membrane 2306 are on top of the outer membrane 2308 in the sense that they are ordered in a particular way; the particular orientation of the collection of membranes as shown in the figures herein are not important. This arrangement of the membranes 2302, 2304, 2306, and 2308 can then be coupled or attached along the perimeter of the shell 2300 via an attachment mechanism, such as an adhesive, a seam, etc.

In one embodiment, this arrangement of the membranes 2302, 2304, 2306, and 2308 is coupled or attached along the perimeter of the shell 2300 of the ear warmer 2000 and the perimeter is covered with a binding (not illustrated). In an alternative embodiment for assembling the membranes illustrated in FIG. 61, the middle membrane 2306 can be placed on the outer membrane 2308 and the ear membranes 2302 and 2304 can be placed on the middle membrane 2306 and the outer membrane 2308.

A variety of couplings or processes can be used to secure the membranes 2302, 2304, 2306, and 2308 together. For example, returning to FIG. 61, portions of the ear membranes 2302 and 2304 and middle membrane 2306 can be bound to outer membrane 2308. Any combination of sewn, bound, or any other couplings can be used to bind the membranes 2302, 2304, 2306, and 2308 to each other. Exemplary methods of assembling the membranes are disclosed in U.S. Pat. No. 6,332,223 B1, issued on Dec. 25, 2001, the disclosure of which is hereby incorporated by reference in its entirety.

Figure 62:
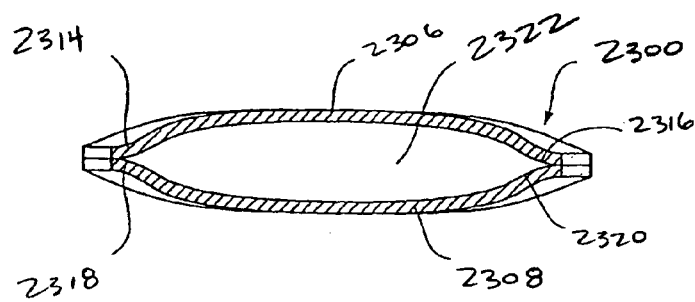
FIG. 62 illustrates a cross-sectional view of the ear warmer shell of FIG. 61 taken along the lines "62-62" in FIG. 61.

FIG. 62 illustrates a cross-sectional view of the shell 2300 of FIG. 61 taken along the line 62-62. In this embodiment, each membrane 2302, 2304, 2306, and 2308 includes a side along a portion of the perimeter of that particular membrane. For example, first ear membrane 2302 includes side 2310, second ear membrane 2304 includes side 2312, middle membrane 2306 includes sides 2314 and 2316, and outer membrane 2308 includes sides 2318 and 2320. The middle membrane 2306 and the outer membrane 2308 are disposed proximate to each other so that the middle membrane sides 2314 and 2316 are proximate to corresponding sides 2318 and 2320 of the outer membrane 2308. Specifically, side 2314 of the middle membrane 2306 is aligned with side 2318 of the outer membrane 2308. Similarly, side 2316 of the middle membrane 2306 is aligned with side 2320 of the outer membrane 2308. The corresponding sides of the other membranes or membrane portions are placed proximate to each other as well.

Figure 63:
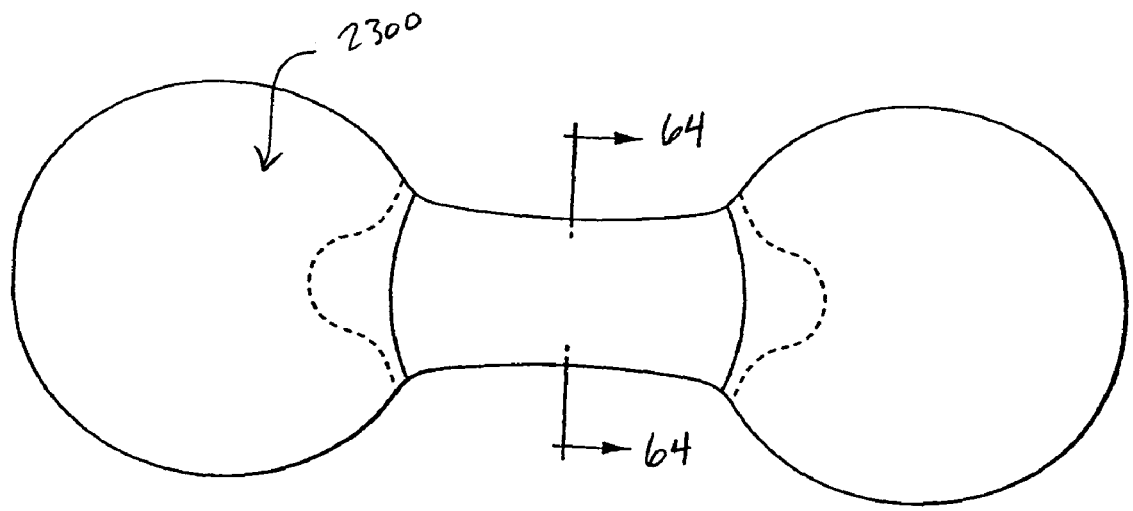
FIG. 63 illustrates an arrangement of an ear warmer shell according to an embodiment of the invention.

In one embodiment, the sides 2310, 2312, 2314, 2316, 2318, and 2320 of the membranes 2302, 2304, 2306, and 2308 as illustrated in FIG. 63 are coupled together and the membranes are turned inside out as disclosed in U.S. Pat. No. 6,332,223 B1, issued on Dec. 25, 2001; the disclosure of which is incorporated by reference.

A top view of an embodiment of the inverted shell 2300 of an ear warmer 2000 is illustrated in FIG. 63. As illustrated, the sides 2310, 2312, 2314, 2316, 2318, and 2320 of the membranes 2302, 2304, 2306, and 2308 and any coupling of the membranes are not apparent or visible from the exterior of the shell 2300 of the ear warmer 2000 and are located in the interior region or cavity 2322 of the shell 2300.

Figure 64:
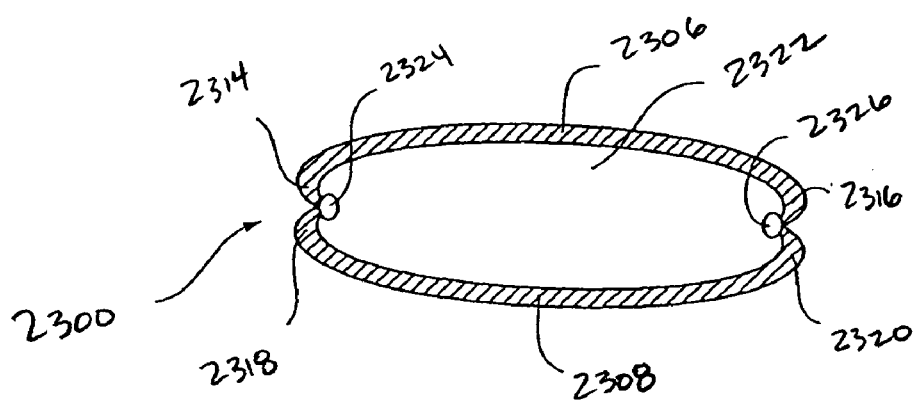
FIG. 64 illustrates a cross-sectional view of the ear warmer shell of FIG. 63 taken along the lines "64-64" in FIG. 63.

FIG. 64 illustrates a cross-sectional view of the shell 2300 of FIG. 63 taken along line 64-64. In this embodiment, the corresponding sides of the membranes adjacent to each other are fixedly coupled together prior to the membranes being inverted to the positions illustrated in FIG. 64. For example, sides 2314 and 2318 are coupled or bound together to form a fixedly coupled portion 2324. Similarly, sides 2316 and 2320 are coupled together to form a fixedly coupled portion 2326. The term "fixedly coupled portion" includes any type of connection or attachment that if pulled apart would result in damage to the membranes. The ear membranes 2302 and 2304 are similarly coupled to the middle membrane 2306 and the outer membrane 2308.

In alternative embodiments, the corresponding sides of the membranes adjacent to each other are removably coupled together. For example, the sides can be removably coupled together using mating connectors, such as hook and loop fasteners, snaps, etc.

In one embodiment, the membranes 2306 and 2308 are coupled together to form fixedly coupled portions 2324 and 2326 using radio frequency welding. As a result, the fixedly coupled portion 2324 includes a weld that couples the middle membrane side 2314 and the outer membrane side 2318. Similarly, the fixedly coupled portion 2326 includes a weld that couples the middle membrane side 2316 and the outer membrane side 2320. In alternative embodiments, the membranes may be coupled together using any type of welding or any other process that couples the membranes together.

Once the membranes 2302, 2304, 2306, and 2308 have been coupled together, the membranes 2302, 2304, 2306, and 2308 are turned inside out, as described above and as illustrated in FIGS. 63 and 64. As illustrated, the fixedly coupled portions 2324 and 2326 are disposed within the interior region or cavity 2322 of the shell 2300 of the ear warmer 2000.

FIG. 65 illustrates an alternative shell for use in constructing an ear warmer 2000 according to another embodiment of the invention. In this embodiment, the shell 2350 includes an inner membrane 2352 includes ear portions 2354 and 2356, and a middle portion 2358. Outer membrane 2360 includes ear portions 2362 and 2364, and a middle portion 2366. Inner membrane 2352 and outer membrane 2360 may be coupled along the perimeters of the membranes 2352 and 2360 to form an inner region or cavity (not illustrated) using any appropriate technology, including, for example, radio frequency welding.

FIG. 66 illustrates a further alternative shell for use in constructing an ear warmer, according to another embodiment of the invention. In this embodiment, the shell 2370 includes a membrane 2372 having multiple portions. The membrane 2372 includes an outer portion 2374 and a middle portion 2376. The shell 2370 can be arranged as follows. First, ear membranes (e.g., ear membranes 2302 and 2304, not illustrated in FIG. 67) can be placed on the corresponding portions 2378 and 2380, respectively, of outer portion 2376. Middle portion 2376 can then be folded on to outer portion 2374 and the ear membranes along the line 2382. The collective perimeter can then be bound, welded, or sewn and the membranes can be turned inside out as described in U.S. Pat. No. 6,332,223 B1, issued on Dec. 25, 2001; the disclosure of which is incorporated by reference.

In an alternative embodiment for assembling the shell 2370 illustrated in FIG. 66, the membranes are not turned inside out. For example, the middle portion 2376 can be folded onto the outer portion 2374 and the ear membranes subsequently placed on the outer portion 2374 and the middle portion 2376. The collective perimeter can then be bound, welded, or sewn.

FIG. 67 illustrates a further alternative shell for use in constructing an ear warmer according to another embodiment of the invention. The shell 2400 includes a membrane 2402 having a first ear portion 2404, a second ear portion 2406, a middle portion 2408, and an outer portion 2410. The portions 2404, 2406, 2408, and 2410 of the membrane can be arranged as follows. First ear portion 2404 can be folded on to the corresponding portion 2412 of the outer portion 2410 along line 2416. Similarly, second ear portion 2406 can be folded on to the corresponding portion 2414 of the outer portion 2410 along line 2418. Middle portion 2408 can then be folded on to outer portion 2410 and ear portions 2404 and 2406 along the line 2420. The collective perimeter can then be bound, welded, or sewn and the membranes 2404, 2406, 2408, and 2410 can be turned inside out.

In an alternative embodiment for assembling the membranes of FIG. 67, the membranes are not turned inside out. For example, the middle portion 2408 can be folded onto the outer portion 2410 along the line 2420. The ear portions 2404 and 2406 can be folded on to the outer portion corresponding portions 2412 and 2414, respectively. The collective perimeter can then be bound, welded, or sewn.

Rather than the separate membranes shown in FIG. 60, variations to FIGS. 66 and 67 are possible where certain membranes are integrally (i.e. monolithically) formed together and folded over. For example, in other embodiments, only one ear membrane is integrally formed with the outer membrane, only two ear membranes are integrally formed with the outer membrane, or only one ear membrane and the middle membrane are integrally formed with the outer membrane.

In an alternative embodiment, the membranes can be integrally formed together at various locations (e.g., discontinuous locations) rather than along the entire fold. In another embodiment, the membranes can be integrally formed at various locations relative to the outer portion of the membrane. For example, rather than the ear portions being integrally formed at the lower location of the outer portion (as shown in FIG. 67), the ear portions can be integrally formed with the outer portion at other locations, such as side locations of the outer portion. The various locations that are possible are those where the portions of the membrane (i.e., the middle portion, and/or the ear portions) fold on to the outer portion of the membrane to appropriately form the ear warmer shell.

While the invention has been described in detail and with references to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. For example, although the fabric member is generally described above as being disposed on the inner side of the ear portion of the frame, the fabric member can instead be disposed on the outer side of the ear frame. In some such embodiments, the fabric member can cover substantially an entirety of the opening on the outer side of the ear portion of the frame and less than an entirety of the opening on the inner side of the ear portion of the frame.

What is claimed is:

1. An ear warmer, comprising:
a frame including a band portion and an ear portion, the ear portion having a length and including a first portion and a second portion, the ear portion having a longitudinal plane, the ear portion having an outer side and an inner side opposite to the outer side, the inner side being proximate to a head of a wearer of the ear warmer and the outer side being oriented away from the head of the wearer, the first portion of the ear portion having a length and being curved about a first axis, the first axis being substantially orthogonal to the longitudinal plane of the ear portion, the second portion of the ear portion having a length and being curved about a second axis, the second axis being substantially orthogonal to the longitudinal plane of the ear portion, the second axis being spaced apart from the first axis, the length of the first portion of the ear portion and the length of the second portion of the ear portion in sum being at least half the length of the ear portion, a thickness of the first portion of the ear portion is greater than a thickness of the second portion of the ear portion, and each of the first axis and the second axis being spaced apart from and extending along the inner side of the ear portion.

2. The ear warmer of claim 1, wherein the band portion includes a first member and a second member, the first member of the band portion has a first end portion and a second end portion, the second end portion of the first member is slidably coupled to the second member of the band portion, the ear portion is coupled proximate the first end portion of the first member of the band portion.

3. The ear warmer of claim 1, wherein the ear portion is tapered from the first portion of the ear portion to the second portion of the ear portion.

4. The ear warmer of claim 1, wherein the band portion has a first member and a second member, the first member includes a first end and a second end, the second end of the first member is slidably coupled to the second member of the band portion, the first member of the band portion has an outer surface, the outer surface of the first member of the band portion includes a plurality of recesses configured to communicate with an end of the second member of the band portion.

5. The ear warmer of claim 1, further comprising:
a shell having a cavity, at least a portion of the frame being disposed within the cavity of the shell.

6. The ear warmer of claim 1, wherein the length of the first portion of the ear portion and the length of the second portion of the ear portion in sum are at least two-thirds the length of the ear portion.

7. The ear warmer of claim 1, wherein the length of the first portion of the ear portion and the length of the second portion of the ear portion in sum are at least four-fifths the length of the ear portion.

8. The ear warmer of claim 1, wherein the ear portion includes a first projecting portion, a second projecting portion, and an extension portion coupled to the first projecting portion and to the second projecting portion, the first projecting portion and the second projecting portion form the first portion of the ear portion, the first projecting portion, the second projecting portion, and the extension portion collectively define an opening therebetween, the first axis extends along an inner side of the first projecting portion, the opening of the ear portion, and then an inner side of the second projecting portion, and the second axis extends substantially parallel to the first axis.

9. The ear warmer of claim 8, wherein the first projecting portion, the second projecting portion and the extension portion collectively have a frusto-conical configuration.

10. The ear warmer of claim 8, wherein each of the first projecting portion, the second projecting portion, and the extension portion has a thickness, the thickness of the first projecting portion and the thickness of the second projecting portion being substantially the same and tapering toward the extension portion, the thickness of the extension portion being tapered toward a distal end of the ear portion.

11. The ear warmer of claim 1, wherein each of the first axis and the second axis does not pass through the ear portion.

12. An ear warmer, comprising:
a frame including a band portion and an ear portion, the ear portion having a length and including a first portion and a second portion, the ear portion having a longitudinal plane, the ear portion having an outer side and an inner side opposite to the outer side, the inner side being proximate to a head of a wearer of the ear warmer and the outer side being oriented away from the head of the wearer, the first portion of the ear portion having a length and being curved about a first axis, the first axis being substantially orthogonal to the longitudinal plane of the ear portion, the second portion of the ear portion having a length and being curved about a second axis, the second axis being substantially orthogonal to the longitudinal plane of the ear portion, the second axis being spaced apart from the first axis, the length of the first portion of the ear portion and the length of the second portion of the ear portion in sum being at least half the length of the ear portion, and each of the first axis and the second axis extends along the inner side of the ear portion and does not pass through the ear portion.

13. The ear warmer of claim 12, wherein the band portion includes a first member and a second member, the first member of the band portion has a first end portion and a second end portion, the second end portion of the first member is slidably coupled to the second member of the band portion, the ear portion is coupled proximate the first end portion of the first member of the band portion.

14. The ear warmer of claim 12, wherein the ear portion is tapered from the first portion of the ear portion to the second portion of the ear portion.

15. The ear warmer of claim 12, wherein the band portion has a first member and a second member, the first member includes a first end and a second end, the second end of the first member is slidably coupled to the second member of the band portion, the first member of the band portion has an outer surface, the outer surface of the first member of the band portion includes a plurality of recesses configured to communicate with an end of the second member of the band portion.

16. The ear warmer of claim 12, further comprising:
a shell having a cavity, at least a portion of the frame being disposed within the cavity of the shell.

17. The ear warmer of claim 12, wherein the length of the first portion of the ear portion and the length of the second portion of the ear portion in sum are at least two-thirds the length of the ear portion.

18. The ear warmer of claim 12, wherein the length of the first portion of the ear portion and the length of the second portion of the ear portion in sum are at least four-fifths the length of the ear portion.

19. An ear warmer, comprising:
a frame including a band portion and an ear portion, the ear portion having a length and including a first portion and a second portion, the ear portion having a longitudinal plane, the first portion of the ear portion having a length and being curved about a first axis, the first axis being substantially orthogonal to the longitudinal plane of the ear portion, the second portion of the ear portion having a length and being curved about a second axis, the second axis being substantially orthogonal to the longitudinal plane of the ear portion, the second axis being spaced apart from the first axis, the length of the first portion of the ear portion and the length of the second portion of the ear portion in sum being at least half the length of the ear portion, and each of the first axis and the second axis is oriented so that it does not intersect with the ear portion.

20. The ear warmer of claim 19, wherein the band portion includes a first member and a second member, the first member of the band portion has a first end portion and a second end portion, the second end portion of the first member is slidably coupled to the second member of the band portion, the ear portion is coupled proximate the first end portion of the first member of the band portion.

21. The ear warmer of claim 19, wherein the ear portion is tapered from the first portion of the ear portion to the second portion of the ear portion.

22. The ear warmer of claim 19, further comprising:
a shell having a cavity, at least a portion of the frame being disposed within the cavity of the shell.

23. The ear warmer of claim 19, wherein the length of the first portion of the ear portion and the length of the second portion of the ear portion in sum are at least two-thirds the length of the ear portion.

24. The ear warmer of claim 19, wherein the length of the first portion of the ear portion and the length of the second portion of the ear portion in sum are at least four-fifths the length of the ear portion.

* * * * *